United States Patent [19]

Souda et al.

[11] Patent Number: 5,840,910

[45] Date of Patent: *Nov. 24, 1998

[54] PYRIDINE DERIVATIVES HAVING ANTI-ULCERATIVE ACTIVITY

[75] Inventors: Shigeru Souda, Ushiku; Norihiro Ueda, Niihari-gun; Shuhei Miyazawa, Toride; Katsuya Tagami, Niihari-gun; Seiichiro Nomoto, Ushiku; Makoto Okita, Tsuchiura; Naoyuki Shimomura, Niihari-gun; Toshihiko Kaneko; Masatoshi Fujimoto, both of Tsukuba-gun, all of Japan; Manabu Murakami, Rockville, Md.; Kiyoshi Oketani, Tsukuba-gun, Japan; Hideaki Fujisaki, Niihari-gun, Japan; Hisashi Shibata, Tsuchiura, Japan; Tsuneo Wakabayashi, Mito, Japan

[73] Assignee: Esai Co., Ltd., Japan

[*] Notice: The term of this patent shall not extend beyond the expiration date of Pat. No. 5,045,552.

[21] Appl. No.: 354,726

[22] Filed: Dec. 6, 1994

Related U.S. Application Data

[60] Continuation of Ser. No. 187,069, Jan. 27, 1994, abandoned, which is a division of Ser. No. 699,442, May 13, 1991, abandoned, which is a division of Ser. No. 462,328, Dec. 28, 1989, Pat. No. 5,045,552, which is a continuation of Ser. No. 119,386, Nov. 10, 1987, abandoned.

[30] Foreign Application Priority Data

Nov. 13, 1986 [JP] Japan .................................. 61-270536
Feb. 2, 1987 [JP] Japan .................................. 62-21989
Mar. 31, 1987 [JP] Japan .................................. 62-77784

[51] Int. Cl.$^6$ .................................................. C07D 401/12
[52] U.S. Cl. .................................... 546/273.7; 514/338
[58] Field of Search ................................ 546/271, 273.7

[56] References Cited

U.S. PATENT DOCUMENTS

| | | | |
|---|---|---|---|
| 4,255,431 | 3/1981 | Junggren et al. | 546/271 |
| 4,337,257 | 6/1982 | Junggren et al. | 546/271 |
| 4,508,905 | 4/1985 | Junggren et al. | 546/271 |

FOREIGN PATENT DOCUMENTS

| | | |
|---|---|---|
| 0 005 129 | 10/1979 | European Pat. Off. . |
| 0 074 341 | 3/1982 | European Pat. Off. . |
| 0 074 341 | 3/1983 | European Pat. Off. . |
| 0 167 943 | 1/1986 | European Pat. Off. . |
| 0 173 664 | 3/1986 | European Pat. Off. . |
| 0173664 | 3/1986 | European Pat. Off. . |
| 0 198 208 | 10/1986 | European Pat. Off. . |
| 198208 | 10/1986 | European Pat. Off. . |
| 2 134 523 | 8/1984 | United Kingdom . |

*Primary Examiner*—Jane Fan
*Attorney, Agent, or Firm*—Nixon & Vanderhye

[57] ABSTRACT

Pyridine derivatives useful for preventing or treating peptic ulcers, pharmaceutical preparations and methods of treating peptic ulcers are disclosed.

2 Claims, No Drawings

PYRIDINE DERIVATIVES HAVING ANTI-ULCERATIVE ACTIVITY

This is a continuation of application Ser. No. 08/187,069, filed Jan. 27, 1994 now abandoned which is a division of Ser. No. 07/699,442 filed May 13, 1991 now abandoned which is a division of Ser. No. 07/462,328 filed Dec. 28, 1989 now Pat. No. 5,045,552 which is a continuation of Ser. No. 07/119,386 filed Nov. 10, 1987 now abandoned.

TECHNICAL FIELD

Novel pyridine derivatives exhibiting activity in treating or preventing peptic ulcers, pharmaceutical compositions containing them, and methods of medical treatment are described.

BACKGROUND ART

Duodenal and gastric ulcers, known collectively as peptic ulcers, are localized erosions of the mucous membrane of the duodenum or stomach, respectively, which expose the underlying layers of the gut wall to the acid secretions of the stomach and to the proteolytic enzyme pepsin. They are believed to be caused by autolysis which is caused by an imbalance between offensive factors, such as acid or pepsin and defensive factors, such as resistance of the mucous membrane, mucilage secretion, bloodstream or control of the duodenum. Peptic ulceration in the moat common disease of the gastro-intestinal tract and it is estimated that approximately 10 to 20% of the adult male population will experience at some time in their lives.

Peptic ulcers are cured or prevented by medical treatment, in principle, and many pharmacotherapies have been suggested, some with high degrees of success.

Clinically useful modialities include $H_2$-blockers, such as cimetidine and ranitidine, as anti-ulcer agents. It has been noted, more recently, that inhibitors of $H^+$-$K^+$-ATPase, an enzyme specifically present in the parietal cells of the stomach, can effectively inhibit the secretion of gastric acid in mammals, including man, therefore it has been expected that a new class of anti-ulcer agents from this viewpoint will come into existance. More specifically, a wide variety of compounds having a benzimidazole structure have been proposed. Among these compounds is Omeprazole, currently under active development, a the most promising compound; see U.S. Pat. Nos. 4,337,257; 4,255,431; and 4,508,905. These patents describe compounds with a methoxy group in the 4-position of the pyridine ring. Omeprazole, having the formula:

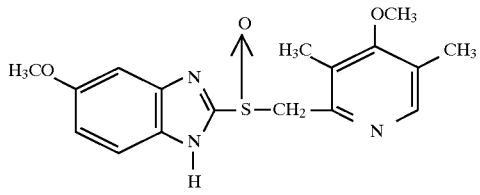

and further 2-(4-methoxyethoxypyridine-2-yl)-methylsulfinyl-5-methyl-1H-benzimidazole in the working examples thereof.

Related benzyimidazole-type compounds having anti-ulcer activities are described in published application GB 2.134.523A. More specifically, compounds in which the 4-position of the pyridine ring is substituted with an alkoxy-alkoxy group with each alkoxy group containing 1–2 carbons are described. Example 157 of this patent describes 2-(3,5-dimethyl-4-methoxyethoxypyridine-2-yl) methylsulfinyl-5-phenyl-1H-benzimidazole. Other substitutions on various positions of the benzyl and pyridine rings are also described.

Biological tests reported in tables 4 and 5 of this published application report significant biological effects on gastric acid secretion, both in isolated cells and in laboratory animals, when the 4-position on the pyridine ring is substituted with a methoxy group.

Additional benzimidazole-type compounds, in which the substituent at the 4-position on the pyridine ring is a benzyloxy group, are described in European patent application 0,167,943.

DISCLOSURE OF THE INVENTION

The present inventors have discovered a class of novel compounds with a more excellent anti-ulcer activity than Omeprazole which is regarded, at the present time, as the most significant benzimidizole-type compound having anti-ulcer activity. As a result of intensive studies, it has been found that compounds represented by formula (I) are more potent in inhibiting gastric acid secretion in comparison with Omeprazole. The present invention has been accomplished on the basis of this finding.

The present invention includes a class of pyridine derivatives represented by the general formula:

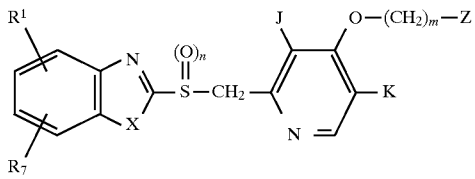

where $R^1$ and $R^2$ may be the same or different, each being a hydrogen atom, a lower alkyl, lower alkoxy, halogenated lower alkyl, lower alkoxycarbonyl or carboxyl group or a halogen atom;

X is a group represented by the formula: —O—, —S— or

(in which $R^3$ stands for a hydrogen atom or a lower alkyl, phenyl, benzyl or lower alkoxycarbonyl group); and A represents:
1. a group of the formula:

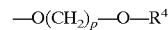

where p is in integer of 1 to 3 and $R^4$ is hydrogen atom or a lower alkyl, aryl or aralkyl group,
2. a group of the general formula:

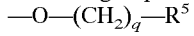

where q in an integer of 1 to 3 and $R^5$ is a halogen atom or an alkoxycarbonyl, aryl or heteroaryl group,
3. a group of the general formula:

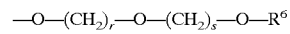

where r and s each independently are an integer of 1 to 5 and $R^6$ is a hydrogen atom or a lower alkyl group, 4. a group or the formula:

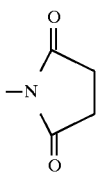

5. a group of the formula:

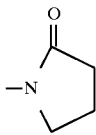

6. a group of the formula:

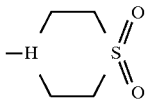

7. a group of the general formula:

where t in an integer of 0 to 2 and A is a group of the general formula:

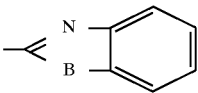

(where B is a group represented by the formula: —NH—, —O— or —S—), a lower alkyl, alkoxycarbonylmethyl, pyridyl or furyl group or a group of the general formula:

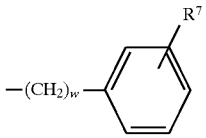

8. a group of the general formula:

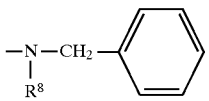

where $R^8$ is an acetoxy or lower alkyl group, or 9. a group of the general formula:

where $R^9$ is a hydrogen atom or a lower alkyl or aryl group;

n is an integer of 0 to 2; m is an integer of 2 to 10, and J and X, which may be the same or different from each other, each stand for a hydrogen atom or a lower alkyl group, with the proviso that when Z is a group falling under the above category (9) $R^9$ in a lower alkyl group and m stands for an integer of 3 to 10, and pharmaceutically acceptable salts thereof.

The same definitions for $R^1$, $R^2$, X, n, J, K, Z and more used throughout the specification that follows and in the appended claims.

Also disclosed are Pharmaceutical compositions containing these compounds as the active ingredient(s) and procedures for preventing or treating peptic ulcers in mammals, including humans, using theme pharmaceutical compositions.

In the definition of the compounds of general formula (I) given above, the lower alkyl group defined above with respect to $R^1$, $R^2$, $R^3$, $R^4$, $R^6$, A, $R^7$, $R^8$, J and K in the compound (I) of the present invention may be a straight-chain or branched alkyl groups having 1 to 6 carbon atoms. Examples include methyl, ethyl, n-propyl, n-butyl, isopropyl, isobutyl, 1-methylpropyl, tert-butyl, n-pentyl, 1-ethylpropyl, isoamyl and n-hexyl groups, among which ethyl and ethyl groups are most preferred.

The lower alkoxy group and the lower alkoxy moiety of the lower alkoxycarbonyl group defined above with respect to $R^1$ and $R^2$ may be in alkoxy group derived form the above lower alkyl group. Methoxy and ethoxy groups are most preferred.

The halogen atom defined above includes chlorine, bromine, iodine or fluorine. The aryl group defined above with respect to $R^4$ and $R^5$ may be phenyl, tolyl, xylyl, naphthyl or the like which may be substituted with a lower alkoxy or hydroxyl group, a halogen atom or the line.

Examples of the arylalkyl defined above with respect to $R^4$ include benzyl and phenethyl groups.

Examples of the heteroaryl group defined above with respect to $R^5$ include pyridyl and furyl groups.

In the definition of Z in general formula (1), groups 1, 2, 3, 4, 5 and 9 are preferred; group 9 is the most preferred. As for $R^1$ and $R^2$, hydrogens for both and then a combination of a lower alkyl, inter alia methyl, for $R^1$ and hydrogen for $R^2$ are preferred. X is preferably —$NR^3$ where $R^3$ is hydrogen. A preferred value for n is 1. The preferred substituents for J and K are both hydrogen or where J is lower alkyl, inter alia methyl, and X is hydrogen, or when J is hydrogen X is lower alkyl, inter alia methyl. Thus, J or X are independently preferably hydrogen or methyl, most preferably J is methyl and K is hydrogen.

A first preferred class of compounds falling within the compounds of general formula (1) are represented by the following formula:

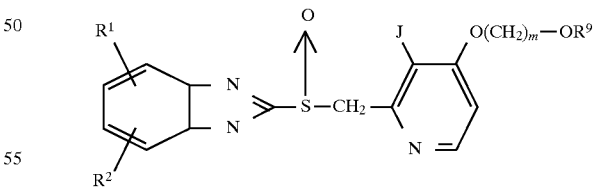

(A)

where $R^1$, $R^2$, J, m and $R^9$ have the same meanings as defined above). It formula A, the preferred $R^1$ and $R^2$ substituents are both hydrogen, or $R^1$ is 5-lower alkoxy, 5-lower alkyl or 5-halogenated lower alkyl and $R^2$ is hydrogen. Tho preferred substituent for J is hydrogen or methyl; the preferred value for m is in the range of 3 to 10, the most preferred being 3; and the preferred $R^9$ substituent is lower alkyl, inter alia methyl, or aryl. Among these possibilities for the compounds of formula A the preferred combination is when $R^1$ and $R^2$ are both hydrogen, J is methyl, m is 3 and $R^9$ in methyl.

A second group of preferred compounds are combinations of the above substituents where both $R^1$ and $R^2$ are hydrogen, J is hydrogen, m is 3 and $R^9$ is methyl.

A third group of preferred compounds falling within formula A in when both $R^1$ and $R^2$ are hydrogen, J in methyl, m in 2 and $R^9$ is benzyl.

A second clans of compounds falling within general formula (I) are represented by the following formula:

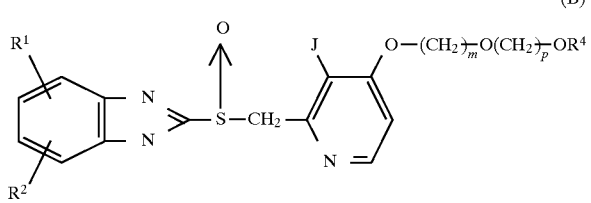

(B)

(where $R^1$, $R^2$, p, m and $R^4$ have the same meanings as given above). In formula (B), the preferred substituents for $R^1$ and $R^2$ are both hydrogen or when $R^1$ is lower alkoxy, 5-lower alkyl or 5-halogenated lower alkyl, $R^2$ is hydrogen. The preferred value of m in 2 or 3; the preferred value for p is 2 or 3; and the preferred substituent for $R^4$ in methyl or benzyl. Of the above possibilities for formula (B), the moist preferred combination is where $R^1$ in 5-methyl, $R^2$ is hydrogen, J is methyl, m in 2, p is 2 and $R^4$ is methyl.

Examples of the pharmaceutically acceptable salt include salts with inorganic acids, such as hydrochloride, hydrobromide, sulfate and phosphate; those with organic acids, such as acetate, maleate, tartrate, methanesulfonate, benzenesulfonate, and toluenesulfonate; and those with amino acids such as arginine, aspartic acid and glutamic acid.

Some of the compounds according to the present invention can form a salt with a metal each as Na, K, Ca or Mg. These metal salts are also included among the pharmaceutically acceptable salts of the present invention. For example, compounds represented by the general formula (I), wherein X in a group of $$-\underset{R^3}{N}-$$

and $R^3$ in a hydrogen atom, or compounds represented by the general formula (I), wherein Z is a group falling under the category 7 and B is a group of —NH—, can be present an a metal salt.

Although the compounds of the present invention may also be prevent as a hydrate or an a stereoisomer, it is a matter of course that these hydrates and stereoisomers are also included in the scope of the present intention.

Now, the effect of the compounds of the present invention will be described by referring to the following pharmacological experiments.

PHARMACOLOGICAL EXPERIMENT

Inhibition Against the Activity of $H^+$-$K^+$ ATPase (1) Preparation of $H^+$-$K^+$ ATPase Prepared from the fundic-glands of a fresh mucous membrane of a pig stomach according to a modified method of Saccomani al. (see Biochem. and Biophys. Acta, 464; 313 (1977)).

(2) Measurement of the activity of $H^+$-$K^+$ ATPase

The compound of the present invention was incubated at various concentration in a 40 mM Tris-HCl buffer solution having a pH of 7.40 together with $H^+$-$K^+$ ATPase and 10 μg/ml of a protein at 37° C. for 30 minutes, followed by the addition of 15 mM KCl. After 10 minutes, the ATPase reaction was initiated by the addition of 3 mM of $MgCl_2$ and ATP. After 10 minutes, the amount of the released inorganic phosphoric acid was determined according to the method of Yoda and Hokin (see Biochem. Biophys. Res. Com., 40, 880 (1970)).

The test compound was used as a solution in methanol.

The inhibitory effect was determined by subtracting the amount of the released inorganic acid observed with respect to the case wherein a solution of a test compound was added from that with respect to the control wherein only a solvent was added to determine a difference and dividing this difference by the latter amount and shown by percentage. The inhibitory effect is shown in Table 1 in terms of $IC_{50}$.

(3) The results are shown in Table 1.

TABLE 1

| No. | Compound | $IC_{50}$ (M) |
|---|---|---|
| 1 |  | $9.2 \times 10^{-7}$ |

TABLE 1-continued

| No. | Compound | IC$_{50}$ (M) |
|---|---|---|
| 2 | 5-methoxy-benzimidazole-2-yl sulfinylmethyl-3-methyl-4-(2-phenoxyethoxy)ethoxy pyridine | $1.4 \times 10^{-6}$ |
| 3 | 5-trifluoromethyl-benzimidazole-2-yl sulfinylmethyl-3-methyl-4-(2-phenoxyethoxy)ethoxy pyridine | $1.0 \times 10^{-6}$ |
| 4 | benzimidazole-2-yl sulfinylmethyl-3-methyl-4-[2-(succinimido)ethoxy] pyridine | $1.1 \times 10^{-5}$ |
| 5 | benzimidazole-2-yl sulfinylmethyl-3-methyl-4-[2-(2-oxopyrrolidin-1-yl)ethoxy] pyridine | $2.4 \times 10^{-6}$ |
| 6 | 5-trifluoromethyl-benzimidazole-2-yl sulfinylmethyl-3-methyl-4-(OCH$_2$CH$_2$OCH$_2$CH$_2$OCH$_3$) pyridine | $5.5 \times 10^{-7}$ |
| 7 | 5-methoxy-benzimidazole (Na) -2-yl sulfinylmethyl-3-methyl-4-(OCH$_2$CH$_2$OCH$_2$CH$_2$OCH$_3$) pyridine | $1.7 \times 10^{-6}$ |

TABLE 1-continued

| No. | Compound | IC$_{50}$ (M) |
|---|---|---|
| 8 | (benzimidazole)-S(O)-CH$_2$-(3-methyl-4-(O-(CH$_2$)$_2$-OCH$_2$-(2-pyridyl))pyridyl) | $1.2 \times 10^{-6}$ |
| 9 | (5-methoxybenzimidazole)-S(O)-CH$_2$-(3-methyl-4-(O-(CH$_2$)$_2$-N-(2-oxopyrrolidinyl))pyridyl) | $1.3 \times 10^{-5}$ |
| 10 | (benzimidazole)-S(O)-CH$_2$-(3-methyl-4-(OCH$_2$CH$_2$OH)pyridyl) | $1.9 \times 10^{-6}$ |
| 11 | (5-methoxy-N-Na-benzimidazole)-S(O)-CH$_2$-(3-methyl-4-(OCH$_2$CH$_2$OCH$_2$CH$_2$OCH$_2$-phenyl)pyridyl) | $4.2 \times 10^{-6}$ |
| 12 | (N-Na-benzimidazole)-S(O)-CH$_2$-(3-methyl-4-(OCH$_2$CH$_2$OCH$_2$CH$_2$OCH$_2$-phenyl)pyridyl) | $2.6 \times 10^{-6}$ |
| 13 | (5-CF$_3$-N-Na-benzimidazole)-S(O)-CH$_2$-(3-methyl-4-(OCH$_2$CH$_2$OCH$_2$CH$_2$OCH$_2$-phenyl)pyridyl) | $6.3 \times 10^{-7}$ |

TABLE 1-continued

| No. | Compound | IC$_{50}$ (M) |
|---|---|---|
| 14 | | $1.0 \times 10^{-5}$ |
| 15 | | $7.2 \times 10^{-8}$ |
| 16 | | $1.7 \times 10^{-6}$ |
| 17 | | $3.5 \times 10^{-6}$ |
| 18 | | $3.3 \times 10^{-6}$ |
| 19 | | $1.7 \times 10^{-6}$ |

TABLE 1-continued

| No. | Compound | IC$_{50}$ (M) |
|---|---|---|
| 20 | [benzimidazole-Na]—S—CH$_2$—[pyridine with CH$_3$, OCH$_2$CH$_2$SCH$_3$], →O | $2.3 \times 10^{-6}$ |
| 21 | [benzimidazole-H]—S—CH$_2$—[pyridine with CH$_3$, OCH$_2$CH$_2$O—phenyl], →O | $1.3 \times 10^{-6}$ |
| 22 | [benzimidazole-H]—S—CH$_2$—[pyridine with CH$_3$, OCH$_2$CH$_2$CH$_2$OH], →O | $1.9 \times 10^{-6}$ |
| 23 | [benzimidazole-H]—S—CH$_2$—[pyridine with CH$_3$, OCH$_2$CH$_2$OCH$_2$CH$_2$Cl], →O | $1.4 \times 10^{-6}$ |
| 24 | Omeprazole | $1.1 \times 10^{-5}$ |

It is apparent from the results of the experiments that the compound of the present invention exhibits a high inhibitory effect on the activity of H$^+$-K$^+$ ATPase and is highly safe, so that it can effectively inhibit the secretion of an acid and is therefore effective in the therapy or prevention of human and animal peptic ulcer.

Further, the compound of the present invention exhibits excellent recovery of the secretion of an acid and therefore is superior to the one of the prior art in this respect.

Chronic gastric fistula dogs were used. The test compound was intraduodenally administered to each dog in an amount of 4 mg per kg. In 1, 24, 48 and 72 hours, respectively, from the time of administration, pentagastrin (6 micron grams per kg) was injected intramuscularly into the dog. Gastric acid secretion, determined and recovery thereof, was determined in terms of percent of the control response. Results from this test are shown in Table 3.

From the results, it can be determined that within one hour from the intraduodenal administration the pentagastrin-stimulated gastric acid secretion was completely inhibited in both tests of compound 19 and Omeprazole. In the test, acid output with compound 19 was 61.9 percent and 121.5 percent in comparison with the control group after 24 and 48 hours, respectively. On the other hand, in the same test using Omeprazole, gastric acid secretion was 108.4 percent after 72 hours. With both compound 19 and Omeprazole, 48 hours and 72 hours were required for the acid secretion to recover, respectively.

PHARMACOLOGICAL EXPERIMENT 2

Inhibitory Effect on Gastric Acid Secretion

Chronic gastric fistula dogs were used. Gastric acid secretion of each dog was stimulated by infusing 100 micron grams per kg per hour of histamine. After one hour of histamine infusion, each of the test compounds was administered intraduodenally to each dog, and after one hour of administration, the amount of gastric acid secretion of each test dog was determined. Results wore compared with the control group to which no test compound had been administered and are expressed in terms of percent inhibition.

The inhibitory effect exhibited by the test compound on the histamine-stimulated gastric acid secretion of the chronic gastric fistula dogs is shown in Table 2. The values of ID 50, calculated from the dose-inhibition curve of the test compounds, are 59.9 micron grams per kg for compound 19 and 112.2 micron grams per kg for Omeprazole, demonstrating that compound 19 was two times more potent than Omeprazole. Compound 19 is shown in Table 1 of Experiment 1 and in working example 33 shown below.

TABLE 2

| μg/Kg | % Inhibition of acid output | |
|---|---|---|
| | compound 19 | omeprazole |
| 31.25 | 34.4 | — |
| 62.5 | 50.1 | 41.1 |
| 125 | 67.7 | 48.6 |
| 250 | 87.4 | 62.1 |
| 500 | 100.0 | 91.2 |
| 1000 | — | 100.0 |

TABLE 3

| Compound | 1 hr | 24 hr | 48 hr | 72 hr |
|---|---|---|---|---|
| compound 19 | 0 | 61.9 | — | — |
| Omeprazole | 0.3 | 32.3 | 69.1 | 108.4 |

The results of the three pharmacological experiments an reported above demonstrate that the compound of the invention exhibits a significant inhibitory effect on the activity of $H^+$-$K^+$ATPase.

Among these compounds, compound 19 of the invention unexpectedly has a more potent inhibitory activity on gastric acid secretion as compared with Omeprazole, which itself is highly inhibitory of gastric acid secretion along the compounds having a benzimidazole-type structure.

Further, it should be noted that the compound of the present invention unexpectedly exhibits a faster recovery or resumption of gastric acid secretion than Omeprazole.

At present, this $H^+$-$K^+$ATPase-inhibiting agent is believed to have a more potent inhibitory activity against gastric acid secretion than an $H_2$-blocker compound, and thus, in the future, may be the drug of choice for the treatment of ulcers.

But, while more potent inhibitory activity against gastric acid secretion in desirable, too long-lasting inhibition of gastric acid secretion is not preferable for an anti-ulcer agent. For example, it gives rise to the proliferation of Enterochromaffin-like calls (ECL cell) and formation of carcinoid derived from hypergastrinemia; see "Digestion", vol. 35, suppl. 1, page 42 to 55 (1986); the increase in the gastric bacterial flora and endogenous production of N-nitro compounds; see "Brit. Med. J.", Vol. 289, page 717 (1984); and difficulty in determining the appropriate dosage regimen.

Thus, an $H^+$-$K^+$ATPase-inhibitory agent which possesses an excellent recovery of gastric acid secretion is most preferred.

No toxicological influence has been observed for compound 19 (working example 33), which in a representative compound of this invention, in beagle dogs to which it was orally administered at 10 mg/kg per day for one week, and in rate to which it was orally administered at 50 mg/kg per day for one week.

Thus, compound 19, as representative of this invention, exhibits a significant inhibitory effect upon the activity of $H^+$-$K^+$ATPase coupled with the desirable property of excellent gastric acid secretion recovery.

Compound 19, as representative of the compounds of this invention, is thus considered to be effective in the treatment or prevention of peptic ulcers (stomach ulcers and duodenal ulcers) in animals, including human.

The compounds of the present invention are administered for the therapy or prevention of peptic ulcers either orally as powders, granules, capsules or syrup, or parenterally as an injection, or is an external preparation or drop, or as a suppository. Although the dose remarkably varies depending upon symptoms, age or kind of ulcer(s), it may be about 0.01 to 200 mg/kg, preferably 0.05 to 50 mg/kg, still preferably 0.1 to 10 mg/kg a day, and may be administered in a single dose or in divided doses, for example from 2 to 4 times a day.

The drug may be formulated into pharmaceutical presentations using conventional formulation procedures. More specifically, a solid drug for oral application can be prepared by mixing in active principle with filler and, if necessary, binder, disintegrating agent, lubricant, coloring agent, corrigent or the like and converting the obtained mixture into a tablet, coated tablet, granule, powder or capsule.

Examples of the filler include lactose, corn starch, sucrose, glucose, sorbitol, crystalline cellulose and silicon dioxide, while those of the binder include polyvinyl alcohol, polyvinyl ether, ethylcellulose, methylcellulose, acacia, tragacanth, gelatin, shellac, hydroxypropylcellulose, hydroxypropylstarch and polyvinylpyrrolidone. Examples of the disintegrating agent include starch, agar, gelatin powder, crystalline cellulose, calcium carbonate, sodium hydrogencarbonate, calcium citrate, dextrin and pectin, while those of the lubricant include magnesium stearate, talc, polyethylene glycol, silica and hardened vegatable oils. The coloring agent may be any one which is permitted to be added to drugs. Examples of the corrigent include cacao powder, mentha herb, aromatic powder, mentha oil, borneol and powdered cinnamon bark. Of course, these tablets and granules may be, if necessary, coated with sugar, gelatin or the like.

The injection can be prepared by mixing an active principle with pH adjusting agent, buffer, stabilizer, solubilizing agent or the like and treating the obtained mixture according to an ordinary process to obtain a subcutaneous, intramuscular for intravenous injection.

Preparation Process

The compound of the present invention can be prepared by various processes, representative examples of which will now be described.

Preparation Process A

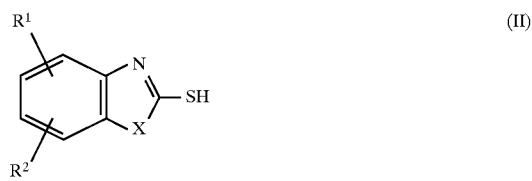

(II)

wherein $R^1$, $R^2$ and X are as defined above

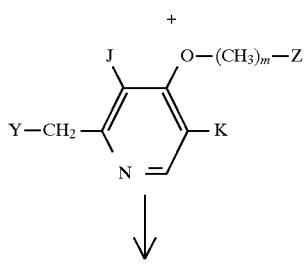
(III)

wherein m, Z, J and K are as defined above and Y stands for a halogen atom or a sulfonyloxy group

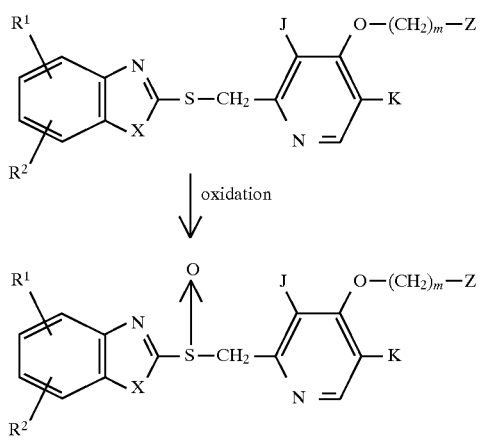

That is, a compound represented by the general formula (II) is reacted with a halide or sulfonate represented by the general formula (III) to obtain a compound represented by the general formula (I') which is an objective compound of the present invention.

Examples of the halogen atom defined with respect to Y include chlorine, bromine and iodine, while those of the sulfonyloxy group include alkylsulfonyloxy groups such as methylsulfonyloxy and ethylsulfonyloxy groups and aromatic sulfonyloxy groups such as benzenesulfonyloxy and tosyloxy groups.

The above reaction is preferably carried out in the presence of an acid scavenger. Examples of the acid scavenger include carbonates and hydrocarbonates of alkali metals, such as potassium carbonate, sodium carbonate and sodium hydrogencarbonate; alkali hydroxides such as sodium hydroxide and potassium hydroxide and organic amines such as pyridine and triethylamine. Examples of the solvent to be used in the reaction include alcohols such as methyl and ethyl alcohols, tetrahydrofuran, dioxane, dimethylformamide, dimethyl sulfoxide and mixtures thereof with water.

The reaction temperature may be from −40° C. to the boiling point of the solvent used, preferably from about 0° to 60° C.

The obtained compound (I') can be easily oxidized into its sulfinyl derivative (I'') which is an objective compound of the present invention corresponding to a compound of the general formula (I) wherein n is 1.

This oxidation can be carried out according to an ordinary process by the use of an oxidizing agent such as hydrogen peroxide, peracetic acid, m-chloroperbenzoic acid, sodium hypochlorite or sodium hypobromite. The solvent to be used in the oxidation is generally selected from among dichloromethane, chloroform, benzene, toluene, methanol, ethanol and the like. The oxidation temperature may be from −70° C. to the boiling point of the solvent used, preferable from −60° to 25° C.

Furthermore, a sulfone derivative which is an objective compound of the present invention corresponding to a compound of the formula (I) wherein n is 2 can be prepared by, for example, the following process:

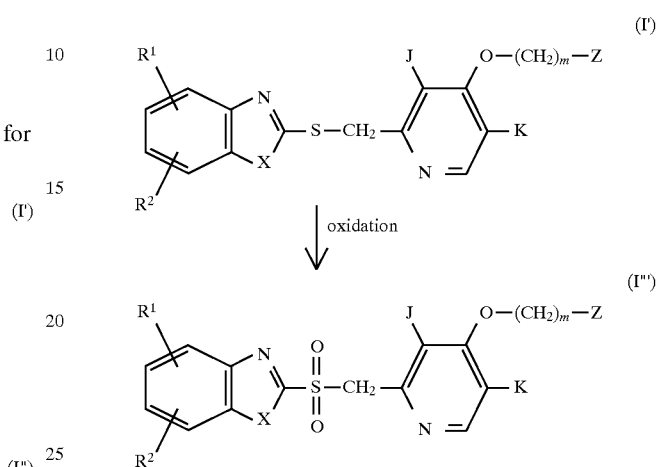

wherein $R^1$, $R^2$, X, J, m and Z are as defined above.

That is, the thio ether derivative represented by the general formula (I') which is an objective compound of the present invention is oxidized into its sulfone derivative represented by the general formula (I''') which is another objective compound of the present invention.

More precisely, the sulfone derivative (I''') which is an objective compound of the present invention can be prepared by dissolving the compound (I') in a solvent selected from among aromatic hydrocarbons such as benzene, toluene and xylene; halogenated hydrocarbons such as dichloromethane, chloroform and carbon tetrachloride; water; alcohols such as methanol and ethanol; ethyl acetate; acetone; acetic acid and the like to obtain a solution, adding at least twice by equivalent as much oxidizing agent selected from among hydrogen peroxide, peracetic acid, m-chloroperbenzoic acid, sodium hypochlorite, sodium m-periodate and the like to the solution under cooling with ice or at a room temperature and reacting the compound (I') with the oxidizing agent.

Alternatively, the sulfone derivative (I''') can be prepared by dissolving the sulfoxide derivative (I'') obtained by the above process in a solvent such as chloroform, adding an oxidizing agent such as m-chloroperbenzoic acid to the obtained solution and reacting the sulfoxide derivative (I'') with the oxidizing agent.

Preparation Process B

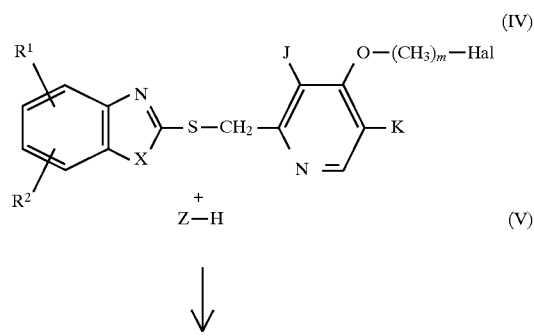

-continued

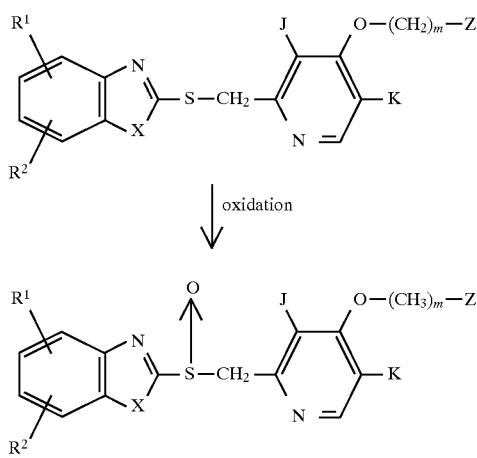

(I')

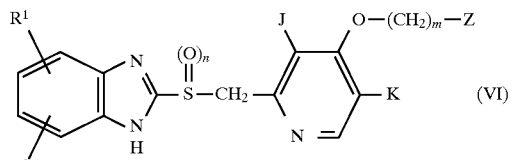

(VI)

+

R³Hal (VII)

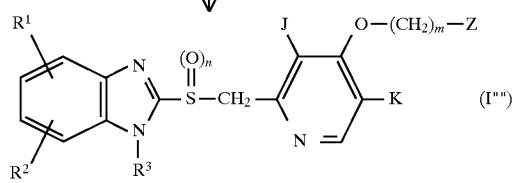

(I'''')

wherein $R^1$, $R^2$, X, m, J, K and Z are as defined above and Hal stands for a halogen atom.

That is, an objective compound represented by the general formula (I) can be prepared by reacting a halide represented by the general formula (IV) with an alcohol, thiol or amine represented by the general formula: Z—H (V). This reaction is preferably carried out in the presence of an acid scavenger. Examples of the acid scavenger include carbonates and hydrogencarbonates of alkali metals, such as potassium carbonate and sodium carbonate; alkali hydroxides such as sodium hydroxide and potassium hydroxide and triethylamine. Examples of the solvent to be used in the reaction include ethers such as tetrahydrofuran and dioxane; ketones such as acetone and methyl ethyl ketone; benzene homologues such as benzene, tolylene and xylene; acetonitrile; dimethylformamide; dimethyl sulfoxide and hexamethylphosphoric triamide. The reaction may be carried out either under cooling with ice or at a temperature not exceeding the boiling point of the solvent used.

The obtained compound (I') which is an objective compound of the present invention can be oxidized into its sulfinyl derivative represented by the general formula (I") in a similar manner to that described above in Preparation process A.

Preparation Process C

A compound represented by the general formula (I) wherein X is a group represented by the formula:

(wherein $R^3$ is a group selected from among those defined above except a hydrogen atom) can be prepared by the following process:

wherein $R^1$, $R^2$, n, J, K, m and Z are as defined above; Hal stands for a halogen atom and $R^3$ is a group selected from among those defined with respect to $R^3$ of the formula (I) except a hydrogen atom, i.e., a lower alkyl, phenyl, benzyl or lower alkoxycarbonyl group.

That is, a compound represented by the general formula (I'''') which is an objective compound of the present invention can be prepared by condensing a compound represented by the general formula (VI) with a halide represented by the general formula (VII) according to an ordinary process.

This condensation is carried out in the absence of any solvent or in an organic solvent inert to the condensation selected from among benzene, ethanol, xylene, tetrahydrofuran, chloroform, carbon tetrachloride, dimethylformamide and the like either at a room temperature or under cooling with ice or heating for several hours according to an ordinary process. The condensation can be expedited by the use of a dehydrohalogenating agent selected from among inorganic salts such as sodium hydrogencarbonate, potassium carbonate, sodium carbonate and caustic soda or organic bases such as triethylamine, pyridine, pyrimidine and diethylaniline.

Further, the thio ether derivative represented by the general formula (I''''), wherein n is 0, which has been prepared by condensing a compound represented by the general formula (VI), wherein n is 0, with a halide (VII) can be easily oxidized into the corresponding sulfoxide (n=1) or sulfone (n=2) derivative according to the same process as that described above.

Process for the Preparation of Starting Materials

The compound represented by the general formula (III) to be used in the Preparation process A as a starting material can be prepared by, for example, the following process:

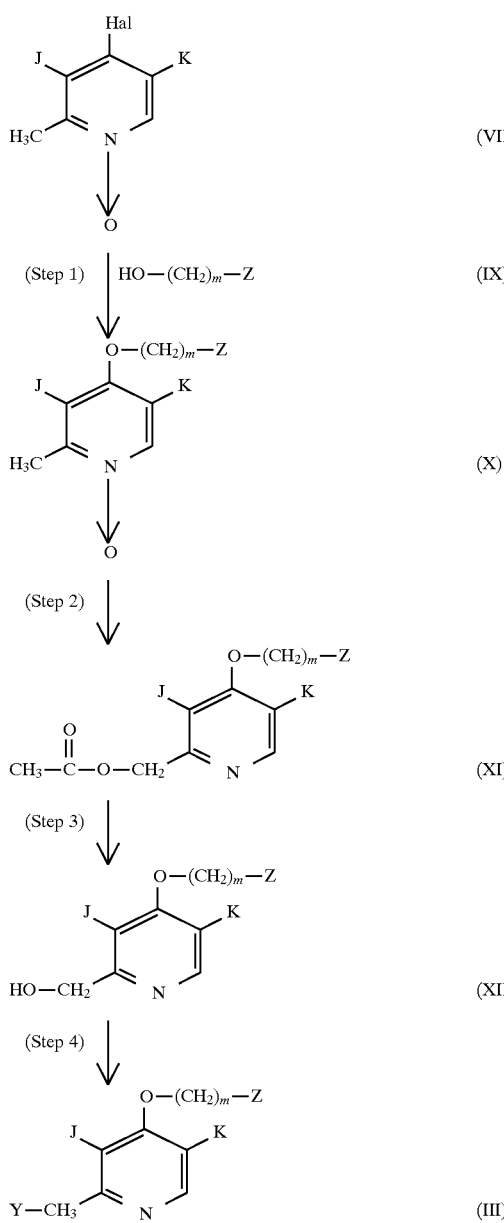

wherein m, Z, J, K and Y are as defined above.

(Step 1)

A 4-halogenopyridine oxide derivative (VIII) (for example, 4-chloro-2,3-dimethylpyridine 1-oxide) is reacted with an alcohol derivative represented by the general formula (IX) in the presence of a base to obtain an alkoxy derivative represented by the general formula (X).

Examples of the base include alkali metal hydrides such as sodium hydride and potassium hydride; alkali metals such as metallic sodium; sodium alcoholates such as sodium methoxide and alkali metal hydroxides such as sodium hydroxide and potassium hydroxide. This reaction is carried out either in the absence of any solvent or in a solvent selected from among ethers such as tetrahydrofuran and dioxane; ketones such as acetone and methyl ethyl ketone; benzene homologues such as benzene, toluene and xylene; acetonitrile; dimethylformamide; dimethyl sulfoxide; hexamethylphosphoric triamide and the like at a temperature of from one under cooling with ice to the boiling point of the solvent used.

(Step 2)

The alkoxy derivative of the general formula (X) prepared in the Step 1 is heated in acetic anhydride to a temperature of about 60° to 100° C. to obtain an acetoxymethylpyridine derivative represented by the general formula (XI).

(Step 3)

The acetoxymethylpyridine derivative (XI) prepared in the Step 2 is hydrolyzed into the corresponding 2-hydroxymethylpyridine derivative represetned by the general formula (XII).

This hydrolysis is generally carried out under alkaline conditions.

(Step 4)

The 2-hydroxymethylpyridine derivative (XII) prepared in the Step 3 is halogenated with, for example, a chlorinating agent such as thionyl chloride into a 2-halogenomethylpyridine derivative represented by the general formula (III). In this halogenation, for example, chloroform or dichloromethane is used as a solvent. Further, the 2-hydroxymethylpyridine derivative (XII) is reacted with an active sulfonyl chloride such as methanesulfonyl chloride to obtain a sulfonyloxy derivative represented by the general formula (III). In this reaction, for example, chloroform, dichloromethane, ether, tetrahydrofuran, pyridine or benzene is used as a solvent.

Alternatively, the compound represented by the general formula (X) to be used in the above process can be prepared by the following process:

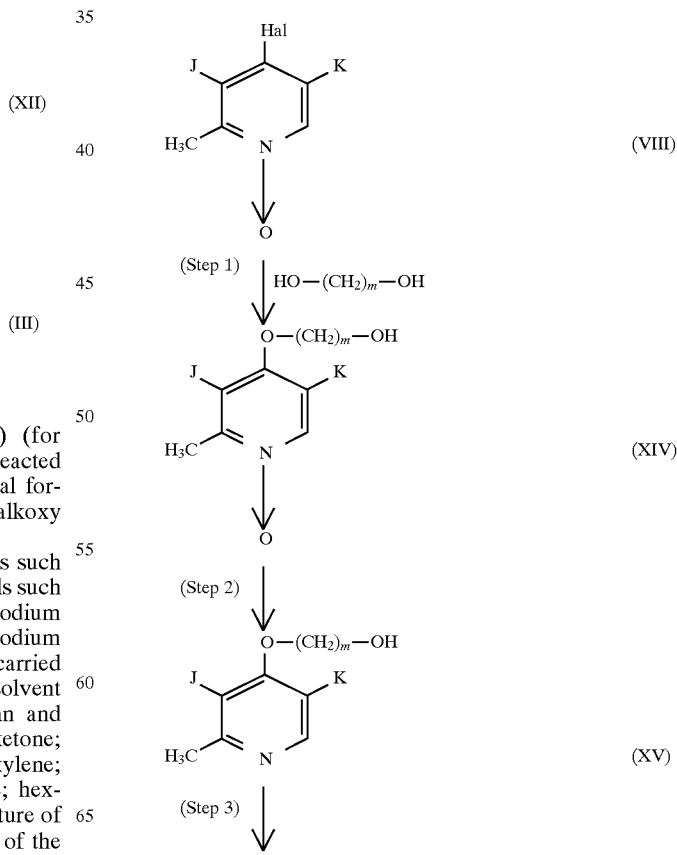

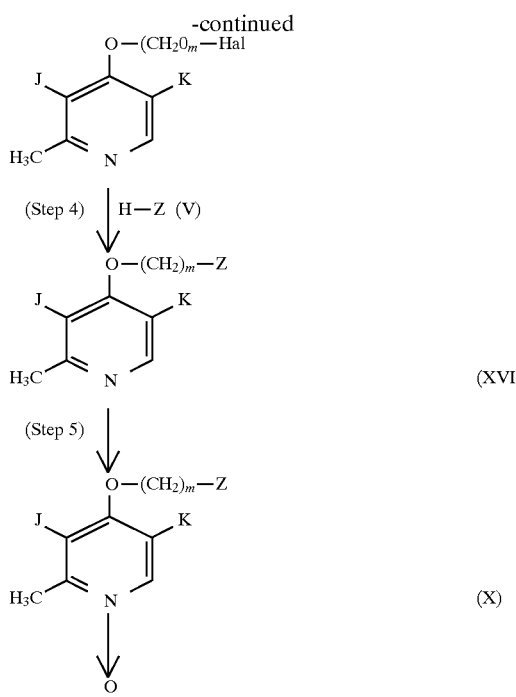

(Step 1)

A compound represented by the general formula (VIII), wherein Hal stands for a halogen atom such as chlorine atom, is condensed with a compound represented by the general formula (XIII) according to an ordinary process to obtain a compound represented by the general formula (XIV).

This condensation is preferably carried out in the presence of a base selected from among alkali metal hydrides such as sodium hydride and potassium hydride; alkali metals such as metallic sodium; alkali metal hydroxides such as sodium hydroxide and potassium hydroxide and the like.

The condensation is carried out either in the absence of any solvent or in a solvent selected from among ethers such as tetrahydrofuran and dioxane; ketones such as acetone and methyl ethyl ketone; benzene homologues such as benzene, toluene and xylene; acetonitrile; dimethylformamide; dimethyl sulfoxide; hexamethylphosphoric triamide and the like at a temperature suitably selected from the range of one under cooling with ice to the boiling point of the solvent used.

(Step 2)

The obtained alkoxy derivative (XIV) is reduced into the compound (XV). Precisely, the alkoxy derivative (XIV) is hydrogenated in the presence of a 10% palladium/carbon catalyst in an acetic anhydride/acetic acid mixture to obtain the reduction product (XV).

(Step 3)

The obtained compound (XV) is halogenated with, for example, a chlorinating agent such as thionyl chloride to obtain a 2-halogenoethyl derivative represented by the general formula (XVI). In this halogenation, for example, chloroform or dichloromethane is used as a solvent.

(Step 4)

The obtained compound (XVI) is reacted with an alcohol, thiol or amine represented by the general formula (V) to obtain a compound represented by the general formula (XVII). This reaction is preferably carried out in the presence of an acid scavenger as in the reaction of the Preparation process B.

(Step 5)

The obtained compound (XVII) is oxidized with an oxidizing agent such as hydrogen peroxide, peracetic acid or m-chloroperbenzoic acid to obtain the corresponding N-oxide derivative.

Alternatively, the compound represented by the general formula (III) to be used in the Preparation process A as a starting material can be prepared by the following process:

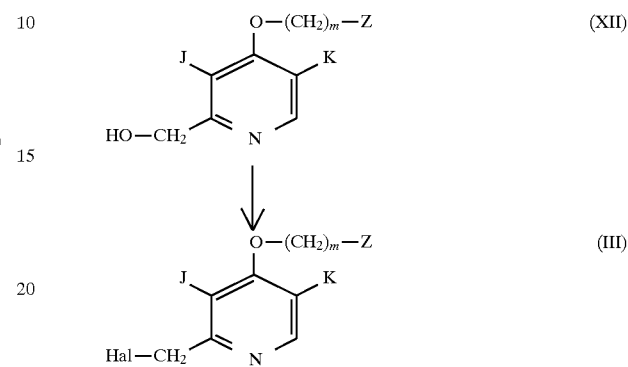

wherein Hal stands for a halogen atom and Z and m are as defined above.

A compound represented by the general formula (XII) is halogenated with, for example, a chlorinating agent such as thionyl chloride at a temperature of 0° C. to a room temperature to obtain a halogenomethylpyridine derivative represented by the general formula (III). In this halogenation, for example, chloroform or dichloromethane is used as a solvent.

The compound (IV) to be used in the Preparation process B as a starting material can be prepared by, for example, the following process:

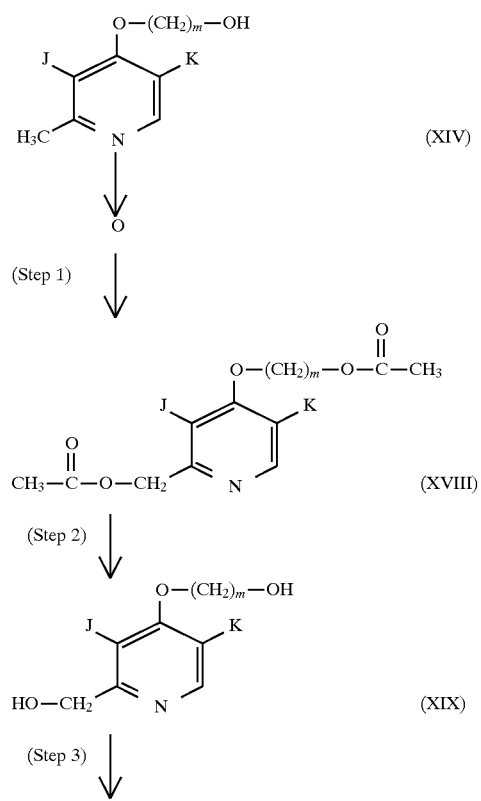

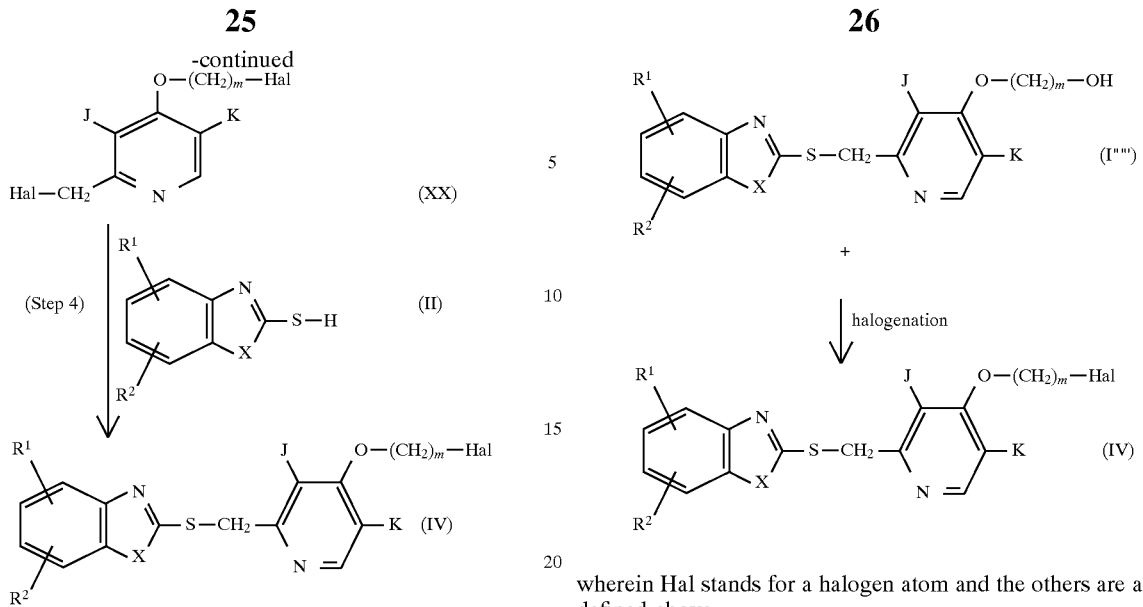

wherein Hal stands for a halogen atom and the others are as defined above.

(Step 1)

A compound represented by the general formula (XIV) is converted into the corresponding acetylate (XVIII) according to an ordinary process. For example, acetic anhydride or acetyl chloride is used in this reaction.

(Step 2)

The obtained acetylate is hydrolyzed in the presence of an acid or a base to obtain the corresponding diol derivative (XIX).

(Step 3)

The diol derivative (XIX) is halogenated with, for example, a chlorinating agent such as thionyl chloride to obtain a dihalide represented by the general formula (XX). In this halogenation, for example, chloroform or dichloromethane is used as a solvent.

(Step 4)

The obtained dihalide (XX) is reacted with a compound represented by the general formula (II) to obtain a sulfide derivative represented by the general formula (IV).

This reaction is carried out in the presence of an acid scavenger selected from among carbonates and hydrogencarbonates of alkali metals, such as potassium carbonate and sodium carbonate, and alkali hydroxides such as sodium hydroxide and potassium hydroxide. Examples of the solvent to be used in the reaction include alcohols such as ethanol and methanol, tetrahydrofuran, dioxane, dimethylformamide, dimethyl sulfoxide and mixtures thereof with water. The reaction temperature may be from 0° C. to the boiling point of the solvent used, preferably from about 40° to 60° C.

Alternatively, the compound (IV) to be used in the Preparation process B as a starting material can be prepared by the following process:

wherein Hal stands for a halogen atom and the others are as defined above.

That is, the compound (IV) can be obtained by halogenating the compound (I'''') which is an objective compound of the present invention and prepared by the Preparation process A according to an ordinary process. More precisely, a compound represented by the general formula (I'''') is halogenated with, for example, a chlorinating agent such as thionyl chloride to obtain a halide represented by the general formula (IV). In this halogenation, chloroform or dichloromethane is preferably used as a solvent and the reaction temperature ranges preferably from a room temperature to about 80° C.

Examples of the present invention will now be described, though it is needless to say that the present invention is not limited by them at all.

The following Preparative Examples refer to the preparation of raw materials to be used in the preparation of the objective compounds according to the present invention.

PREPARATIVE EXAMPLE 1

Synthesis of 4-(2-benzyloxyethoxy)-2,3-dimethylpyridine N-oxide

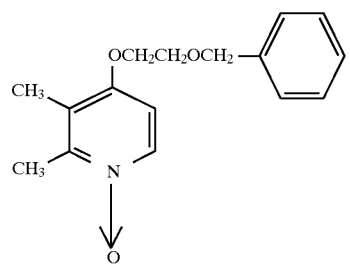

1.82 g (79.13 mmol) of Na was added to 50 ml of benzyloxyethanol to obtain a mixture. This mixture was stirred at 50° C. for 2 hours. 5.0 g (31.76 mmol) of 4-chloro-2,3-dimethylpyridine N-oxide was added to the resulting mixture at a room temperature. The obtained mixture was stirred at 110° C. for 1.5 hours, cooled to a room temperature and filtered to remove insoluble matter. The filtrate was adsorbed to silica gel with dichloromethane. The silica gel was treated with 5 to 30% ethyl acetate in hexane to elute benzyloxyethanol. Then, the resulting silica gel was treated with 5 to 30% methanol in ethyl acetate to obtain 7.15 g of 4-(2-benzyloxyethoxy)-2,3-dimethylpyridine N-oxide as an oil.

$^1$H-NMR (CDCl$_3$) δ; 2.20 (s, 3H), 2.47 (s, 3H) 3.8~4.0 (m, 2H), 4.1~4.25 (m, 2H), 4.6 (s, 2H), 6.65 (d, J=7.03Hz, 1H), 7.33 (s, 5H), 8.12 (d, J=7.03Hz, 1H)

PREPARATIVE EXAMPLE 2

Synthesis of 4-(2-benzyloxyethoxy)-2-hydroxymethyl-3-methylpyridine

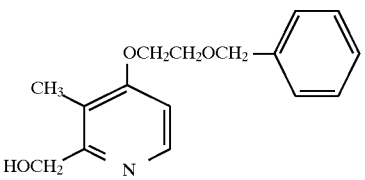

A mixture comprising 6.5 g of 4-(2-benzyloxyethoxy-2,3-dimethylpyridine N-oxide and 56 ml of acetic anhydride was stirred at 80° to 90° C. for one hour and distilled to remove the acetic anhydride. The obtained residue was made weakly basic with an aqueous solution of sodium carbonate and extracted with methyl ethyl ketone. The extract was dried over magnesium sulfate and distilled to remove the methyl ethyl ketone. Thus, 7.0 g of 2-acetoxymethyl-4-(2-benzyloxyethoxy)- 3-methylpyridine was obtained. This intermediate was dissolved in 90 ml of ethanol, followed by the addition of 1.43 g of sodium hydroxide. The obtained mixture was stirred at 40° C. for one hour, followed by the addition of water. The mixture was extracted with methyl ethyl ketone. The obtained extract was dried over magnesium sulfate to obtain 5.4 g of 4-(2-benzyloxyethoxy)-2-hydroxymethyl-3-methylpyridine.

$^1$H-NMR (CDCl$_3$) δ; 2.06 (s, 3H) 3.7~3.95 (m, 2H), 4.0~4.3 (m, 2H), 4.6 (s, 4H), 6.70 (d, J=6.7Hz, 1H), 7.33 (s, 5H), 8.27 (d, J=6.7 Hz, 1H)

PREPARATIVE EXAMPLE 3

Synthesis of 4-(2-benzyloxyethoxy)-2-chloromethyl-3-methylpyridine

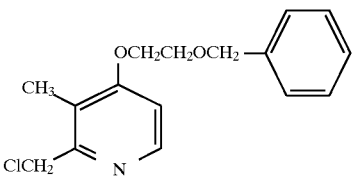

5.3 g of 4-(2-benzyloxyethoxy)-2-hydroxymethyl-3-methylpyridine was dissolved in 60 ml of chloroform to obtain a solution. A solution of 5.8 g of thionyl chloride in 40 ml of chloroform was dropwise added to the above solution under cooling with ice. The obtained mixture was stirred at a room temperature for 7 hours and distilled under a reduced pressure to obtain a residue. 200 ml of a 2N aqueous solution of sodium carbonate was added to the residue. The obtained mixture was extracted with chloroform and the extract was dried over magnesium sulfate and distilled to remove the chloroform. 6.3 g of the title compound was obtained.

$^1$H-NMR (CDCl$_3$) δ; 2.27 (s, 3H), 3.5~4.25(m, 4H), 4.56 (s, 2H), 4.66 (s, 2H), 6.7 (d, J=5.71Hz, 1H), 7.30(s, 5H), 8.27 (d, J=5.71Hz, 1H)

EXAMPLE 1

2-[{4-(2-Benzyloxyethoxy)-3-methylpyridine-2-yl}methylthio]benzimidazole

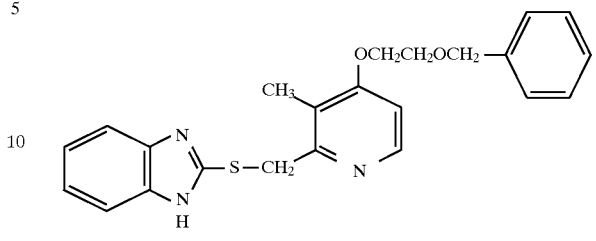

A mixture comprising 1.0 g of 2-mercaptobenzimidazole, 2.0 g of 4-(2-benzyloxyethoxy)-2-chloromethyl-3-methylpyridine, 302 mg of sodium hydroxide and 40 ml of ethanol was stirred under heating at 60° C. for 1.5 hours and distilled under a reduced pressure to remove the ethanol. The obtained residue was subjected to silica gel column chromatography. The column was treated with 30 to 60% ethyl acetate in n-hexane to obtain 2.0 g of the title compound as a white crystal.

$^1$H-NMR (CDCl$_3$) δ; 2.28 (s, 3H), 3.8~3.9 (m, 2H), 4.15~4.25(m,2H), 4.37(s, 2H), 4.62 (s, 2H), 6.74 (d, J=5.71Hz, 1H), 7.11~7.65 (m, 9H), 8.32 (d, J=5.71Hz, 1H)

EXAMPLE 2

2-[{4-(2-Benzyloxyethoxy)-3-methylpyridine-2-yl}methylsulfinyl]benzimidazole

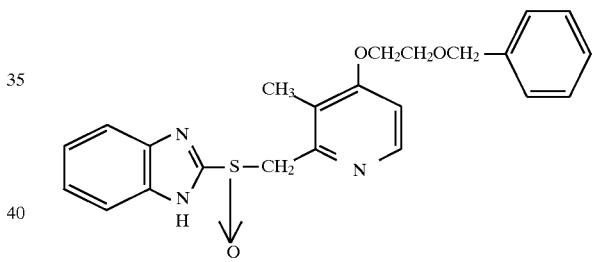

0.98 g of the thio ether prepared above was dissolved in 40 ml of dichloromethane to obtain a solution. 521 mg of m-chloroperbenzoic acid was added to the solution in portions at a temperature of −30° to −40° C., followed by the addition of 461 mg of triethylamine. The obtained mixture was heated to 0° C., followed by the addition of 20 ml of a 1N aqueous solution of sodium carbonate. The obtained mixture was stirred for 30 minutes and extracted with dichloromethane. The extract was washed with a saturated aqueous solution of common salt, dried over magnesium sulfate and distilled to remove the dichloromethane. The obtained residue was crystallized from a dichloromethane/ether mixture to obtain 0.78 g of the title compound as a crystal.

M$^{+1}$ (determined according to PAB mass spectrometry: the same applies hereinafter): 422

$^1$H-NMR (CDCl$_3$) δ; 2.2 (s, 3H), 3.65~3.98 (m, 2H) 4.04~4.28 (m, 2H), 4.59 (s, 2H), 4.78 (s, 2H), 6.98 (d, J=4.6Hz, 1H), 7.05~7.8(m, 9H) 8.22 (d, J=4.6Hz, 1H), 13.6 (bs, 1H)

EXAMPLES 3 TO 5

The following compounds were prepared in a similar manner to that described in Example 1 or 2.

EXAMPLE 3

2-[{4-(2-Benzyloxyethoxy)-3-methylpyridine-2-yl}methylsulfinyl]-5-methoxy-1H-benzimidazole

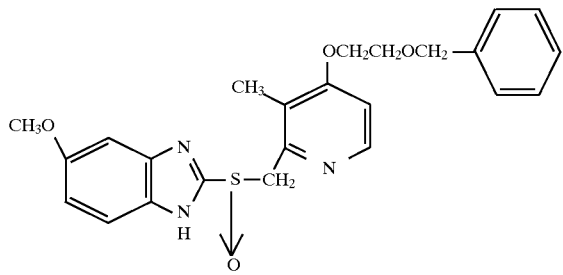

¹H-NMR (CDCl₃) δ; 2.13 (s, 3H) 3.78 (s, 3H), 3.62~3.90 (m, 2H), 4.1~4.3 (m, 2H), 4.5 (s, 2H), 4.7 (s, 2H), 6.75~7.12 (m, 3H), 7.23 (s, 5H), 7.48 (d, J=9 Hz, 1H), 8.14 (d, J=7.9Hz, 1H).

EXAMPLE 4

2-[{4-(2-Benzyloxyethoxy)-3-methylpyridine-2-yl}methylsulfinyl]-5-trifluoromethyl-1H-benzimidazole

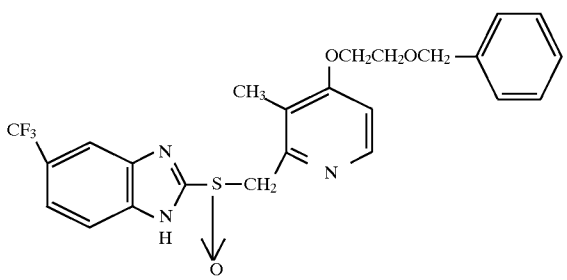

¹H-NMR (CDCl₃) δ; 2.18 (s, 3H), 3.7~3.92 (m, 2H), 4.1~4.34 (m, 2H), 4.58 (s, 2H), 4.78 (s, 2H) 6.94 (d, J=5.71Hz, 1H), 7.32 (s, 5H), 7.59 (d, J=8.79Hz, 1H), 7.83 (d, J=8.79Hz, 1H), 7.99 (s, 1H), 8.17 (d, J=5.71Hz, 1H)

EXAMPLE 5

2-[{4-(2-(2-Methoxyethoxy))ethoxy-3-methylpyridine-2-yl}methylsulfinyl]-5-trifluoromethyl-1H-benzimidazole

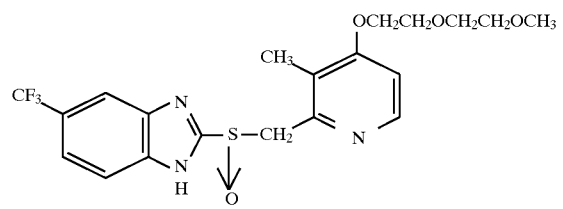

¹H-NMR (CDCl₃) δ; 2.19 (s,3H), 3.38 (s, 3H), 3.4~4.3 (m, 8H), 4.78 (ABq, J=13.6Hz, Δv=12.5Hz, 2H), 6.72 (d, J=5.62Hz, 1H) 7.49 (d, J=9Hz, 1H), 7.64 (d, J=9Hz, 1H), 8.02 (bs, 1H), 8.26 (d, J=5.62Hz, 1H)

EXAMPLE 6

Sodium Salt of 2-[{4-(2-(2-methoxyethoxy))ethoxy-3-methylpyridine-2-yl}methylsulfinyl]-1H-benzimidazole

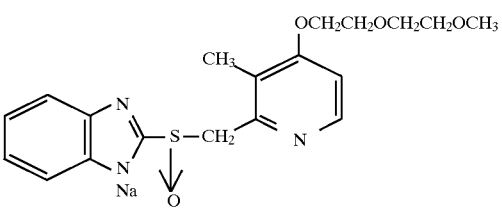

0.45 g of 2[{4-(2-(2-methoxyethoxy))ethoxy-3-methylpyridine-2-yl}methylthio]benzimidazole was dissolved in 40 ml of dichloromethane to obtain a solution. 0.22 g of m-chloroperbenzoic acid was added to this solution in portions at −40° C., followed by the addition of 0.16 g of triethylamine. The obtained mixture was heated to 0° C., followed by the addition of 20 ml of a 1N aqueous solution of sodium hydrogencarbonate. The obtained mixture was stirred for 30 minutes and extracted with dichloromethane. The extract was dried over magnesium sulfate and distilled to remove the dichloromethane. 12.1 ml of a 0.1N aqueous solution of sodium hydroxide was added to the obtained residue. The obtained mixture was stirred at a room temperature for one hour, followed by the addition of absolute ethanol. The obtained mixture was evaporated under a reduced pressure to dryness. The obtained residue was crystallized from an ethanol/ether mixture to obtain 0.42 g of the title sodium salt.

¹H-NMR (DMSO-d₆) δ; 2.16(s, 3H), 3.25(s, 3H), 3.3~3.9 (m, 6H), 4.0~4.14(m,2H), 4.55 (ABq, J=13.18Hz, Δv=13.55Hz, 2H), 6.8~6.9 (m, 3H), 7.4~7.5 (dd, J=6.15Hz, 3.08Hz, 2H), 8.28 (d, J=5.27Hz, 1H)

EXAMPLES 7 to 10

The following compounds were prepared in a similar manner to that described in Example 6.

EXAMPLE 7

Sodium Salt of 5-methoxy-2-[{4-(2-(2-methoxyethoxy))ethoxy-3-methylpyridine-2-yl}methylsulfinyl]-1H-benzimidazole

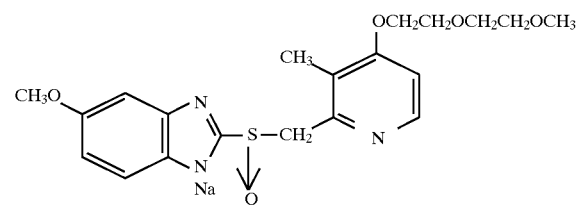

¹H-NMR (CD₃OD) δ; 2.14 (s, 3H), 3.34 (s, 3H), 3.6 (m, 4H), 3.84 (s, 5H), 4.18 (m, 2H), 6.76 (dd, J=9.36Hz, 2.52Hz, 1H), 6.9 (d, J=5.76Hz, 1H), 7.14 (d, J=2.52Hz, 1H), 7.5 (d, J=9.36Hz, 1H), 8.26 (d, J=5.76Hz, 1H)

EXAMPLE 8

Sodium Salt of 2-[{4-(2-(2-benzyloxyethoxy))ethoxy-3-methylpyridine-2-yl}methylsulfinyl]-1H-benzimidazole

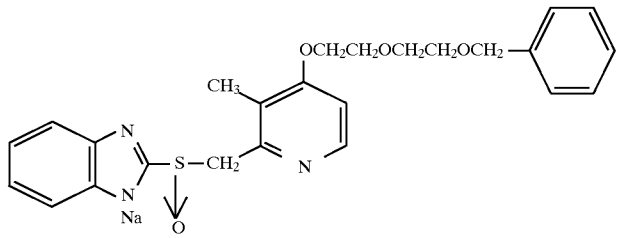

$^1$H-NMR (DMSO-$d_6$) δ; 2.16 (s, 3H), 3.4~3.9 (m, 6H), 3.96~4.28 (m,2H), 4.49 (s,2H), 4.6 (ABq, J=12.6Hz, Δν=12.85 Hz, 2H), 6.8~7.2 (m, 3H), 7.29 (s, 5H), 7.5(dd, J=6.16Hz, 3.08Hz, 2H), 8.25 (d, J=5.71Hz, 1H)

EXAMPLE 9

Sodium Salt of 2-[{4-(2-(2-benzyloxyethoxy))ethoxy-3-methylpyridine-2-yl}methylsulfinyl]-5-methoxybenzimidazole

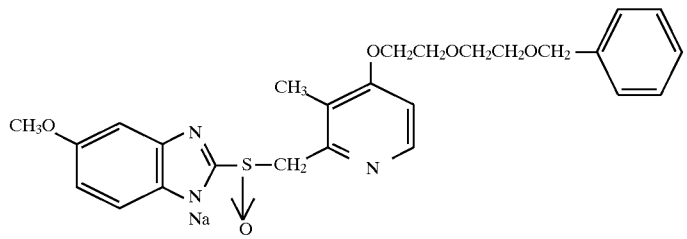

$^1$H-NMR (DMSO-$d_6$) δ; 2.16 (s, 3H), 3.63 (m, 4H), 3.74 (s, 3H), 3.85 (m, 2H), 4.18 (m, 2H), 4.49 (s, 2H), 4.55 (ABq, J=13.18Hz, Δν=13.55Hz, 2H), 6.6 (dd, J=9.35Hz, 3.20 Hz, 1H), 7.03 (d, J=2.63Hz, 1H), 6.89 (d, J=5.72Hz, 1H), 8.26 (d, J=5.72Hz, 1H)

EXAMPLE 10

Sodium Salt of 2-[{4-(2-(2-benzyloxyethoxy))ethoxy-3-methylpyridine-2-yl}methylsulfinyl]-5-trifluoromethylbenzimidazole

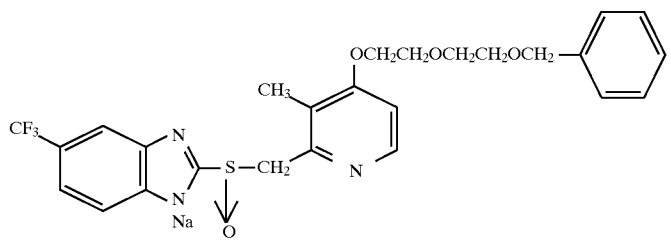

$^1$H-NMR (DMSO-$d_6$) δ; 2.16 (s, 3H), 3.62 (m, 4H), 3.79 (m, 2H), 4.19 (m, 2H), 4.48 (s, 2H), 4.57 (ABq, J=13.18Hz, Δν=12.29Hz, 2H), 6.93 (d, J=5.71Hz, 1H), 7.16 (dd, J=8.35Hz, 1.75Hz, 1H), 7.29 (s, 5H), 7.62 (d, J=8.35 Hz, 1H), 7.83 (s, 1H), 8.28 (d, J=5.71 Hz, 1H)

PREPARATIVE EXAMPLE 4

4-(2-Hydroxyethoxy)-2,3-dimethylpyridine N-oxide

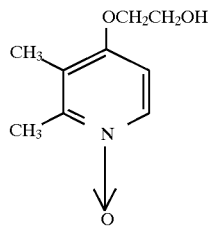

4.60 g (0.2 mol) of metallic sodium was dissolved in 80 ml of ethylene glycol under cooling with ice to obtain a solution. This solution was stirred in a nitrogen atmosphere at 100° C. for one hour, followed by the addition of 15.76 g (0.1 mol) of 4-chloro-2,3-dimethylpyridine N-oxide at a room temperature. The obtained mixture was stirred at 120° C. for 2 hours. After the completion of the reaction, the reaction mixture was distilled to dryness to remove the ethylene glycol. The obtained residue was purified by silica gel column chromatography (solvent: chloroform/methanol 19:1) to obtain 13.28 g of 4-(2-hydroxyethoxy)-2,3-dimethylpyridine N-oxide as a white crystal.

$^1$H-NMR (CD$_3$OD) δ; 2.29 (s, 3H), 2.55 (s, 3H), 3.93 (t, 2H), 4.20 (t, 2H) 7.04 (d, H), 8.18 (d, H)

PREPARATIVE EXAMPLE 5

4-(2-Chloroethoxy)-2,3-dimethylpyridine N-oxide

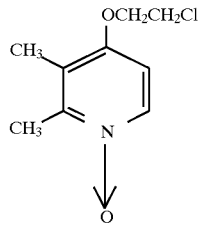

1.0 ml of thionyl chloride was gradually added to a solution of 0.92 g (5 mmol) of 4-(2-hydroxyethoxy)-2,3-dimethylpyridine N-oxide in 10 ml of chloroform under cooling with ice. The obtained mixture was heated under reflux for 2 hours, cooled by allowing to stand, neutralized with a saturated aqueous solution of sodium hydrogencarbonate and extracted with 100 ml of methyl ethyl ketone twice. The extract was dried over magnesium sulfate and filtered. The filtrate was concentrated and purified by silica gel column chromatography (solvnet: chloroform/methanol=19:1) to obtain 0.56 g of 4-(2-chloroethoxy)-2,3-dimethylpyridine N-oxide as a colorless crystal.

$^1$H-NMR (CDCl$_3$) δ; 2.24 (s, 3H), 2.54 (s, 3H), 3.86 (t, 2H), 4.28 (t, 2H), 6.62 (d, H), 8.17 (d, H)

PREPARATIVE EXAMPLE 6

2,3-Dimethyl-4-(2-succinimidoethoxy)pyridine N-oxide

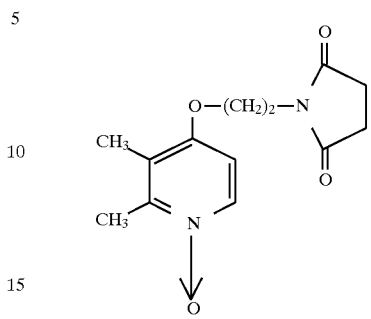

A mixture comprising 0.40 g (2 mmol) of 4-(2-chloroethoxy)-2,3-dimethylpyridine N-oxide, 0.30 g (3 mmol) of succinimide, 0.48 g (3.5 mmol) of potassium carbonate and 30 ml of methyl ethyl ketone was heated under reflux for 2 hours, cooled by allowing to stand and filtered. The filtrate was evaporated to dryness to remove the methyl ethyl ketone. The obtained residue was purified by silica gel column chromatography (solvent: CHCl$_3$/MeOH= 19:1) to obtain 0.12 g of 2,3-dimethyl-4-(2-succinimidoethoxy)pyridine N-oxide as a white crystal.

$^1$H-NMR (CDCl$_3$) δ; 2.12 (s, 3H), 2.49 (s, 3H), 2.73 (s, 4H) 3.80~4.25 (m, 4) 6.51 (d, H) 8.03 (d, H)

PREPARATIVE EXAMPLE 7

2-Chloromethyl-3-methyl-4-(2-succinimidoethoxy)pyridine

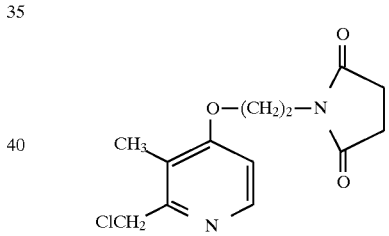

0.12 g of 2,3-dimethyl-4-(2-succinimidoethoxy)pyridine N-oxide was dissolved in 5 ml of acetic anhydride to obtain a solution. This solution was stirred at 100° C. for 0.5 hour and cooled, followed by the addition of 30 ml of ethanol. The obtained mixture was stirred at a room temperature for 0.5 hour and distilled to remove the solvent. Thus, 0.14 g of crude 2-acetoxymethyl-3-methyl-4-(2-succinimidoethoxy) pyridine was obtained as an oil.

$^1$H-NMR (CDCl$_3$) δ; 2.10 (s, 3H), 2.14 (s, 3H), 2.72 (s, 4H), 3.72–4.24 (m, 4H), 5.15 (s, 2H), 6.61 (d, H), 8.24 (d, H)

This acetoxymethyl derivative was dissolved as such in 5 ml of 1N HCl to obtain a solution. This solution was stirred at 100° C. for 0.5 hour, cooled, neutralized with a saturated aqueous solution of sodium hydrogencarbonate and extracted with 100 ml of chloroform twice. The obtained extract was dried over magnesium sulfate and filtered. The filtrate was concentrated to obtain 0.12 g of crude 2-hydroxymethyl-3-methyl-4-(2-succinimidoethoxy) pyridine as a colorless crystal.

$^1$H-NMR (CDCl$_3$) δ; 1.93 (s, 3H), 2.68 (s, 4H), 3.80~4.22 (m, 4H), 4.56 (s, 2H), 6.59 (d, H) 8.21 (d, H)

This crude hydroxymethyl derivative was dissolved as such in 5 ml of chloroform to obtain a solution. 0.11 g of thionyl chloride was dropwise added to this solution under cooling with ice. The obtained mixture was heated under reflux for 0.5 hour, cooled, neturalized with a saturated aqueous solution of sodium hydrogencarbonate and extracted with 100 ml of chloroform twice. The obtained extract was dried over magnesium sulfate and filtered. The filtrate was concentrated and dried in a vacuum to obtain 0.07 g of 2-chloromethyl-3-methyl-4-(2-succinimidoethoxy)pyridine as a white semicrystal.

$^1$H-NMR (CDCl$_3$) δ; 2.15 (s, 3H), 2.68 (s, 4H), 3.80~4.20 (m, 4H), 4.60 (s, 2H), 6.61 (d, H), 8.22 (d, H)

EXAMPLE 11

2-[{3-Methyl-4-(2-succinimidoethoxy)-pyridine-2-yl}methylthio]-1H-benzimidazole

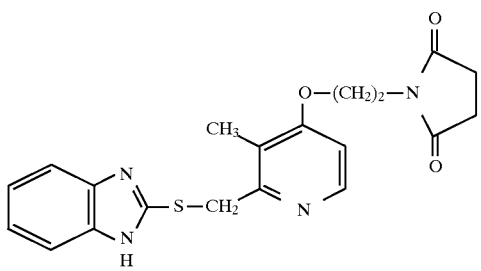

A mixture comprising 0.03 g (0.18 mmol) of 2-mercapto-1H-benzimidazole, 0.06 g (0.21 mmol) of 2-chloromethyl-3-methyl-4-(2-succinimidoethoxy)pyridine, 0.03 g (0.21 mmol) of potassium carbonate and 10 ml of methyl ethyl ketone was heated under reflux in a nitrogen atmosphere for 3 hours, cooled and filtered. The filtrate was concentrated and dried in a vacuum, followed by the addition of water. The obtained mixture was extracted with 50 ml of chloroform thrice. The extract was dried over magnesium sulfate and filtered. The filtrate was concentrated and purified by silica gel column chromatography to obtain 0.08 g of 2-[{3-methyl-4-(2-succinimidoethoxy)pyridine-2-yl}methylthio]-1H-benzimidazole as a white crystal.

$^1$H-NMR (CDCl$_3$) δ; 2.09 (s, 3H), 2.63 (s, 4H) 3.72~4.16 (m, 4H), 4.27 (s, 2H), 6.53 (d, H) 6.90~7.50 (m, 4H), 8.18 (d, H)

EXAMPLE 12

2-[{3-Methyl-4-(2-succinimidoethoxy)pyridine-2-yl}methylsulfinyl]-1H-benzimidazole

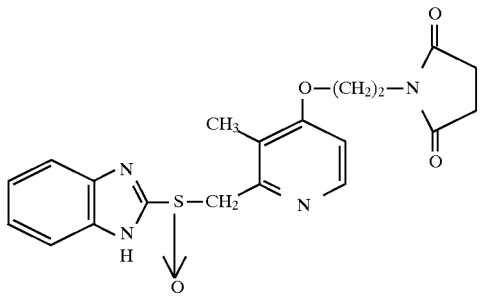

0.18 g of 95% m-chloroperbenzoic acid was gradually added to a solution of 0.40 g (1 mmol) of 2-[{3-methyl-4-(2-succinimidoethoxy)pyridine-2-}ylmethylthio]-1H-benzimidazole in 20 ml of dichloromethane at −60° C. to obtain a mixture. This mixture was stirred for 0.5 hour, followed by the addition of 0.15 g of triethylamine. The obtained mixture was heated to −10° C., followed by the addition of 30 ml of a saturated aqueous solution of sodium hydrogencarbonate. The obtained mixture was stirred for 0.5 hour and extracted with 50 ml of dichloromethane twice. The extract was dried over magnesium sulfate and filtered. The filtrate was concentrated and dried in a vacuum to obtain a crude product. This crude product was crystallized from dichloromethane/diethyl ether to obtain 0.36 g of 2-[{3-methyl-4-(2-succinimidoethoxy)pyridine-2-yl}methylsufinyl]-1H-benzimidazole as a white crystal.

$^1$H-NMR (CDCl$_3$) δ; 2.12 (s, 3H), 2.73 (s, 4H), 3.83~4.29 (m, 4H), 4.56~4.92 (m, 2H), 6.65 (d, H), 7.17~7.72 (m, 4H), 8.25 (d, H)

EXAMPLE 13

5-Methoxy-2-[{3-methyl-4-(2-succinimidoethoxy)pyridine-2-yl}methylthio]-1H-benzimidazole

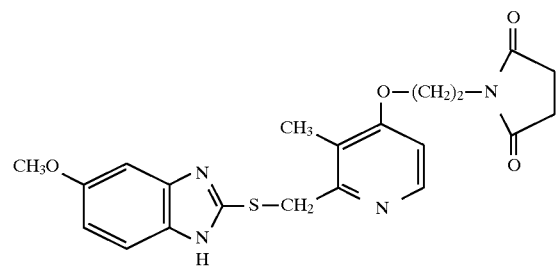

The title compound was prepared in a similar manner to that described in Example 11.

$^1$H-NMR (CDCl$_3$) δ; 2.20 (s, 3H), 2.74 (s, 4H), 3.84 (s, 3H), 3.88~4.38 (m, 4H), 4.35 (s, 2H), 6.71 (d, H), 6.80~7.48 (m, 3H), 8.35 (d, H)

EXAMPLE 14

2-[{3-Methyl-4-(2-succinimidoethoxy)pyridine-2-yl}-methylthio]-5-trifluoromethyl-1H-benzimidazole

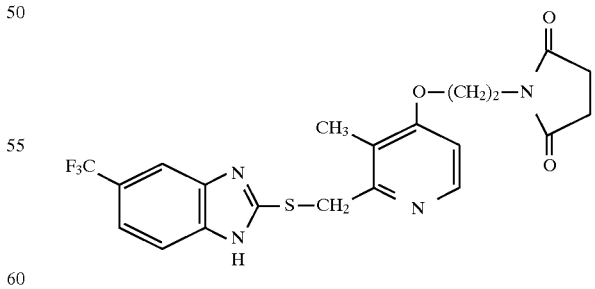

The title compound was prepared in a similar manner to that described in Example 11.

$^1$H-NMR (CDCl$_3$) δ; 2.22 (s, 3H), 2.75 (s, 4H), 3.88~4.08 (m, 2H), 4.08~4.28 (m, 2H), 4.45 (s, 2H), 6.73 (d, H), 7.32~7.86 (m, 3H), 8.32 (d, H)

EXAMPLE 15

5-Methoxy-2-[{3-methyl-4-(2-succinimidoethoxy)pyridine-2-yl}methylsulfinyl]-1H-benzimidazole

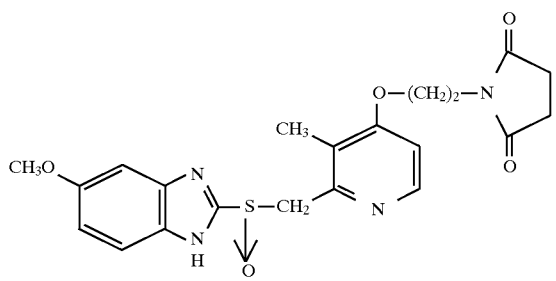

The title compound was prepared in a similar manner to that described in Example 12.

$^1$H-NMR (CDCl$_3$) δ; 2.13 (s, 3H) 2.74 (s, H), 3.86 (s,3H), 3.60~4.30 (m, 4H), 4.50~4.90 (m, 2H), 6.65 (d, H), 6.80~7.68 (m, 3H), 8.25 (d, H)

EXAMPLE 16

2-[{3-Methyl-4-(2-succinimidoethoxy)pyridine-2-yl}methylsulfinyl]- 1H-5-trifluoromethylbenzimidazole

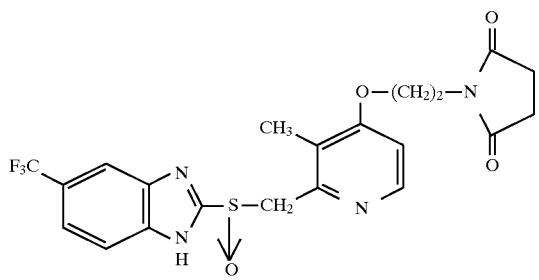

The title compound was prepared in a similar manner to that described in Example 12.

$^1$H-NMR (CDCl$_3$) δ; 2.23 (s, 3H), 2.75 (s, 4H), 3.80~4.45 (m, 4H), 4.67 (m, 2H), 6.74 (d, H), 7.30~8.00 (m, 3H), 8.37 (d, H)

PREPARATIVE EXAMPLE 8

2,3-Dimethyl-4-(2-pyridylmethoxyethoxy)pyridine N-oxide

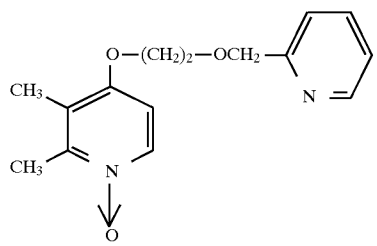

0.39 g of 60% sodium hydride was added to a suspension of 1.20 g (6.5 mmol) of 4-(2-hydroxyethoxy)- 2,3-dimethylpyridine N-oxide in 40 ml of tetrahydrofuran under cooling with ice in a nitrogen atmosphere to obtain a mixture. This mixture was stirred for 0.5 hour, followed by the addition of 0.83 g (6.5 mmol) of 2-chloromethylpyridine. The obtained mixture was treated under reflux for 8 hours, cooled and filtered. The filtrate was concentrated and purified by silica gel column chromatography (solvent: ethyl acetate/n-hexane=4:1~CHCl$_3$/MeOH= 19:1) to obtain 0.61 g of 2,3-dimethyl-4-(2-pyridylmethoxyethoxy)pyridine N-oxide.

$^1$H-NMR (CDCl$_3$) δ; 2.20 (s, 3H), 2.50 (s, 3H), 3.80~4.04 (m, 2H), 4.04~4.28 (m, 2H), 4.70 (s, 2H), 6.60 (d, H), 7.00~7.74 (m, 3H), 8.04 (d, H), 8.45 (d, H)

PREPARATIVE EXAMPLE 9

2-Hydroxymethyl-3-methyl-4-(2-pyridylmethoxyethoxy)pyridine

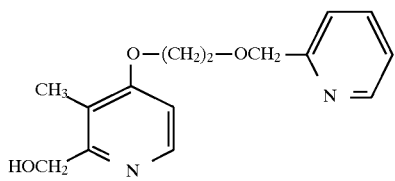

A mixture comprising 0.60 g of 2,3-dimethyl-4-(2-pyridylmethoxyethoxy)pyridine N-oxide and acetic anhydride was stirred at 100° C. for 0.5 hour and cooled, followed by the addition of 40 ml of ethanol. The obtained mixture was stirred at a room temperature for 0.5 hour and distilled to remove the solvent. The residue was dried in a vacuum to obtain 0.47 g of crude 2-acetoxymethyl-3-methyl-4-(2-pyridylmethoxyethoxy)pyridine as an oil.

This crude intermediate was dissolved as such in 1N HCl to obtain a solution. This solution was stirred at 100° C. for one hour, cooled, neutralized with a saturated aqueous solution of sodium hydrogencarbonate and extracted with 50 ml of dichloromethane twice. The extract was dried over magnesium sulfate and filtered. The filtrate was concentrated and purified by silica gel column chromatography (solvent: ehtyl acetate) to obtain 0.40 g of 2-hydroxymethyl-3-methyl-4-(2-pyridylmethoxyethoxy)pyridine as a colorless semicrystal.

EXAMPLE 17

2-[{3-Methyl-4-(2-pyridylmethoxyethoxy)pyridine-2-yl}methylthio]-1H-benzimidazole

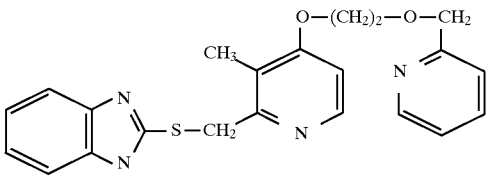

0.71 g (6 mmol) of thionyl chloride was added to a solution of 0.40 g (1.5 mmol) of 2-hydroxymethyl-3-methyl-4-(2-pyridylmethoxyethoxy)pyridine in 10 ml of chloroform under cooling with ice to obtain a mixture. This mixture was stirred at 0° C. for 2 hours. After the completion of the reaction, the mixture was neutralized with a saturated aqueous solution of sodium hydrogencarbonate and extracted with 50 ml of chloroform four times. The extract was dried over magnesium sulfate and filtered. The obtained filtrate was concentrated and dried in a vacuum to obtain 0.42 g of crude 2-chloromethyl-3-methyl-4-(2-pyridylmethoxyethoxy)pyridine as a semicrystal.

A mixture comprising 0.40 g of this crude intermediate, 0.18 g of 2-mercapto-1H-benzimidazole, 0.19 g of potassium carbonate and 30 ml of methyl ethyl ketone was heated under reflux in a nitrogen atmosphere for 2 hours, cooled and filtered. The filtrate was concentrated and purified by silica gel column chromatography (solvent: ethyl acetate/n-hexane) to obtain 0.38 g of 2-[{3-methyl-4-(2-pyridylmethoxyethoxy)pyridine-2-yl}methylthio]-1H-benzimidazole as a colorless oil.

$^1$H-NMR (CDCl$_3$) δ; 2.26 (s, 3H), 3.80~4.04 (m, 2H), 4.10~4.28 (m, 2H), 4.35 (s, 2H), 4.70 (s, 2H), 6.70 (d, H), 6.94~7.20 (m, 7H), 8.25 (d, H), 8.45 (d, H)

EXAMPLE 18

2-[{3-Methyl-4-(2-pyridylmethoxyethoxy)pyridine-2-yl}-methylfulfinyl]-1H-benzimidazole

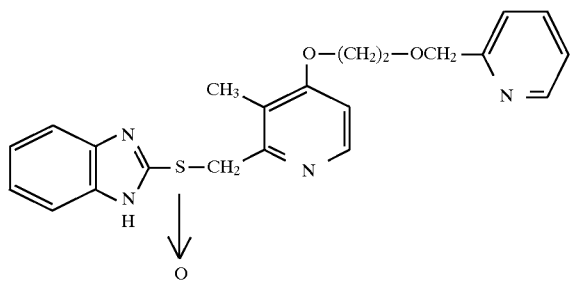

0.16 g of m-chloroperbenzoic acid was added to a solution of 0.38 g of 2-[{3-methyl-4-(2-pyridylmethoxyethoxy)pyridine-2-yl}methylthiol]-1H-benzimidazole in 20 ml of dichloromethane at −60° C. in a nitrogen atmosphere to obtain a mixture. This mixture was stirred for 0.5 hour. After the completion of the reaction, 0.16 g of triethylamine was added to the reaction mixture. The obtained mixture was heated to −10° C., followed by the addition of 30 ml of a saturated aqueous solution of sodium hydrogencarbonate. The obtained mixture was stirred at a room temperature for 0.5 hour and extracted with 50 ml of dichloromethane thrice. The extract was dried over magnesium sulfate and filtered. The filtrate was concentrated and dried in a vacuum to obtain a crude product. This crude product was crystallized from dichloromethane/diethyl ether to obtain 0.31 g of 2-[{3-methyl-4-(2-pyridylmethoxyethoxy)pyridine-2-yl}methylsulfinyl]-1H-benzimidazole as a white crystal.

$^1$H-NMR (CDCl$_3$) δ; 2.17 (s, 3H), 3.83~4.06 (m, 2H), 4.06~4.34 (m, 2H), 4.72 (s 2H), 4.64~4.84 (m, 2H), 6.70 (d, H), 7.04~7.80 (m, 7H), 8.27 (d, H), 8.55 (d, H)

PREPARATIVE EXAMPLE 10

2,3-Dimethyl-4-[2-(2-pyrrolidone)ethoxy]pyridine N-oxide

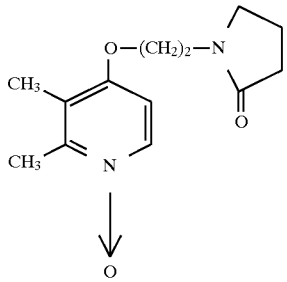

0.42 g of sodium hydride was added to 30 cc of N,N-dimethylformamide at a room temperature to obtain a mxiture. This mixture was cooled to 0° C., followed by the addition of 0.74 g of 2-pyrrolidone. The obtained mixture was stirred at 80° C. for 1.5 hours and cooled to a room temperature, followed by the addition of 1.17 g of 4-(2-chloroethoxy)-2,3-dimethylpyridine N-oxide. The obtained mixture was stirred at 60° to 80° C. for 5 hours and cooled, followed by the addition of 20 cc of a saturated aqueous solution of sodium hydrogencarbonate. The obtained mixture was extracted with chloroform. The extract was dried over magnesium sulfate and filtered. The filtrate was concentrated to obtain a crude product. This crude product was purified by silica gel column chromatography to obtain 430 mg of 2,3-dimethyl-4-[2-(2-pyrrolidone)ethoxy]pyridine N-oxide as a yellow crystal.

$^1$H-NMR (CDCl$_3$) δ; 2.2 (s, 3H), 2.54 (s, 3H), 1.9~2.5 (m, 4H), 3.57 (t, J=7Hz, 2H), 3.73 (t, J=6Hz, 2H), 4.16 (t, J=6Hz, 2H), 6.65 (d, J=7Hz, 1H), 8.15 (d, J=7Hz, 1H)

PREPARATIVE EXAMPLE 11

2-Chloromethyl-3-methyl-4-[2-(2-pyrrolidone)ethoxy]pyridine

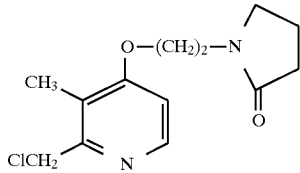

10 cc of acetic anhydride was added to 0.65 g of 2,3-dimethyl-4-[2-(2-pyrrolidone)ethoxy]pyridine N-oxide at a room temperature to obtain a mixture. This mixture was stirred at 90° C. for 2 hours, followed by the addition of ethanol. The obtained mixture was distilled under a reduced pressure to obtain 0.79 g of crude 2-acetoxymethyl-3-methyl-4-[2-(2-pyrrolidone)ethoxy]pyridine.

20 cc of 1N HCl was added to this crude intermediate to obtain a mixture. This mixture was stirred at 100° C. for 2 hours, cooled, neutralized with a saturated aqueous solution of sodium hydrogencarbonate and extracted with chloroform. The extract was dried over magnesium sulfate and filtered. The filtrate was distilled under a reduced pressure to obtain 510 mg of crude 2-hydroxymethyl-3-methyl-4-[2-(2-pyrrolidone)ethoxy]pyridine as an ocherous crystal.

$^1$H-NMR (CDCl$_3$) δ; 2.04 (s, 3H), 1.9~2.6 (m, 4H), 3.58 (t, J=7 Hz, 2H), 3.73 (t, J=6Hz, 2H), 4.2 (t, J=6Hz, 2H), 4.65 (s, 2H), 6.7 (d, J=7HZ, 1H), 8.3 (d, J=7Hz, 1H)

500 mg of this crude intermediate was dissolved in 10 ml of dichloromethane to obtain a solution. 1.19 g of thionyl chloride was dropwise added to this solution at −20° C. The obtained mixture was stirred at a room temperature for 30 minutes, neutralized with a saturated aqueous solution of sodium hydrogencarbonate and extracted with chloroform. The extract was dried over magnesium sulfate and filtered. The filtrate was distilled under a reduced pressure to obtain 0.57 mg of crude 2-chloromethyl-3-methyl-4-[2-(2-pyrrolidone)ethoxy]pyridine as an oil.

$^1$H-NMR (CDCl$_3$) δ; 2.25 (s, 3H), 1.8~2.5 (m, 4H), 3.54 (t, J=7 Hz, 2H), 3.68 (t, J=6Hz, 2H), 4.1 (t, J=6 Hz, 2H), 6.62 (d, J=6Hz, 1H), 8.22 (d, J=6Hz, 1H)

EXAMPLE 19

2-[3-Methyl-4-{2-(2-pyrrolidone)ethoxy}pyridine-2-yl]-methylthio-1H-benzimidazole

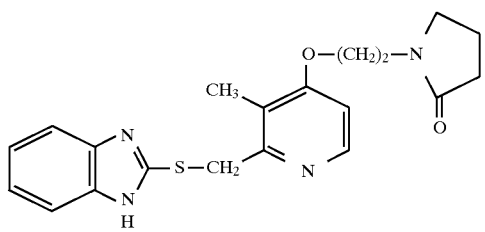

20 cc of methyl ethyl ketone was added to a mixture comprising 0.55 g of 2-chloromethyl-3-methyl-4-[2-(2-pyrrolidone)ethoxy]pyridine, 0.3 g of 2-mercapto-1H-benzimidazole and 0.33 g of potassium carbonate to obtain a mixture. This mixture was heated under reflux for 2 hours and filtered. The filtrate was concentrated to obtain a crude product. This crude product was purified by silica gel column chromatography to obtain 0.27 g of the title compound as a pale yellow crystal.

$^1$H-NMR (CDCl$_3$) δ; 2.26 (s, 3), 1.8~2.5 (m, 4H), 3.57 (t, J=7 Hz, 2H), 3.7 (t, J=6Hz, 2H), 4.13 (t, J=6Hz, 2H) 4.34 (s, 2H), 6.66 (d, J=6Hz, 1H), 7.0~7.55 (m, 4H), 8.25 (d, J=6Hz, 1H)

EXAMPLE 20

5-Methoxy-2-[3-methyl-4-{2-(2-pyrrolidone)ethoxy}-pyridine-2-yl]methylthio-1H-benzimidazole

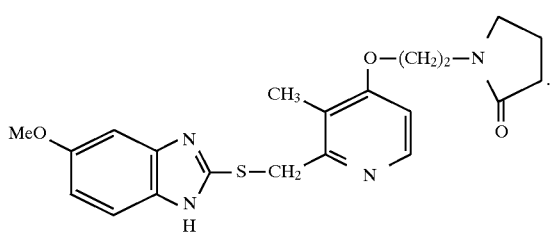

The title Compound was prepared in a similar manner to that described in Example 19.

$^1$H-NMR (CDCl$_3$) δ; 2.24(s, 3H), 1.9~2.5 (m, 4H), 3.56 (t, J=7 Hz, 2H), 3.72 (t, J=6Hz, 2H), 3.83 (s, 3H), 4.17 (t, J=6Hz, 2H), 4.4 (s, 2H), 6.6~7.5 (m, 4H), 8.35 (d, J=6Hz, 1H)

EXAMPLE 21

2-[3-Methyl-4-{2-(2-pyrrolidone)ethoxy}pyridine-2-yl]methylthio-5-trifluoromethyl-1H-benzimidazole

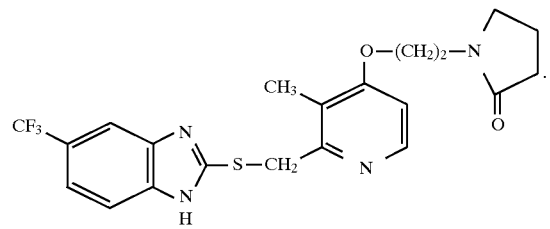

The title compound was prepared in a similar manner to that described in Example 19.

$^1$H-NMR (CDCl$_3$) δ; 2.28 (s, 3 H), 1.9~2.55 (m, 4H), 3.57 (t, J=7 Hz, 2H), 3.74 (t, J=6Hz, 2H), 4.2 (t, J=6Hz, 2H), 4.4 (s 2H), 6.77 (d, J=6Hz, 1H), 7.27~7.85 (m, 3H), 8.38 (d, J=6Hz, 1H)

EXAMPLE 22

2-[3-Methyl-4-{2-(2-pyrrolidonethoxy}pyridine-2-yl]methylsulfinyl-1H-benzimidazole

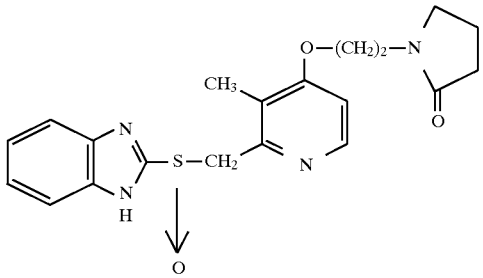

0.27 g of 2-[3-methyl-4-{2-(2-pyrrolidone (ethoxy}pyridine-2-yl]methylthio-1H-benzimidazole was dissolved in 20 ml of dichloromethane to obtain a solution. 0.12 g of 95% m-chloroperbenzoic acid was added to this solution at −60° C. The obtained mixture was stirred at −50° to −40° C. for 4 hours, followed by the addition of 0.09 g of triethylamine and a saturated aqueous solution of sodium hydrogencarbonate. The obtained mixture was extracted with dichloromethane. The extract was dried over magnesium sulfate and filtered. The filtrate was concentrated to obtain a crude product. This crude product was crystallized from dichloromethane/ether to obtain 0.18 g of the title compound.

$^1$H-NMR (CDCl$_3$) δ; 2.18 (s, 3H), 1.9~2.5 (m, 4H), 3.53 (t, J=7 Hz, 2H), 3.73 (t, J=6Hz, 2H), 4.16(t, J=6Hz, 2H), 4.74 (ABq, J=14Hz, Δv=16Hz, 2H), 6.7 (d, J=6 Hz, 1H), 7.2~7.7 (m, 4H), 8.25 (d, J=6Hz, 1H)

EXAMPLE 23

5-Methoxy-2-[3-methyl-4-{2-(2-pyrrolidone)ethoxy}pyridine-2-yl]methylsulfinyl-1H-benzimidazole

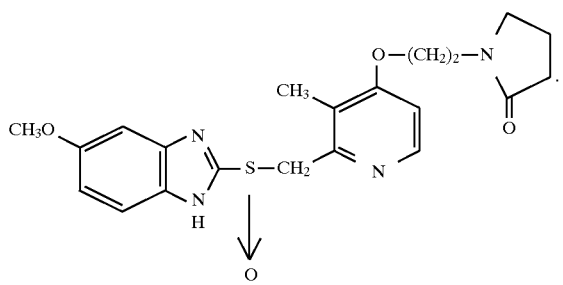

The title compound was prepared in a similar manner to that described in Example 22.

$^1$H-NMR (CDCl$_3$) δ; 2.17 (s, 3H), 1.9~2.5 (m, 4H), 3.38~3.78 (m, 4H), 3.8 (s, 3H), 4.1 (t; J=6Hz, 2H), 4.66 (ABq, J=13Hz, Δv=12.4Hz, 2H), 6.6 (d, J=6Hz, 1H), 6.77~7.6 (m, 3H), 8.17 (d, J=6Hz, 1H)

EXAMPLE 24

2-[3-Methyl-4-{2-(2-pyrrolidone)ethoxy}pyridine-2-yl]methylsulfinyl-5-trifluoromethyl-1H-benzimidazole

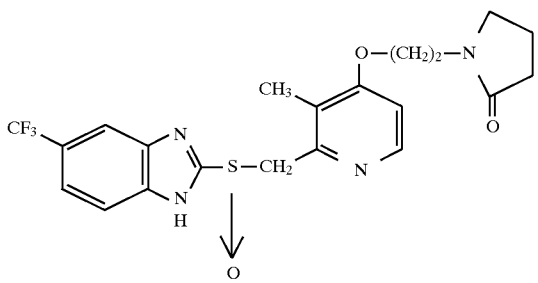

The title compound was prepared in a similar manner to that described in Example 22.

$^1$H-NMR (CDCl$_3$) δ; 2.17 (s, 3H), 1.8~2.55 (m 4H), 3.4~3.8 (m, 4H), 4.75 (ABq, J=14.3Hz, Δv=17.5Hz, 2H), 6.69 (d, J=6Hz, 1H), 7.24~8.0 (m, 3H), 8.2 (d, J=6Hz, 1H)

PREPARATIVE EXAMPLE 12

2-Chloromethyl-4-(2-hydroxyethoxy)-3-methylpyridine

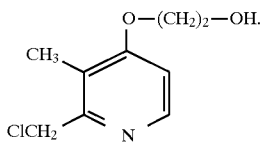

15 ml of acetic anhydride was added to 25 g of 4-(2-hydroxyethoxy)-2,3-dimethylpyridine N-oxide to obtain a solution. This solution was stirred at 90° C. for 2 hours, followed by the addition of ethanol. The obtained mixture was distilled under a reduced pressure to obtain 4-(2-acetoxyethoxy)-2-acetoxymethyl-3-methylpyridine.

20 g of sodium hydroxide, 20 ml of water and 50 ml of ethanol were added to this intermediate to obtain a mixture. This mixture was stirred at a room temperature for 10 minutes and distilled to remove the ethanol, followed by the addition of 50 ml of a saturated aqueous-solution of common salt. The obtained mixture was extracted with 2-butanone. The extract was dried over magnesium sulfate and filtered. The filtrate was distilled under a reduced pressure to obtain 20 g of 4-(2-hydroxyethoxy)-2-hydroxymethyl-3-methylpyridine.

$^1$H-NMR (CDCl$_3$) δ; 2.02 (s, 3H) 3.9~4.2 (m, 4H), 4.50 (s, 2H), 6.63 (d, J=6Hz, 1H), 8.15 (d, J=6Hz, 1H)

11.9 g of the 4-(2-hydroxyethoxy)-2-hydroxymethyl-3-methylpyridine prepared above was dissolved in 200 ml of dichloromethane to obtain a solution. 24 ml of thionyl chloride was dropwise added to this solution at 0° C. The obtained mixture was stirred at a room temperature for 2 hours and distilled under a reduced pressure to remove the dichloromethane and excess thionyl chloride. A saturated aqueous solution of sodium hydrogencarbonate was added to the residue to obtain a mixture. This mixture was extracted with chloroform. The extract was dried over magnesium sulfate and filtered. The filtrate was concentrated to obtain 10.9 g of 2-chloromethyl-4-(2-hydroxyethoxy)-3-methylpyridine.

$^1$H-NMR (CDCl$_3$) δ; 2.3 (s, 3H), 3.9~4.2 (m, 4H), 4.69 (s, 2H), 6.73 (d, J=6Hz, 1H), 8.3 (d, J=6Hz, 1H)

EXAMPLE 25

2-[4-(2-Hydroxyethoxy)-3-methylpyridine-2-yl]methylthio-5-methoxy-1H-benzimidazole

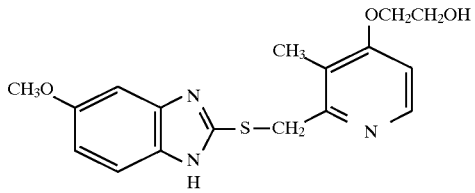

60 ml of ethanol was added to a mixture comprising 0.7 g of 2-chloromethyl-4-(2-hydroxyethoxy)-3-methylpyridine, 0.63 g of 2-mercapto-5-methoxy-1H-benzimidazole and 0.16 g of sodium hydroxide to obtain a mixture. This mixture was stirred at 60° C. for one hour, concentrated and purified by silica gel column chromatography to obtain 1.08 g of the title compound.

$^1$-NMR (DMSO-d$_6$) δ; 2.2 (s, 3H) 3.72 (s, 3H), 3.6~4.1 (m, 4H), 4.6 (s, 2H) 6.6~7.35 (m, 4H), 8.14 (d, J=6Hz, 1H)

EXAMPLE 26

2-[4-(2-Hydroxyethoxy)-3-methylpyridine-2-yl]methylthio-1H-benzimidazole

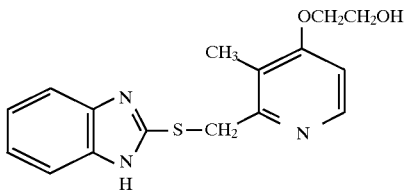

The title compound was prepared in a similar manner to that described in Example 25.

$^1$H-NMR (DMSO-d$_6$) δ; 2.24 (s, 3H), 3.6~4.18 (m, 4H), 4.7 (s, 2H), 6.93 (d, J=6Hz, 1H), 7.0~7.6 (m, 4H), 8.25 (d, J=6Hz, 1H)

EXAMPLE 27

2-[4-(2-Hydroxyethoxy)-3-methylpyridine-2-yl]methylthio-5-trifluoromethyl-1H-benzimidazole

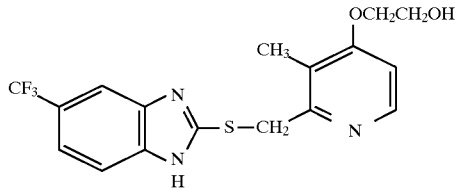

The title compound was prepared in a similar manner to that described in Example 25.

$^1$H-NMR (DMSO-d$_6$) δ; 2.25 (s, 3H), 3.6~4.2 (m 4H), 4.75 (s, 2H), 6.96 (d, J=6Hz, 1H), 7.3~7.9 (m, 3H), 8.25 (d, J=6Hz, 1H)

EXAMPLE 28

2-[4-(2-Hydroxyethoxy)-3-methylpyridine-2-yl]methylsulfinyl-5-methoxy-1H-benzimidazole

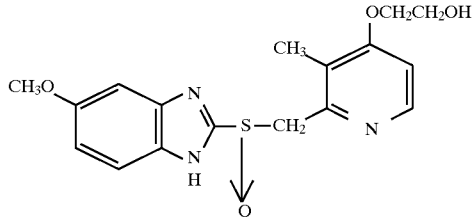

0.9 g of 2-[4-(2-hydroxyethoxy)-3-methylpyridine-2-yl]methylthio-5-methoxy-1H-benzimidazole was dissolved in a mixture comprising 5 ml of methanol and 80 ml of dichloromethane to obtain a solution. 0.51 g of m-chloroperbenzoic acid was added to this solution at −60° C. The obtained mixture was stirred at −50° to −40° C. for 4.5 hours, followed by the addition of 0.38 g of triethylamine. A saturated aqueous solution of sodium hydrogencarbonate was added to the obtained mixture and the resulting mixture was extracted with chloroform. The extract was dried over magnesium sulfate and filtered. The filtrate was distilled under a reduced pressure to obtain a crude product. This crude product was crystallized from dichloromethane/isopropyl ether to obtain 0.58 g of the title compound.

$^1$H-NMR (DMSO-d$_6$) δ; 2.17 (s, 3H), 3.8 (s, 3H), 3.6~4.18 (m, 4H), 4.73 (ABq, J=14Hz, Δv=8Hz, 2H), 6.8~7.6 (m, 4H), 8.21 (d, J=6Hz, 1H)

EXAMPLE 29

2-[4-(2-Hydroxyethoxy)-3-methylpyridine-2-yl]methylsulfinyl-1H-benzimidazole

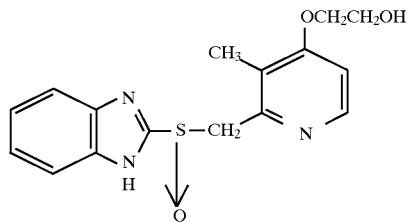

The title compound was prepared in a similar manner to that described in Example 28.

$^1$H-NMR (DMSO-d$_6$) δ; 2.17 (s, 3H), 3.6~4.2 (m, 4H), 4.74 (s, 2H), 6.95 (d, J=6Hz, 1H), 7.18~7.77 (m, 4H), 8.22 (d, J=6Hz, 2H)

EXAMPLE 30

2-[4-(2-Hydroxyethoxy)-3-methylpyridine-2-yl]methylsulfinyl-5-trifluoromethyl-1H-benzimidazole

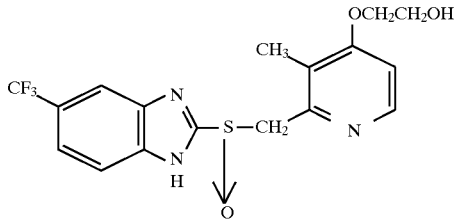

The title compound was prepared in a similar manner to that described in Example 28.

PREPARATIVE EXAMPLE 13

4-(3-Methoxypropoxy)-2,3-dimethylpyridine N-oxide

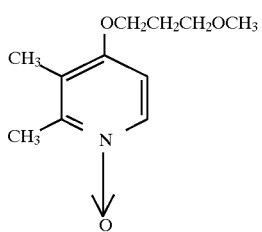

2.0 g (22 mmol) of 3-methoxypropanol was dissolved in 50 ml of dimethyl sulfoxide to obtain a solution. 2.7 g (66 mmol) of sodium hydride was added to this solution at a room temperature. The obtained mixture was stirred at 60° C. for one hour and cooled to a room temperature by allowing to stand, followed by the addition of 3.0 g (19 mmol) of 4-chloro-2,3-dimethylpyridine N-oxide. The obtained mixture was stirred at 40° C. for one hour. After the completion of the reaction, the reaction mixture was distilled to remove the dimethyl sulfoxide. The obtained residue was purified by silica gel column chromatography to obtain 760 mg of 4-(3-methoxypropoxy)-2,3-dimethylpyridine N-oxide.

¹H-NMR (CDCl₃) δ; 2.1 (m, 2H), 2.2 (s, 3H), 2.54 (s, 3H), 3.3 (s, 3H), 3.55 (t, J=6Hz, 2H), 4.1 (t, J=6Hz, 2H), 6.65 (d, J=7.4Hz, 1H), 8.16 (d, J=7.4Hz, 1H)

PREPARATIVE EXAMPLE 14

2-Chloromethyl-4-(3-methoxypropoxy)-3-methylpyridine

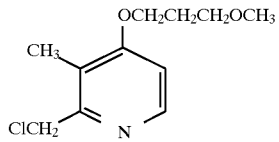

20 ml of acetic anhydride was added to 760 mg (3.6 mmol) of 4-(3-methoxypropoxy)-2,3-dimethylpyridine N-oxide to carry out the reaction at 90° C. for one hour. The reaction mixture was distilled to remove the acetic anhydride, followed by the addition of a saturated aqueous solution of sodium hydrogencarbonate. The obtained mixture was extracted with chloroform. The extract was concentrated to obtain 700 mg of 2-acetoxymethyl-4-(3-methoxypropoxy)-3-methylpyridine as a brown oil.

500 mg of sodium hydroxide and 15 cc of ethanol were added to the 2-acetoxymethyl-4-(3-methoxypropoxy)-3-methylpyridine prepared above. The obtained mixture was stirred at 50° C. for one hour. After the completion of the reaction, the reaction mixture was distilled to remove the ethanol, followed by the addition of water. The obtained mixture was extracted with chloroform. The obtained chloroform layer was concentrated to obtain 450 mg of 2-hydroxymethyl-4-(3-methoxypropoxy)-3-methylpyridine as a brown oil.

¹H-NMR (CDCl₃) δ; 2.04 (s, 3H), 2.1 (m, 2H), 3.35 (s, 3H), 3.56 (t, J=5.7 Hz, 2H), 4.12 (t, J=5.7 Hz, 2H), 4.64 (s, 2H), 6.7 (d, J=7 Hz, 1H), 8.24 (d, J=7 Hz, 1H)

450 mg of the 2-hydroxymethyl-4-(3-methoxypropoxy)-3-methylpyridine prepared above was dissolved in 20 ml of dichloromethane to obtain a solution. 760 mg of thionyl chloride was dropwise added to this solution at 0° C. The obtained mixture was stirred at a room temperature for 2 hours. After the completion of the reaction, the reaction mixture was distilled to remove the dichloromethane and the thionyl chloride. A saturated aqueous solution of sodium hydrogencarbonate was added to the obtained residue. The obtained mixture was extracted with chloroform. The obtained chloroform layer was concentrated to obtain 470 mg of 2-chloromethyl-4-(3-methoxypropoxy)-3-methylpyridine as a brown crystal.

¹H-NMR (CDCl₃) δ; 2.1 (m, 2H), 2.27 (s, 3H), 3.36 (s, 3H), 3.56 (t, J=5.7 Hz, 2H), 4.12 (t, J=5.7 Hz, 2H) 4.69 (s, 2H), 6.71 (d, J=7 Hz, 1H), 8.26 (d, J=7 Hz, 1H)

EXAMPLE 31

2-[{4-(3-Methoxypropoxy)-3-Methylpyridine-2-Yl}-Methylthio]-1H-Benzimidazole

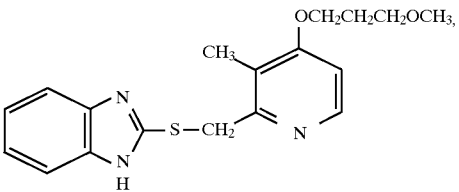

20 cc of ethanol was added to a mixture comprising 280 mg (1.8 mmol) of 2-mercapto-1H-benzimidazole, 470 mg (2 mmol) of 2-chloromethyl-4-(3-methoxypropoxy)-3-methylpyridine and 100 mg (2.4 mmol) of sodium hydroxide. The obtained mixture was stirred at 50° C. for 3 hours. After the completion of the reaction, the reaction mixture was distilled to remove the ethanol. The obtained residue was purified by silica gel column chromatography to obtain 590 mg of 2-[{4-(3-methoxypropoxy)-3-methylpyridine-2-yl}methylthio]-1H-benzimidazole as a pale yellow crystal.

¹H-NMR (CDCl₃) δ; 2.09 (t, J=6.1 Hz, 2H), 2.26 (s, 3H), 3.35 (s, 3H), 3.56 (t, J=6.1 Hz, 2H), 4.13 (t, J=6.1 Hz, 2H), 4.37 (s, 2H), 6.76 (d, J=6.1 Hz, 1H), 7.1~7.25 (m, 2H), 7.5 (br, s, 2H), 8.33 (d, J=6.1 Hz, 1H)

EXAMPLE 32

2-{4-(3-Methoxypropoxy)-3-Methylpyridine-2-Yl}Methylsulfinyl-1H-Benzimidazole

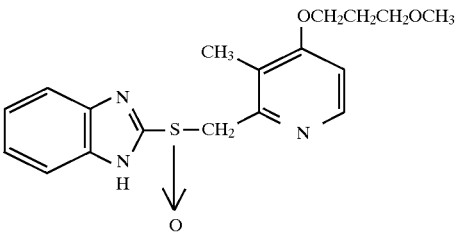

5 g of 2-[{4-(3-methoxypropoxy)-3-methylpyridine-2-yl}methylthio]-1H benzimidazole was dissolved in a mixture comprising 100 ml of dichloromethane and 25 ml of diethyl ether to obtain a solution. 2.83 g of 85% m-chloroperbenzoic acid was added to this solution in portions at −45° C. After the completion of the reaction, 2 g of triethylamine was added to the reaction mixture and the obtained mixture was heated to −10° C., followed by the addition of 50 ml of 1N sodium hydroxide. The obtained mixture was stirred at a room temperature for 30 minutes. The obtained aqueous layer was washed with 20 ml of dichloromethane twice and adjusted to pH 11 with a 2M aqueous solution of ammonium acetate. The aqueous layer was extracted with 50 ml of dichloromethane thrice. The obtained dichloromethane layer was washed with 50 ml of a saturated aqueous solution of sodium hydrogencarbonate twide, dried over magnesium sulfate and distilled to remove the dichloromethane. The obtained oily product was crystallized from dichloromethane/ether to obtain 4.17 g of the title compound as a white crystal. M.p.: 99° to 100° C. (dec.).

¹H-NMR (CDCl₃) δ; 1.83~2.09 (m, 2H), 2.13 (s, 3H), 3.34 (s, 3H), 3.52 (t, J=6.2 Hz, 2H), 4.05 (t, J=6.2 Hz, 2H), 4.79 (s, 2H), 6.70 (d, J=5.7 Hz, 1H), 7.07~7.30 (m, 2H), 7.30~7.60 (br, s, 2H), 8.27 (d, J=5.7 Hz, 1H)

EXAMPLE 33

Sodium Salt of 2-[{4-(3-Methoxypropoxy)-3-Methylpyridine-2-Yl}Methylsulfinyl]-1H-Benzimidazole

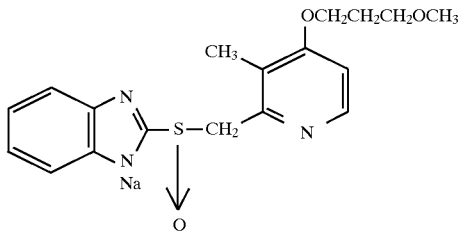

500 mg (1.46 mmol) of 2-[{4-(3-methoxypropoxy)-3-methylpyridine-2-yl}methylthio]-1H-benzimidazole was dissolved in 20 cc of dichloromethane to obtain a solution. 320 mg of 85% m-chloroperbenzoic acid was added to this solution in portions at −45° C. After the completion of the reaction, 370 mg of triethylamine was added to the reaction mixture. The obtained mixture was heated to −10° C., followed by the addition of 30 ml of a saturated aqueous solution of sodium carbonate. The obtained mixture was stirred at a room temperature for 30 minutes and extracted with dichloromethane. The extract was dried over magnesium sulfate and distilled to remove the dichloromethane. Thus, a crude product was obtained. This crude product was dissolved in 14.6 cc of a 0.1N aqueous solution of sodium hydroxide to obtain a solution. This solution was distilled together with 30 cc of ethanol thrice to remove the water as an azeotropic mixture with ethanol and dried in a vacuum. Ether was added to the obtained residue to precipitate a white crystal. This crystal was washed with ether thrice by decantation and dried in a vacuum to obtain 530 mg of sodium salt of 2-[{4-(3-methoxypropoxy)-3-methylpyridine-2-yl}methylsulfinyl]-1H-benzimidazole. M.p.: 140° to 141° C. (dec.).

$M^{+1}$: 382

$^1$H-NMR (DMSO-$d_6$) δ; 1.99 (t, J=6.1 Hz, 2H), 2.17 (s, 3H), 3.25 (s, 3H), 3.49 (t, J=6.1 Hz, 2H), 4.09 (t, J=6.1 Hz, 2H), 4.56 (ABq, J=14.1 Hz, Δv=21.3 Hz, 2H), 6.8~6.9 (m, 3H), 7.4~7.5 (m, 2H), 8.27 (d, J=5.7 Hz, 1H)

EXAMPLE 34

2-[{4-(3-Hydroxypropoxy)-3-Methylpyridine-2-Yl}-Methylthio]-1H-Benzimidazole

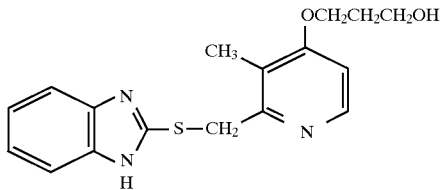

80 ml of ethanol was added to a mixture comprising 1.39 g (9.27 mmol) of 2-mercaptobenzimidazole, 2.0 g (9.27 mmol) of 2-chloromethyl-4-(3-hydroxypropoxy)-3-methylpyridine and 0.44 g (11.1 mmol) of sodium hydroxide. The obtained mixture was stirred at 50° C. for one hour. After the completion of the reaction, the reaction mixture was concentrated. The obtained residue was purified by silica gel column chromatography to obtain 1.7 g of the title compound (56%).

$M^{+1}$: 368

$^1$H-NMR (DMSO-$d_6$) δ; 1.8~2.1 (m, 2H), 2.24 (s, 3H), 3.6 (t, J=6 Hz, 2H), 4.2 (t, J=6 Hz, 2H), 4.7 (s, 2H), 7.0~7.38 (m, 3H), 7.38~7.6 (m, 2H), 8.35 (d, J=6 Hz, 1H)

EXAMPLE 35

Sodium Salt of 2-[{4-(3-Hydroxypropoxy)-3-Methylpyridine-2-Yl}Methylsulfinyl]-1H-Benzimidazole

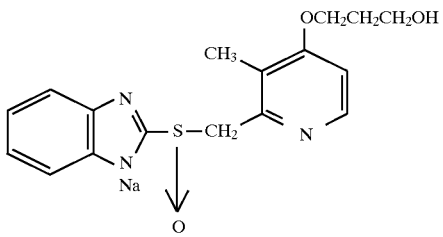

1.0 g (3.04 mmol) of 2-[{4-(3-hydroxypropoxy)-3-methylpyridine-2-yl}methylthio]-1H-benzimidazole was dissolved in 100 ml of dichloromethane to obtain a solution. 580 mg of 90% m-chloroperbenzoic acid was added to this solution at −45° C. The obtained mixture was stirred for 2 hours. After the completion of the reaction, 470 mg of triethylamine was added to the reaction mixture. The obtained mixture was heated to −20° C., followed by the addition of 30 ml of a saturated aqueous solution of sodium hydrogencarbonate. The obtained mixture was stirred at a room temperature for 30 minutes and extracted with chloroform. The obtained chloroform layer was concentrated to obtain a crude product. This crude product was crystallized from dichloromethane/ether to obtain 830 mg of 2-[{4-(3-hydroxypropoxy)-3-methylpyridine-2-yl}methylsufinyl]-1H-benzimidazole. This product was dissolved in 24 ml of 0.1N aqueous sodium hydroxide. The obtained solution was distilled together with ethanol to remove the water as an azeotropic mixture with ethanol and dried under vacuumizing with a vacuum pump. Ether was added to the obtained residue to precipitate a colorless crystal. This crystal was separated by filtration. Thus, 860 mg of the title compound was obtained (77%).

$^1$H-NMR (DMSO-$d_6$) δ; 1.7~2.1 (m, 2H), 2.16 (s, 3H), 3.58 (t, J=6 Hz, 2H), 4.12 (t, J=6 Hz, 2H), 4.55 (ABq, J=13 Hz, Δv=20 Hz, 2H), 6.7~7.0 (m, 3H), 7.3~7.6 (m, 2H), 8.27 (d, J=6 Hz, 1H)

EXAMPLE 36

2-[{4-(2-Chloroethoxy)-3-Methylpyridine-2-Yl}Methylthio]-1H-Benzimidazole

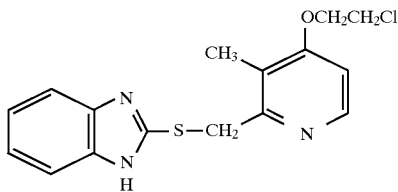

12.3 g of crude 2-mercaptobenzimidazole, 20 g of 4-(2-chloroethoxy-2-chloromethyl-3-methylpyridine hydrochloride and 11 g of sodium hydroxide were dissolved in 300 ml of ethanol to obtain a solution. This solution was stirred at 60° C. for 2 hours and distilled under a reduced pressure to remove the ethanol. The obtained residue was chromatographed over a silica gel column and eluted with 40% ethyl acetate in hexane and then with ethyl acetate to obtain 15.5 g of the title compound as a white solid.

$^1$H-NMR (CDCl$_3$) δ; 2.24 (3H, s, CH$_3$), 3.80 (2H, t, J=4 Hz, CH$_2$), 4.20 (2H, t, J=4 Hz, CH$_2$), 4.40 (2H, s, CH$_2$), 6.62 (1H, d, J=6 Hz, Py—H), 7.00~7.40 (4H, m, Ar—H), 8.28 (1H, d, J=6 Hz, Py—H)

EXAMPLE 37

Sodium Salt of 2-[{4-(2-Methylthioethoxy)-3-Methylpyridine-2-Yl}Methylsulfinyl]-1H-Benzimidazole

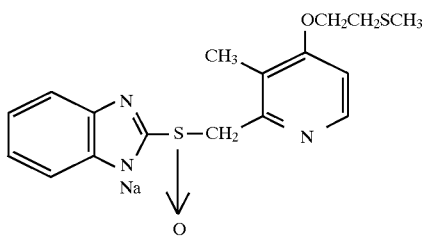

0.50 g of the thio ether prepared in Example 35 was dissolved in 20 ml of dichloromethane to obtain a solution. 0.36 g of m-chloroperbenzoic acid was added to this solution in portions at −50° to −40° C. After the completion of the reaction, 0.21 g of triethylamine was added to the reaction mixture at the same temperature. The obtained mixture was heated to −20° C., followed by the addition of 28 ml of a 1N aqueous solution of sodium hydrogencarbonate. The obtained mixture was stirred for 30 minutes and extracted with dichloromethane. The extract was washed with a saturated aqueous solution of common salt, dried over magnesium sulfate and distilled to remove the dichloromethane.

The obtained crude sulfoxide was dissolved in 10 ml of ethanol, followed by the addition of 1 g of a 15% aqueous solution of sodium methylmercaptide. The obtained mixture was stirred at 80° C. for 4 hours and distilled to remove the solvent. The residue was chromatographed over a silica gel column and eluted with 2% methanol in chloroform containing 1% of triethylamine and then with 10% methanol in chloroform to obtain a purification product. 7.2 ml of 1N aqueous sodium hydroxide and 20 ml of ethanol were added to this product. The obtained mixture was evaporated to dryness under a reduced pressure to obtain 460 mg of the title compound.

M$^{-1}$: 384

$^1$H-NMR (DMSO-d$_6$) δ; 2.18 (3H, s, CH$_3$), 2.90 (2H, t, J=7 Hz, CH$_2$), 4.24 (2H, t, J=7 Hz, CH$_2$), 4.78 (2H, s, CH$_2$), 6.80~7.60 (4H, m, Ar—H), 6.98 (1H, d, J=6 Hz, Py—H), 8.30 (1H, d, J=6 Hz, Py—H)

EXAMPLE 38

2-[{4-(2-Phenoxyethoxy)-3-Methylpyridine-2-Yl}Methylthio]-1H-Benzimidazole

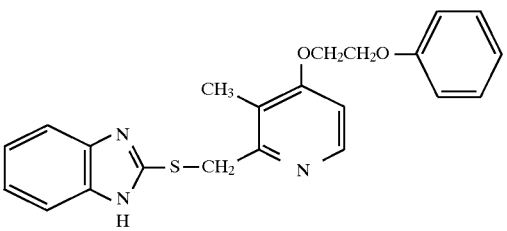

A mixture comprising 1.0 g of [4-(2-phenoxyethoxy)-3-methylpyridine-2-yl]methanol, 0.60 ml of thionyl chloride and 12 ml of dichloromethane was kept at 40° C. for 60 minutes to carry out the reaction. The reaction mixture was distilled to remove the solvent. Thus, a brown syrupy residue was obtained. 50 ml of ethanol, 0.70 g of sodium hydroxide and 1.2 g of 2-mercaptobenzimidazole were added to the residue. The obtained mixture was heated at 70° C. for two hours and distilled to remove the ethanol. The obtained residue was chromatographed over a silica gel column and eluted with 30% ethyl acetate in hexane and then with ethyl acetate to obtain 1.2 g of the title compound as a white solid.

$^1$H-NMR (DMSO-d$_6$) δ; 2.22 (3H, s), 4.40 (2H, s,), 4.70 (2H, s), 6.86~7.52 (10H, m), 8.28 (1H, d, J=6 Hz)

EXAMPLE 39

Sodium Salt of 2-[{3-Methyl-4-(2-Phenoxyethoxy)Pyridine-2-Yl}Methylsulfinyl]-1H-Benzimidazole

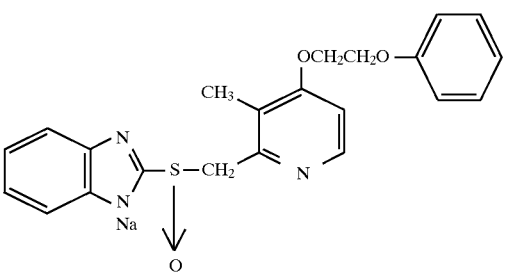

0.70 g of the thio ether prepared in Example 37 was dissolved in 200 ml of dichloromethane to obtain a solution. 0.39 g of m-chloroperbenzoic acid was added to this solution in portions at −30° to −40° C. After the completion of the reaction, 0.12 g of triethylamine was added to the reaction mixture at the same temperature. The obtained mixture was heated to −10° C., followed by the addition of 10 ml of a saturated aqueous solution of sodium hydrogencarbonate. The obtained mixture was stirred at −10° to 10° C. for 30 minutes. The obtained dichloromethane layer was washed with a saturated aqueous solution of sodium hydrogencarbonate, dried over magnesium salfate and distilled to remove the dichloromethane. The obtained residue was dissolved in a mixture comprising 20 ml of ethanol and 1.8 ml of 1N aqueous sodium hydroxid to obtain a solution. This solution was evaporated to dryness under a reduced pressure. The residue was crystallized from ethanol/ether to obtain 0.61 g of the title compound as a light brown solid.

$^1$H-NMR (DMSO-d$_6$) δ; 2.17 (3H, s), 4.32 (4H, s,), 4.36 (1H, d, J=13 Hz), 4.68 (1H, d, J=13 Hz), 6.74~7.44 (10H, m), 8.22 (1H, d, J=6 Hz)

EXAMPLE 40

2-[{4-(2-(2-Chloroethoxy)-3-Methylpyridine-2-Yl}-Methylthio]-1H-Benzimidazole and 2-[{4-(2-(2-Hydroxyethoxy)Ethoxy)-3-Methylpyridine-2-Yl}Methylthio]-1H-Benzimidazole

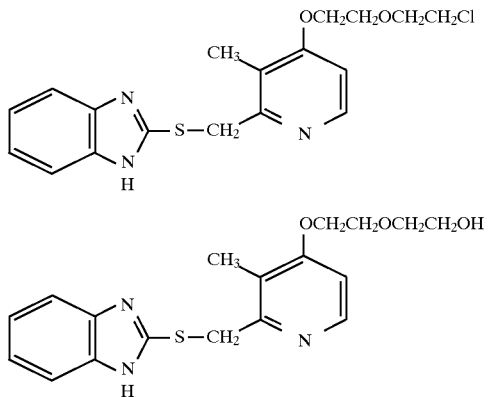

0.54 g of sodium hydroxide was added to an ethanolic solution of 3.1 g of a crude mixture comprising 4-[2-(2-chloroethoxy)ethoxy]-2-chloromethyl-3-methylpyridine and 2-chloromethyl-4-[2-(2-hydroxyethoxy)ethoxy]-3-methylpyridine which has been prepared by the chlorination of 2-hydroxymethyl-4-[2-(2-hydroxyethoxy)ethoxy]-3-methylpyridine and 2.0 g of 2-mercapto-1H-benzimidazole to obtain a mixture. This mixture was stirred at 60° C. for 1.5 hour, cooled and distilled under a reduced pressure to remove the ethanol. The obtained residue was chromatographed over a silica gel column and eluted with ethyl acetate/n-hexane and then with methanol/ethyl acetate to obtain 1.0 g of 2-[{4-(2-(2-chloroethoxy)ethoxy)-3-methylpyridine-2-yl}methylthio]-1H-benzimidazole $^1$H-NMR (CDCl$_3$) δ; 2.28 (s, 3H), 3.56~4.04 (m, 6H), 4.04~4.32 (m, 2H), 4.4 (s, 2H), 6.76 (d, J=6 Hz, 1H), 7.08~7.32 (m, 3H), 7.4~7.68 (m, 2H), 8.36 (d, J=6 Hz, 1H)

and 1.9 g of 2-[{4-(2-(2-hydroxyethoxy)ethoxy)-3-methylpyridine-2-yl}methylthio]-1H-benzimidazole.

$^1$H-NMR (CDCl$_3$) δ; 2.24 (s, 3H), 3.56~4.28 (m, 8H), 4.4 (s, 2H), 6.12 (d, J=7 Hz, 1H), 7.04~7.32 (m, 2H), 7.4~7.68 (m, 2H), 8.32 (d, J=7 Hz, 1H)

EXAMPLE 41

Sodium Salt of 2-[{4-(2-(2-Chloroethoxy)Ethoxy)-3-Methylpyridine-2-Yl}Methylsulfinyl]-1H-Benzimidazole

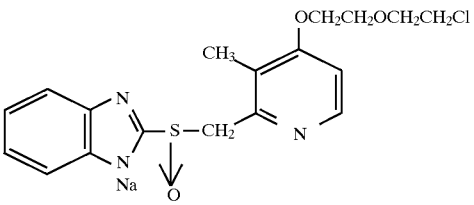

0.57 g of m-chloroperbenzoic acid was added in portions to a solution of 1.0 g of 2-[{4-(2-(2-chloroethoxy)ethoxy)-3-methylpyridine-2-yl}methylthio]-1H-benzimidazole in 80 ml of dichloromethane under stirring and dehumidifying at -50° C. The obtained mixture was stirred for 2 hours and heated to -30° C., followed by the addition of 0.51 g of triethyamine at the same temperature. The obtained mixture was made basic with a 2N aqueous solution of sodium carbonate at -10° C. and extracted with dichloromethane. The extract was dried over magnesium sulfate and distilled to remove the dichloromethane. Thus, 1.0 g of a residue was obtained. This residue was dissolved in 26 ml of 0.1N aqueous sodium hydroxide, followed by the addition of ethanol. The obtained mixture was distilled under a reduced pressure. Ethanol was added to the obtained residue and the obtained mixture was again distilled under a reduced pressure to obtain a residue. Ether was added to this residue to obtain 1.07 g of a crystal.

$^1$H-NMR (DMSO-d$_6$) δ; 2.17 (s, 3H), 3.56~3.96 (m, 6H), 4.0~4.28 (m, 2H), 4.04 (d, J=12.6 Hz, 1H), 4.68 (d, J=12.6 Hz, 1H), 6.76~8.04 (m, 3H), 7.36~7.6 (m, 2H), 8.26 (d, J=6 Hz, 1H)

EXAMPLE 42

2-[{4-(3-Ethoxy)Propoxy-3-Methylpyridine-2-Yl}Methylthio]-1H-Benzimidazole

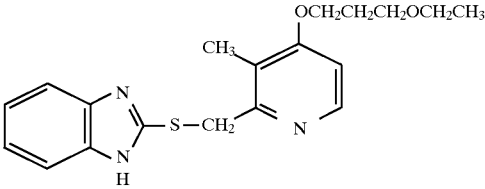

A mixture comprising 4.2 g of {4-(3-ethoxypropoxy)-3-methylpyridine-2-yl}methyl methanesulfonate, 1.87 g of 2-mercaptobenzimidazole and 30 ml of ethanol was stirred at a room temperature for one hour and distilled to remove the ethanol. The obtained residue was purified by silica gel column chromatography to obtain 0.88 g of the title compound and 5.1 g of methanesulfonate of the title compound.

$^1$H-NMR (CDCl$_3$) δ; 1.19 (t, J=7.0 Hz, 3H), 1.9~2.1 (m, 2H), 2.24 (s, 3H), 3.48 (q, J=7.0 Hz, 2H), 3.58 (t, J=6.2 Hz, 2H), 4.11 (t, J=6.2 Hz, 2H), 4.38 (s, 2H), 6.73 (d, J=5.7 Hz, 1H), 6.97~7.20 (m, 2H), 7.32~7.55 (m, 2H), 8.31 (d, J=5.7 Hz, 1H)

EXAMPLE 43

Sodium Salt of 2-[{4-(3-Ethoxypropoxy)-3-Methylpyridine- 2-Yl}Methylsulfinyl]-1H-Benzimidazole

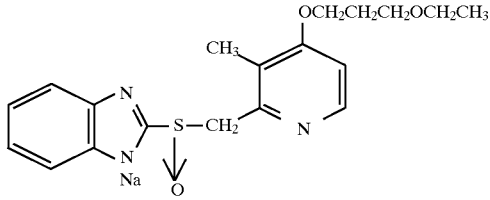

0.6 g of 2-[{4-(3-ethoxypropoxy)-3-methylpyridine-2-yl}methylthio]-1H-benzimidazole was dissolved in 30 ml of dichloromethane to obtain a solution. 0.37 g of 85% m-chloroperbenzoic acid was added to this solution at −45° C. After 2 hours, 0.43 g of triethylamine was added to the obtained mixture, followed by the addition of 30 ml of a saturated aqueous solution of sodium hydrogencarbonate. The obtained mixture was vigorously stirred at a room temperature for one hour and extracted with dichloromethane. The extract was dried over magnesium sulfate and filtered. The filtrate was concentrated to obtain a residue. This residue was dissolved in 16 ml of 0.1N aqueous sodium hydroxide and the obtained solution was distilled to remove the water. The residue was dried under a reduced pressure and crystallized from ether to obtain 0.54 g of the title compound.

$^1$H-NMR (DMSO-d$_6$) δ; 1.11 (t, J=7.0 Hz, 3H), 1.7~2.1 (m, 2H), 2.15 (s, 3H), 3.2~3.6 (m, 4H), 3.65 (s, 3H), 4.09 (t, J=6.2 Hz, 2H), 4.49 (ABq, J=11.8 Hz, Δv=17.0 Hz, 2H), 6.65~7.0 (m, 3H), 7.2~7.6 (m, 2H), 8.2 (d, J=5.6 Hz, 1H)

EXAMPLE 44

2-[{4-(3-Methoxymethoxy)Propoxy-3-Methylpyridine-2-Yl}Methylthio]-1H-Benzimidazole

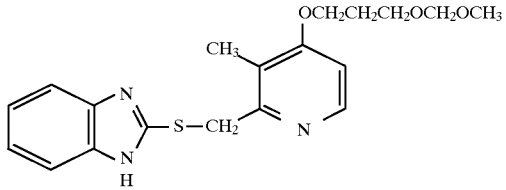

A mixture comprising 1.8 g of {4-(3-methoxymethoxy)propoxy-3-methylpyridine-2-yl}methyl methanesulfonate, 0.76 g of 2-mercaptobenzimidazole, 0.29 g of sodium hydroxide and 50 ml of ethanol was stirred at a room temperature for one hour and distilled to remove the ethanol. The obtained residue was purified by silica gel column chromatography to obtain 1.4 g of the title compound.

$^1$H-NMR (CDCl$_3$) δ; 1.9~2.2 (m, 2H), 2.26 (s, 3H), 3.33 (s, 3H), 3.73 (t, J=6.1 Hz, 2H), 4.16 (t, J=6.1 Hz, 2H), 4.38 (s, 2H), 4.62 (s, 2H), 6.76 (d, J=5.7 Hz, 1H), 7.0~7.2 (m, 2H), 7.3~7.6 (m, 2H), 8.34 (d, J=5.7 Hz, 1H)

EXAMPLE 45

Sodium Salt of 2-[{4-(3-Methoxymethoxy)Propoxy-3-Methylpyridine-2-Yl}Methylsulfinyl]-1H-Benzimidazole

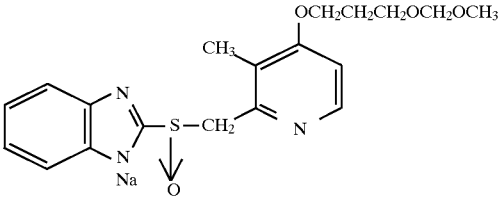

0.6 g of 2-[{4-(3-methoxymethoxy)propoxy-3-methylpyridine-2-yl}methylthio]-1H-benzimidazole was dissolved in 40 ml of dichloromethane to obtain a solution. 0.35 g of 85% m-chloroperbenzoic acid was added to this solution at −45° C. After 2 hours, 0.64 g of triethylamine was added to the mixture at −30° C., followed by the addition of 40 ml of a saturated aqueous solution of sodium hydrogencarbonate. The obtained mixture was vigorously stirred at a room temperature for 30 minutes and extracted with dichloromethane. The extract was dried over magnesium sulfate and filtered. The filtrate was concentrated to obtain a residue. This residue was dissolved in 14.4 ml of 0.1N aqueous sodium hydroxide to obtain a solution. This solution was distilled to remove the water and the residue was dried under a reduced pressure and crystallized from ether to obtain 0.57 g of the title compound.

$^1$H-NMR (DMSO-d$_6$) δ; 1.9~2.2 (m, 2H), 2.17 (s, 3H), 3.22 (s, 3H), 3.63 (t, J=5.7 Hz, 2H), 4.12 (t, J=5.7 Hz, 2H), 4.56 (s, 2H), 4.41~4.85 (2H), 6.84~7.1 (m, 3H), 7.4~7.62 (m, 2H), 8.26 (d, J=6.1 Hz, 1H)

EXAMPLE 46

2-[{4-(2-Methoxyethoxy)Ethoxy-3,5-Dimethylpyridine-2-Yl}Methylthio]-1H-Benzimidazole

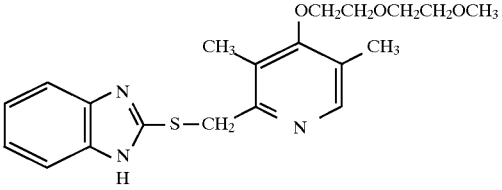

A mixture comprising 3.0 g of {4-(2-methoxyethoxy)ethoxy-3,5-dimethylpyridine-2-yl}methyl methanesulfonate, 1.17 g of 2-mercaptobenzimidazole and 30 ml of ethanol was stirred at a room temperature for one hour and distilled to remove the ethanol. The residue was purified by silica gel column chromatography to obtain 0.8 g of the title compound.

$^1$H-NMR (CDCl$_3$) δ; 2.28 (s, 3H), 2.33 (s, 3H), 3.37 (s, 3H), 3.5~3.9 (m, 6H), 3.9~4.2 (m, 2H), 4.37 (s, 2H), 7.1~7.3 (m, 2H), 7.3~7.65 (m, 2H), 8.24 (s, 1H)

EXAMPLE 47

Sodium Salt of 2-[{4-(2-Methoxyethoxy)Ethoxy-3,5-Dimethylpyridine-2-Yl}Methylsulfinyl]-1H-Benzimidazole

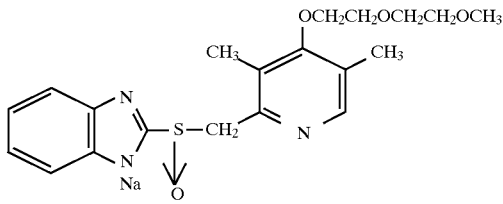

0.5 g of 2-[{4-(2-methoxyethoxy)ethoxy-3,5-dimethylpyridine-2-yl}methylthio]-1H-benzimidazole was dissolved in 30 ml of dichloromethane to obtain a solution. 0.29 g of 85% m-chloroperbenzoic acid was added to this solution at −45° C. After 2 hours, 0.34 g of triethylamine was added to the obtained mixture, followed by the addition of 30 ml of a saturated solution of sodium carbonate. The obtained mixture was vigorously stirred at a room temperature for one hour and extracted with dichloromethane. The extract was dried over magnesium sulfate and filtered. The filtrate was concentrated to obtain a residue. This residue was dissolved in 12 ml of 0.1N aqueous sodium hydroxide to obtain a solution. This solution was distilled to remove the water. The obtained residue was dried under a reduced pressure and crystallized from ether to obtain 0.57 g of the title compound.

$^1$H-NMR (DMSO-$d_6$) δ; 2.21 (s, 6H), 3.25 (s, 3H), 3.3~3.7 (m, 6H), 3.7~4.0 (m, 2H), 4.39 (ABq, J=13.2 Hz, Δv=20.7 Hz, 2H), 6.65~6.9 (m, 2H), 7.2~7.5 (m, 2H), 8.21 (s, 1H)

EXAMPLE 48

5-Carboxy-2-[{4-(2-Benzyloxy)Ethoxy-3-Methylpyridine-2-Yl}Methylthio]-1H-Benzimidazole

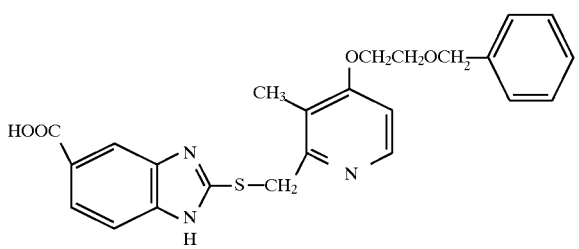

A mixture comprising 1.26 g of 5-carboxy-2-mercaptobenzimidazole, 1.8 g of 4-(2-benzyloxyethoxy)-2-chloromethyl-3-methylpyridine, 0.57 g of sodium hydroxide and 150 ml of methanol was stirred at 50° C. for 1.5 hours and distilled under a reduced pressure to remove the methanol. The obtained residue was purified by silica gel column chromatography and recrystallized from a methanol/ethyl acetate mixture to obtain 1.52 g of the title compound.

$^1$H-NMR (DMSO-$d_6$) δ; 2.25 (s, 3H), 3.65~3.9 (m, 2H), 4.1~4.3 (m, 2H), 4.58 (s, 2H), 4.74 (s, 2H), 6.95 (d, J=5.7 Hz, 1H), 7.32 (s, 5H), 7.50 (d, J=8.3 Hz, 1H), 7.79 (dd, J=1.3 Hz, 8.3 Hz, 1H), 8.04 (s, 1H), 8.24 (d, J=5.7 Hz, 1H)

EXAMPLE 49

5-Ethoxycarbonyl-2-[{4-(2-Benzyloxy)Ethoxy-3-Methylpyridine-2-Yl}Methylthio]-1H-Benzimidazole

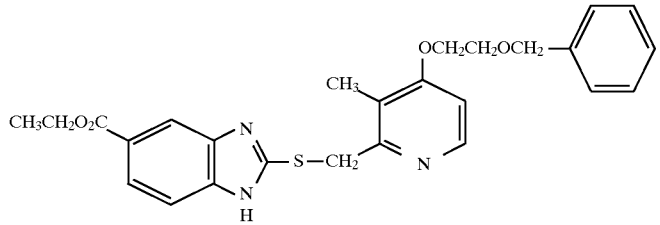

A mixture comprising 1.0 g of 5-carboxy-2-[{4-(2-benzyloxy)ethoxy-3-methylpyridine-2-yl}methylthio]-1H-benzimidazole, 200 ml of ethanol and 1 ml of concentrated sulfuric acid was heated under reflux for 4 hours, while dehydrating the system with a molecular sieve. The resulting mixture was neutralized with a saturated aqueous solution of sodium carbonate and distilled to remove the ethanol, followed by the addition of a saturated aqueous solution of sodium hydrogencarbonate. The obtained mixture was extracted with chloroform. The extract was dried over magnesium sulfate and filtered. The filtrate was concentrated to obtain a crude product. This crude product was purified by silica gel column chromatography to obtain 0.76 g of the title compound.

$^1$H-NMR (DMSO-$d_6$) δ; 1.35 (t, J=7.0 Hz, 3H), 2.25 (s, 3H), 3.7~3.9 (m, 2H), 4.15~4.3 (m, 2H), 4.24 (q, J=7.0 Hz, 2H), 4.57 (s, 2H), 4.75 (s, 2H), 6.96 (d, J=5.7 Hz), 7.32 (s, 5H), 7.52 (d, J=8.5 Hz, 1H), 7.79 (dd, J=1.3 Hz, 8.5 Hz, 1H), 8.05 (d, J=1.3 Hz, 1H), 8.24 (d, J=5.7 Hz, 1H)

EXAMPLE 50

Sodium Salt of 5-Ethoxycarbonyl-2-[{4-(2-Benzyloxy)Ethoxy-3-Methylpyridine-2-Yl}methylsulfinyl]-1H-Benzimidazole

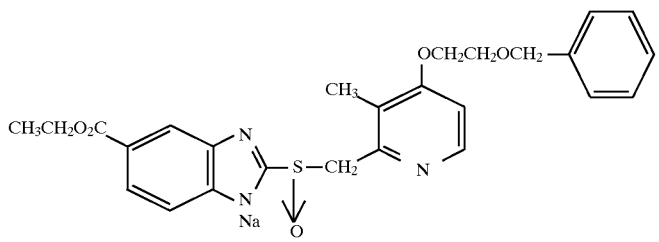

0.7 g of 5-ethoxycarbonyl-2-[{4-(2-benzyloxy)ethoxy-3-methylpyridine-2-yl}methylthio]-1H-benzimidazole was dissolved in 50 ml of dichloromethane to obtain a solution. 0.3 g of 85% m-chloroperbenzoic acid was added to this solution at −45° C. After 2 hours, the obtained mixture was heated to −30° C., followed by the addition of 0.43 g of triethylamine. After 30 minutes, the obtained mixture was heated to −10° C., followed by the addition of 50 ml of a saturated aqueous solution of sodium hydrogencarbonate. The obtained mixture was vigorously stirred at a room temperature for 30 minutes and extracted with dichloromethane. The extract was dried over magnesium sulfate and filtered. The filtrate was concentrated and the obtained residue was dissolved in 10 ml of dichloromethane, followed by the addition of 0.056 g of 60% sodium hydride. The obtained mixture was stirred at a room temperature for 30 minutes and distilled to remove the dichloromethane. The obtained residue was crystallized from ether to obtain 0.59 g of the title compound.

$^1$H-NMR (DMSO-d$_6$) δ; 1.34 (t, J=7.0 Hz, 3H), 2.18 (s, 3H), 3.7~3.9 (m, 2H), 4.1~4.3 (m, 2H), 4.24 (q, J=7.0 Hz, 2H), 4.57 (s, 3H), 4.65 (s, 2H), 6.94 (d, J=5.7 Hz, 1H), 7.30 (s, 5H), 7.50~7.86 (m, 3H), 8.26 (d, J=5.7 Hz, 1H)

EXAMPLE 51

2-[4-(4-Methoxybutoxy)Pyridine-2-Yl]Methylthio-1H-Benzimidazole

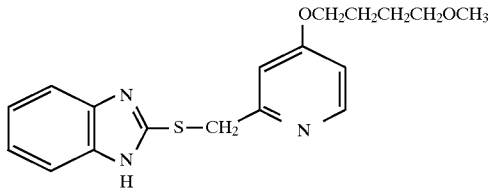

A mixture comprising 2.55 g (0.017 mol) of 2-mercaptobenzimidazole, 5.09 g (0.022 mol) of 2-chloromethyl-4-(4-methoxybutoxy)pyridine, 0.84 g (0.020 mol) of 95% sodium hydroxide and 60 ml of ethanol was stirred at 40° C. for 1.5 hours. After the completion of the reaction, the reaction mixture was distilled to remove the solvent. The obtained residue was purified by silica gel column chromatography (ethyl acetate/n-hexane) to obtain 4.13 g of the title compound.

$^1$H-NMR (DMSO-d$_6$) δ; 1.43~1.84 (m, 4H), 3.21 (s, 3H), 3.31 (t, J=6.2 Hz, 2H), 3.99 (t, J=6.2 Hz, 2H), 4.59 (s, 2H), 6.75~6.89 (m, 1H), 7.04~7.21 (m, 2H), 7.25~7.56 (m, 2H), 8.31 (d, J=6.2 Hz, 1H)

EXAMPLE 52

Sodium Salt of 2-[4-(4-Methoxybutoxy)Pyridine-2-Yl]-Methylsulfinyl-1H-Benzimidazole

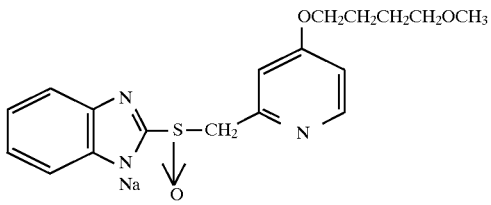

2.06 g (0.006 mol) of 2-[4-(4-methoxybutoxy)pyridine-2-yl]methylthio-1H-benzimidazole was dissolved in 80 ml of dichloromethane to obtain a solution. 1.30 g (0.006 mol) of 80% m-chloroperbenzoic acid and 5 ml of methanol were added to the solution at −40° C. in a nitrogen atmosphere. The obtained mixture was stirred for 1.5 hours. After the completion of the reaction, 1.0 g of triethylamine was added to the reaction mixture. The obtained mixture was heated to −10° C., followed by the addition of 50 ml of a 2N aqueous solution of sodium carbonate. The obtained mixture was stirred at a room temperature for 30 minutes and extracted with 150 ml of dichloromethane twice. The extract was dried over magnesium sulfate and filtered. The filtrate was distilled to remove the solvent and the obtained residue was dried in a vacuum to obtain an oil. This oil was dissolved in 54 ml of 0.1N aqueous sodium hydroxide, followed by the addition of ethanol. The obtained mixture was distilled to remove the solvent. The obtained residue was washed with ether thrice and dried in a vacuum to obtain 2.02 g of the title compound as a white powder.

$^1$H-NMR (DMSO-d$_6$) δ; 1.40~1.74 (m, 4H), 3.17~3.40 (m, 2H), 3.23 (s, 3H), 3.66~3.88 (m, 2H), 4.48 (ABq, J=12.5 Hz, Δv=12.7 Hz, 2H), 6.60~7.00 (m, 3H), 7.35~7.58 (m, 2H), 8.32 (d, J=6.2 Hz, 1H)

EXAMPLE 53

2-[4-(3-Methoxypropoxy)Pyridine-2-Yl]Methylthio-1H-Benzimidazole

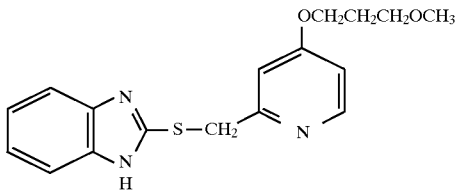

A mixture comprising 1.50 g (0.01 mol) of 2-mercapto-1H-benzimidazole, 3.20 g (0.015 mol) of 2-chloromethyl- 4-(3-methoxypropoxy)pyridine, 0.51 g (0.012 mol) of 95% sodium hydroxide and 60 ml of ethanol was stirred at 40° C. for 0.5 hour and filtered. The filtrate was concentrated under a reduced pressure and purified by silica gel column chromatography (ethyl acetate/n-hexane) to obtain 3.27 g of the title compound as a colorless crystal.

$^1$H-NMR (DMSO-d$_6$) δ; 1.62~2.06 (m, 2H), 3.16 (s, 3H), 3.34 (t, J=6.2 Hz, 2H), 3.97 (t, J=6.2 Hz, 2H), 4.51 (s, 2H), 6.62~6.84 (m, 1H), 6.88~7.16 (m, 2H), 7.20~7.48 (m, 2H), 8.20 (d, J=6.2 Hz, 1H)

EXAMPLE 54

Sodium Salt of 2-[4-(3-Methoxypropoxy)Pyridine-2-Yl]-Methylsulfinyl-1H-Benzimidazole

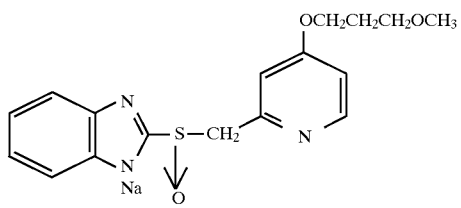

1.65 g (0.005 mol) of 2-[4-(3-methoxypropoxy)pyridine-2-yl]methylthio-1H-benzimidazole was dissolved in 50 ml of dichloromethane to obtain a solution. 1.08 g (0.005 mol) of 80% m-chloroperbenzoic acid was added to the solution at −40° C. in a nitrogen atmosphere. The obtained mixture was stirred for 15 minutes. After the completion of the reaction, 0.8 g of triethylamine was added to the reaction mixture. The obtained mixture was heated to −10° C., followed by the addition of 30 ml of a 2N aqueous solution of sodium carbonate. The obtained mixture was stirred at a room temperature for 30 minutes and extracted with 100 ml of dichloromethane thrice. The extract was dried over magnesium sulfate and filtered. The filtrate was concentrated under a reduced pressure and dried in a vacuum. The obtained residue was dissolved in 50 ml of 0.1N aqueous sodium hydroxide, followed by the addition of ethanol. The obtained mixture was distilled to remove the solvent and the residue was washed with ether and dried in a vacuum to obtain 1.70 g of the title compound as a white crystal.

$^1$H-NMR (DMSO-d$_6$) δ; 1.70~1.98 (m, 2H), 3.22 (s, 3H), 3.37 (t, J=6.2 Hz, 2H), 3.44~3.89 (m, 2H), 4.47 (ABq, J=12.3 Hz, Δv=10.6 Hz, 2H), 6.70~6.94 (m, 4H), 7.42~7.53 (m, 2H), 8.32 (d, J=5.8 Hz, 1H)

EXAMPLE 55

2-[4-{3-(2-Methoxyethoxy)Propoxy}-3-Methylpyridine-2-Yl]Methylthio-1H-Benzimidazole

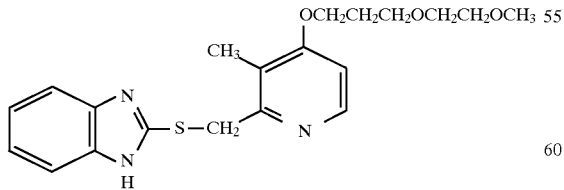

2.24 g of triethylamine and 1.27 g of methanesulfonyl chloride were added to a solution of 1.4 g of crude 2-hydroxymethyl-4-{3-(2-methoxy)}-3-methylpyridine in dichloromethane at −30° C. The obtained mixture was gradually returned to a room temperature, followed by the addition of a saturated aqueous solution of sodium hydrogencarbonate. The obtained mixture was stirred for 30 minutes and extracted with chloroform. The extract was dried over magnesium sulfate and distilled under a reduced pressure to remove the chloroform. 1.9 g of crude [4-{3-(2-methoxyethoxy)propoxy}-3-methylpyridine-2-yl]methyl methanesulfonate was obtained as a red oil. 0.83 g of 2-mercapto-1H-benzimidazole was added to this oil. The obtained mixture was stirred together with 20 ml of ethanol at a room temperature for 30 minutes, followed by the addition of a saturated aqueous solution of sodium hydrogencarbonate. The obtained mixture was stirred at a room temperature for 30 minutes and extracted with chloroform. The extract was dried over magnesium sulfate and distilled under a reduced pressure to obtain a residue. This residue was chromatographed over a silica gel column and eluted with ethyl acetate/n-hexane to obtain 1.55 g of an oil.

$^1$H-NMR (CDCl$_3$) δ; 2.12 (q, J=6.15 Hz, 2H), 2.25 (s, 2H), 3.36 (s, 3H), 3.56 (m, 2H), 3.66 (t, J=6.15 Hz, 2H), 4.14 (t, J=6.15 Hz, 2H), 4.37 (s, 2H), 6.77 (d, J=5.72 Hz, 1H), 7.1~7.25 (m, 2H), 7.528 (m, 2H), 8.33 (d, J=5.72 Hz, 1H)

EXAMPLE 56

Sodium Salt of 2-[4-{3-(2-Methoxyethoxy)Propoxy}-3-Methylpyridine-2-Yl]Methylsulfinyl-1H-Benzimidazole

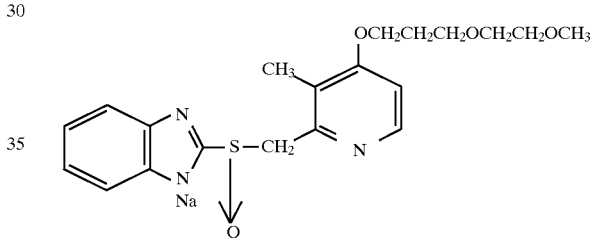

681 mg of 85% m-chloroperbenzoic acid was added in portions to a solution of 1.3 g of 2-[4-(3-(2-methoxyethoxy)propoxyl-3-methylpyridine-2-yl]methylthio-1H-benzimidazole in 70 ml of dichloromethane under stirring and dehumidifying. The obtained mixture was stirred for 30 minutes, followed by the addition of 483 mg of triethylamine. The obtained mixture was heated to −20° C., followed by the addition of a 2N aqueous solution of sodium carbonate. The obtained mixture was stirred at a room temperature for 30 minutes and extracted with dichloromethane twice. The extract was washed with a saturated aqueous solution of sodium hydrogencarbonate, dried over magnesium sulfate and distilled under a reduced pressure to obtain a crude oil. 30 ml of 0.1N aqueous sodium hydroxide and ethanol were added to this oil. The obtained mixture was distilled under a reduced pressure at 40° C. to remove the medium. Ethanol was again added to the obtained residue and the obtained mixture was distilled under a reduced pressure to remove the medium. The obtained residue was crystallized from anhydrous ether to obtain 1.24 g of a crystal.

$^1$H-NMR (DMSO-d$_6$) δ; 1.98 (q, J=6.15 Hz, 2H), 2.15 (s, 3H), 3.22 (s, 3H), 3.47 (m, 4H), 3.56 (t, J=6.15 Hz, 2H), 4.09 (t, J=6.15 Hz, 2H), 4.542 (ABq, J=13.18 Hz, Δv=14.74 Hz, 1H), 6.8~7.0 (m, 3H), 7.39~7.57 (m, 2H), 8.27 (d, J=5.71 Hz, 1H)

EXAMPLE 57

2-[{4-(4-Methoxybutoxy)-3-Methylpyridine-2-Yl}Methylthio]-1H-Benzimidazole

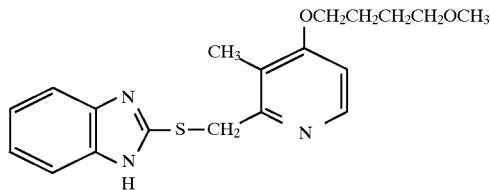

611 mg of triethylamine and 686 mg of methanesulfonyl chloride were added to a solution of 0.84 g of crude 2-hydroxy-4-(4-methoxybutoxy)-3-methylpyridine in 30 ml of dichloromethane at −20° C. under stirring and dehumidifying to obtain a mixture. This mixture was gradually brought to a room temperature, followed by the addition of a saturated aqueous solution of sodium hydrogencarbonate. The obtained mixture was stirred for 30 minutes and extracted with chloroform. The extract was dried over magnesium sulfate and distilled under a reduced pressure to remove the chloroform. Thus, a red oil was obtained. 560 mg of 2-mercapto-1H-benzimidazole and 30 ml of ethanol were added to this oil. The obtained mixture was stirred at a room temperature for 30 minutes, made basic with a 2N aqueous solution of sodium carbonate and extracted with chloroform. The extract was dried over magnesium sulfate and distilled under a reduced pressure to remove the chloroform. The obtained residue was chromatographed over a silica gel column and eluted with ethyl acetate/n-hexane to obtain 0.42 g of an oil.

$^1$H-NMR (CDCl$_3$) δ; 1.4~2.16 (m, 4H), 2.26 (s, 3H), 3.35 (s, 3H), 3.45 (t, J=5.72 Hz, 2H), 4.06 (t, J=5.72 Hz, 2H), 4.37 (s, 2H), 6.74 (d, J=5.71 Hz, 1H), 7.1~7.25 (m, 2H), 7.48~7.56 (m, 2H), 8.33 (d, J=5.72 Hz, 1H)

PREPARATIVE EXAMPLE 15

[4-{3-(2-Methoxyethoxy)Propoxy}-3-Methylpyridine-2-Yl]Methyl Methanesulfonate

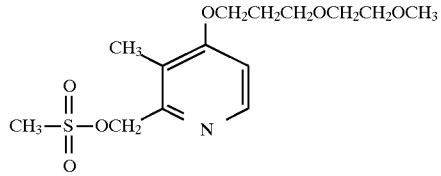

2.24 g of triethylamine and 1.27 g of methanesulfonyl chloride were added to a solution of 1.4 g of crude 2-hydroxy-4-{3-(2-methoxyethoxy))-3-methylpyridine in dichloromethane at −30° C. to obtain a mixture. This mixture was brought to a room temperature, followed by the addition of a saturated aqueous solution of sodium hydrogencarbonate. The obtained mixture was stirred for 30 minutes and extracted with chloroform. The extract was dried over magnesium sulfate and distilled under a reduced pressure to remove the chloroform. 1.9 g of a crude red oil was obtained.

EXAMPLE 58

2-[4-{3-(2-Methoxyethoxy)Propoxy}-3-Methylpyridine-2-Yl]Methylthio-1H-Benzimidazole

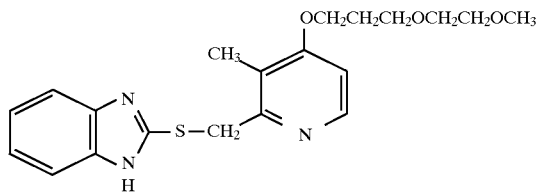

A mixture comprising 1.9 g of crude [4-(3-(2-methoxyethoxy)propoxyl-3-methylpyridine-2-yl]methyl methanesulfonate, 0.83 g of 2-mercapto-1H-benzimidazole and 20 ml of ethanol was stirred at a room temperatures for one hour, made basic with a saturated aqueous solution of sodium hydrogencarbonate and extracted with chloroform. The extract was dried over magnesium sulfate and distilled under a reduced pressure. The obtained residue was chromatographed over a silica gel column and eluted with ethyl acetate/n-hexane to obtain 1.5 g of an oily product.

$^1$H-NMR (CDCl$_3$) δ; 2.12 (q, J=6.2 Hz, 2H), 2.25 (s, 3H), 3.36 (s, 3H), 3.57 (m, 2H), 3.66 (t, J=6.2 Hz, 2H), 4.14 (t, J=6.2 Hz, 2H)), 4.37 (s, 2H), 6.77 (d, J=3.1 Hz, 1H), 7.15 (m, 2H), 7.53 (m, 2H), 8.39 (d, J=3.1 Hz, 1H)

PREPARATIVE EXAMPLE 16

2-Chloromethyl-4-(4-Methoxybutoxy)Pyridine

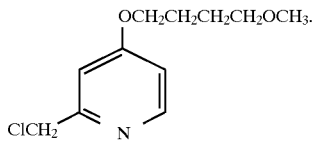

5.6 g of crude 2-hydroxymethyl-4-(4-methoxybutoxy) pyridine was dissolved in 80 ml of chloroform to obtain a solution. A solution of 3.8 g of thionyl chloride in 10 ml of chloroform was dropwise added to this solution at 0° C. The obtained mixture was stirred at 0° C. for one hour. After the completion of the reaction, the reaction mixture was neutralized with a saturated aqueous solution of sodium hydrogencarbonate and extracted with 200 ml of chloroform twice. The extract was dried over magnesium sulfate and filtered, The filtrate was distilled to remove the solvent. The obtained residue was dried in a vacuum to obtain 5.09 g of the title compound as a crude oil.

$^1$H-NMR (CDCl$_3$) δ; 1.55~2.05 (m, 4H), 3.35 (s, 3H), 3.38~3.53 (m, 2H), 3.91~4.17 (m, 2H), 4.61 (s, 2H), 6.55~7.01 (m, 2H), 8.36 (d, J=6.2 Hz, 1H)

PREPARATIVE EXAMPLE 17

2-Hydroxymethyl-4-(4-Methoxybutoxy)Pyridine

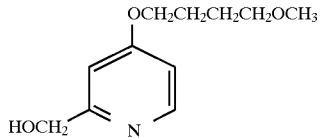

5.06 g (0.024 mol) of 4-(4-methoxybutoxy)-2-methylpyridine 1-oxide was dissolved in 80 ml of acetic anhydride to obtain a solution. This solution was stirred at 100° C. for one hour, cooled and distilled to remove the solvent. 150 ml of 1N hydrochloric acid was added to the residue. The obtained mixture was stirred at 100° C. for one hour, cooled, neutralized with sodium hydrogencarbonate and extracted with 200 ml of chloroform twice. The extract was dried over magnesium sulfate and filtered. The filtrate was distilled to remove the solvent and the residue was dried in a vacuum to obtain 5.66 g of the title compound as a crude oil.

$^1$H-NMR (CDCl$_3$) δ; 1.58~2.08 (m, 4H), 3.32~3.54 (m, 2H), 3.34 (s, 3H), 3.82~4.16 (m, 2H), 4.69 (s, 2H), 5.02 (s, 1H)), 6.54~6.88 (m, 2H), 8.30 (d, J=6.2 Hz, 1H)

PREPARATIVE EXAMPLE 18

4-(4-Methoxybutoxy)-2-Methylpyridine 1-Oxide

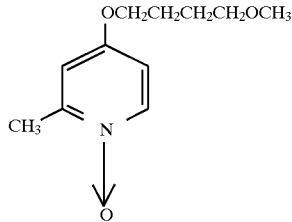

6.77 g (0.065 mol) of 4-methoxybutanol was dissolved in 60 ml of dimethyl sulfoxide to obtain a solution. 2.6 g (0.065 mol) of 60% sodium hydride was added to this solution at a room temperature in a nitrogen atmosphere. The obtained mixture was heated to 60° C., stirred for one hour and cooled to a room temperature. A solution of 4.66 g (0.032 mol) of 4-chloro-2-methylpyridine 1-oxide in 20 ml of dimethyl sulfoxide was dropwise added to the resulting mixture. The obtained mixture was stirred at 40° C. for one hour. After the completion of the reaction, 5 ml of water was added to the mixture and the obtained mixture was, evaporated to dryness to remove the solvent. 150 ml of water was added to the residue. The obtained mixture was extracted with 200 ml of chloroform four times. The extract was dried over magnesium sulfate and filtered. The filtrate was distilled to remove the solvent. The residue was purified by silica gel column chromatography (ethyl acetate/methanol) to obtain 5.06 g of the title compound as an oil.

$^1$H-NMR (CDCl$_3$) δ; 1.54~2.07 (m, 4H), 2.52 (s, 3H), 3.36 (s, 3), 3.44 (t, J=6.2 Hz, 2H), 4.01 (t, J=6.2 Hz, 2H), 6.60~6.84 (m, 2H), 8.14 (d, J=5.3 Hz, 1H)

PREPARATIVE EXAMPLE 19

4-Methoxybutanol

27.04 g (0.3 mol) of 1,4-butanediol was dissolved in 150 ml of tetrahydrofuran to obtain a solution. 7.2 g (0.18 mol) of 60% sodium hydride was added to this solution at 0° C. in a nitrogen atmosphere. The obtained mixture was heated under reflux for one hour and cooled to 0° C. 21.73 g (0.15 mol) of 98% methyl iodide was dropwise added to the resulting mixture. The obtained mixture was stirred at a temperature of 30° C. or below for 1.5 hours. After the completion of the reaction, the reaction mixture was filtered. The filtrate was distilled to remove the solvent. 200 ml of water was added to the residue and the obtained mixture was washed with 200 ml of n-hexane and extracted with 200 ml of chloroform four times. The extract was dried over magnesium sulfate and filtered. The filtrate was distilled to remove the solvent. 14.5 g of the title compound was obtained.

$^1$H-NMR (CDCl$_3$) δ; 1.54~1.80 (m, 4H), 1.71 (s, 1H), 3.32 (s, 3H), 3.34~3.73 (m, 4H)

PREPARATIVE EXAMPLE 20

2-Chloromethyl-4-(3-Methoxypropoxy)Pyridine

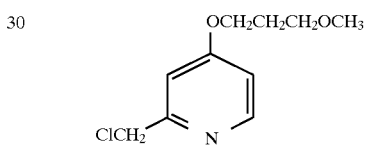

A solution of 2.60 g (0.022 mol) of thionyl chloride in 10 ml of chloroform was dropwise added to a solution of 3.64 g (0.018 mol) of 2-hydroxymethyl-4-methoxypropoxypyridine in 60 ml of chloroform under cooling with ice. The obtained mixture was stirred for one hour, neutralized with a saturated aqueous solution of sodium hydrogencarbonate and extracted with chloroform. The chloroform layer was dried over magnesium sulfate and filtered. The filtrate was concentrated under a reduced pressure to obtain 3.23 g of the title compound as a crude product. $^1$H-NMR (CDCl$_3$) δ; 1.80~2.20 (m, 2H), 3.31 (s, 3H), 3.49 ((t, J=6.2 Hz, 2H), 4.07 (t, J=6.2 Hz, 2H), 4.55 (s, 2H), 6.52~6.96 (m, 2H), 8.26 (d, J=5.3 Hz, 1H)

PREPARATIVE EXAMPLE 21

2-Hydroxymethyl-4-(3-Methoxypropoxy)Pyridine

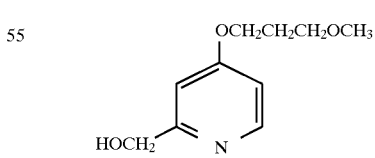

4.05 g (0.02 mol) of 4-methoxypropoxy-2-methylpyridine 1-oxide was dissolved in 50 ml of acetic anhydride to obtain a solution. This solution was stirred at 90° C. for 0.5 hour and cooled, followed by the addition of ethanol. The obtained mixture was concentrated under a reduced pressure, followed by the addition of 150 ml of 1N hydrochloric acid. The obtained mixture was stirred at 100° C. for one hour, cooled, neutralized with sodium hydrogencarbonate and, extracted with chloroform. The extract was dried over magnesium sulfate and filtered. The filtrate was distilled to remove the solvent. Thus, 3.64 g of the title compound was obtained as a crude product.

$^1$H-NMR (CDCl$_3$) δ; 1.83~2.20 (m, 2H), 3.30 (s, 3H), 3.49 ((t, J=5.3 Hz, 2H), 4.05 (t, J=5.3 Hz, 2H), 4.64 (s, 2H), 4.70 (s, 1H), 6.48~6.86 (m, 2H), 8.21 (d, J=6.2 Hz, 1H)

PREPARATIVE EXAMPLE 22

4-(3-Methoxypropoxy)-2-Methylpyridine 1-Oxide

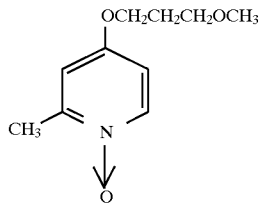

5.85 g (0.065 mol) of methoxypropanol was dissolved in 60 ml of dimethyl sulfoxide to obtain a solution. 2.6 g (0.065 mol) of sodium hydride was added to this solution at a room temperature in a nitrogen atmosphere. The obtained mixture was stirred at 60° C. for 0.5 hour. A solution of 4.66 g (0.0325 mol) of 4-chloro-2-methylpyridine 1-oxide in 20 ml of dimethyl sulfoxide was dropwise added to the mixture under cooling with ice. The mixture was stirred at 40° C. for one hour. After the completion of the reaction, the reaction mixture was concentrated under a reduced pressure to obtain a solid. 200 ml of water was added to this solid. The obtained mixture was extracted with chloroform and the obtained extract was dried over magnesium sulfate and filtered. The filtrate was concentrated under a reduced pressure and purified by silica gel column chromatography (ethyl acetate/methanol) to obtain 4.09 g of the title compound.

$^1$H-NMR (CDCl$_3$) δ; 1.80~2.24 (m, 2H), 2.48 (s, 3H), 3.31 (s, 3H), 3.48 (t, J=6.3 Hz, 2H), 4.02 (t, J=6.3 Hz, 2H), 6.50~6.78 (m, 2H), 8.04 (d, J=7.2 Hz, 1H)

PREPARATIVE EXAMPLE 23

4-Chloro-2-Methylpyridine 1-Oxide

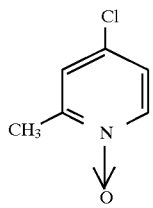

15.4 g (0.1 mol) of 2-methyl-4-nitropyridine 1-oxide was added to 78.5 g (1 mol) of acetyl chloride at −10° C. The obtained mixture was stirred under cooling with ice for 0.5 hour. After the completion of the reaction, 300 ml of ice-water was added to the reaction mixture. The obtained mixture was neutralized with sodium carbonate and extracted with chloroform. The extract was dried over magnesium sulfate and filtered. The filtrate was concentrated under a reduced pressure and purified by silica gel column chromatography (ethyl acetate/n-hexane/methanol) to obtain 4.7 g of the title compound.

$^1$H-NMR (CDCl$_3$) δ; 2.48 (s, 3H), 6.94~7.30 (m, 2H), 8.09 (d, J=7.2 Hz, 1H)

EXAMPLE 59

Sodium Salt of 2-[{4-(4-Methoxybutoxy)-3-Methylpyridine-2-Yl}Methylsulfinyl]-1H-Benzimidazole

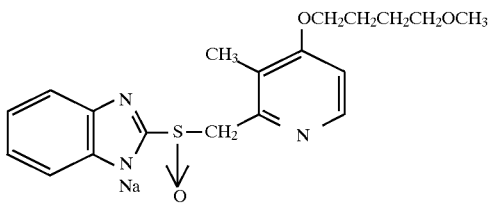

0.4 g of 2-[{4-(4-methoxybutoxy)-3-methylpyridine-2-yl}methylthio]-1H-benzimidazole was dissolved in 40 ml of dichloromethane under dehumidifying to obtain a solution. 227 mg of m-chloroperbenzoic acid was added in portions to this solution at −40° C. The obtained mixture was stirred for 30 minutes, followed by the addition of 160 mg of triethylamine. The obtained mixture was heated to −20° C., followed by the addition of 30 ml of a 2N aqueous solution of sodium carbonate. The obtained mixture was stirred for 40 minutes and extracted with dichloromethane. The extract was washed with a saturated aqueous solution of sodium hydrogencarbonate, dried over magnesium sulfate and distilled under a reduced pressure to remove the dichloromethane. Thus, 0.43 g of an oily product was obtained. This product was dissolved in a mixture comprising 11.2 ml of 0.1N aqueous sodium hydroxide and 30 ml of ethanol and the obtained solution was distilled under a reduced pressure to remove the solvent. Ethanol was added to the obtained residue and the obtained mixture was distilled under a reduced pressure to remove the solvent. The residue was crystallized from ethanol/ether to obtain 0.37 g of the title compound as a crystal.

$^1$H-NMR (DMSO-d$_6$) δ; 1.84 (m, 4H), 2.16 (s, 3H), 3.24 (s, 3H), 3.38 (t, J=6.2 Hz, 2H), 4.06 (t, J=6.2 Hz, 2H), 4.55 (ABq, J=13.2 Hz, Δν=18.1 Hz, 2H), 6.8~6.98 (m, 3H), 7.4~7.6 (m, 2H), 8.27 (d, J=5.3 Hz, 1H)

PREPARATIVE EXAMPLE 24

4-(3-Methoxypropoxy)-2,3,5-Trimethylpyridine 1-Oxide 4.5 g (0.05 mol) of methoxypropanol was dissolved in 45 ml of dimethyl sulfoxide to obtain a solution. 2.0 g of 60% sodium hydride was added to this solution at a room temperature in a nitrogen atmosphere. The obtained mixture was heated to 60° C. and stirred for one hour. After the completion of the reaction, a solution of 4.3 g (0.025 mol) of 4-chloro-2,3,5-trimethylpyridine 1-oxide in 15 ml of dimethyl sulfoxide was dropwise added to the reaction mixture at a room temperature. The obtained mixture was stirred at 60° C. for 5 hours, cooled and distilled to dryness to remove the solvent. 200 ml of water was added to the obtained residue. The obtained mixture was extracted with 150 ml of chloroform five times. The extract was dried over magnesium sulfate and filtered. The filtrate was distilled to remove the solvent. The residue was purified by silica gel column chromatography (ethyl acetate/n-hexane) to obtain 4.27 g of the title compound as an oil.

PREPARATIVE EXAMPLE 25

2-Hydroxymethyl-4-(3-Methoxypropoxy)-3,4-Dimethylpyridine

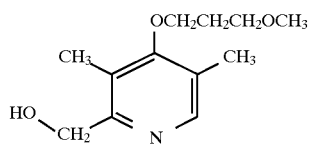

4.25 g (0.019 mol) of 4-(3-methoxypropoxy)-2,3,5-trimethylpyridine 1-oxide was dissolved in 40 ml of acetic anhydride to obtain a solution. This solution was stirred at 100° C. for 30 minutes, cooled and distilled to remove the solvent. Thus, an oil was obtained. 50 ml of 1N hydrochloric acid was added to the oil. The obtained mixture was stirred at 100° C. for one hour, cooled, neutralized with sodium hydrogencarbonate and extracted with 150 ml of chloroform thrice. The extract was dried over magnesium sulfate and filtered. The filtrate was distilled to remove the solvent. The obtained residue was dried in a vacuum to obtain 4.70 g of the title compound as a crude oil.

$^1$H-NMR (CDCl$_3$) δ; 1.80~2.28 (m, 2H), 2.08 (s, 3H), 2.23 (s, 3H), 3.34 (s, 3H), 3.58 (t, J=6.2 Hz, 2H), 3.87 (t, J=6.2 Hz, 2H), 4.57 (s, 2H), 8.10 (s, 1H)

PREPARATIVE EXAMPLE 26

2-Chloromethyl-4-(3-Methoxypropoxy)-3,5-Dimethylpyridine

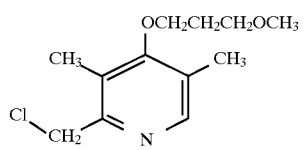

4.70 g of crude 2-hydroxymethyl-4-(3-methoxypropoxy)-3,5-dimethylpyridine was dissolved in 50 ml of chloroform to obtain a solution. A solution of 2.7 g of thionyl chloride in 10 ml of chloroform was dropwise added to the above solution at 0° C. and the obtained mixture was stirred at 0° C. for one hour. After the completion of the reaction, the reaction mixture was neutralized with a saturated aqueous solution of sodium hydrogencarbonate and extracted with 150 ml of chloroform twice. The extract was dried over magnesium sulfate and filtered. The filtrate was distilled to remove the solvent. The obtained residue was dried in a vacuum to obtain 4.52 g of the title compound as a crude oil.

$^1$H-NMR (CDCl$_3$) δ; 1.70~2.20 (m, 2H), 2.26 (s, 3H), 2.34 (s, 3H), 3.38 (s, 3H), 3.61 (t, J=6.2 Hz, 2H), 3.91 (t, J=6.2 Hz, 2H), 4.67 (s, 2H), 8.18 (s, 1H)

EXAMPLE 60

2-[4-(3-Methoxypropoxy)-3,4-Dimethylpyridine-2-Yl]Methylthio-1H-Benzimidazole

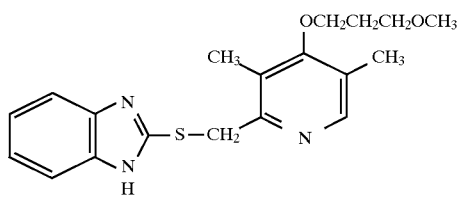

A mixture comprising 2.25 g (0.015 mol) of 2-mercaptobenzimidazole, 4.52 g (0.0185 mol) of 2-chloromethyl-4-(3-methoxypropoxy)-3,5-dimethylpyridine, 0.63 g (0.015 mol) of 95% sodium hydroxide and 50 ml of ethanol was stirred at 40° C. for 6 hours. After the completion of the reaction, the reaction mixture was distilled to remove the solvent. The residue was purified by silica gel column chromatography (ethyl acetate/n-hexane) to obtain 4.62 g of the title compound as a pale yellow oil.

EXAMPLE 61

Sodium Salt of 2-[4-(3-Methoxypropoxy)-3,4-Dimethylpyridine-2-Yl]Methylsulfinyl-1H-Benzimidazole

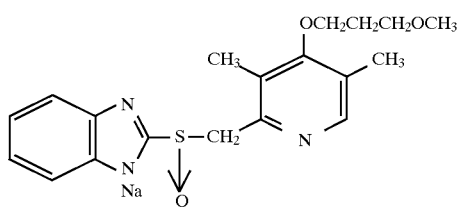

1.5 g of 2-[4-(3-methoxypropoxy)-3,4-dimethylpyridine-2-yl]methylthio-1H-benzimidazole was dissolved in 80 ml of dichloromethane under dehumidifying to obtain a solution. 870 mg of m-chloroperbenzoic acid was added to the solution in portions at −40° C. The obtained mixture was stirred for 30 minutes, followed by the addition of 599 mg of triethylamine. The obtained mixture was heated to −20° C., followed by the addition of 80 ml of a 2N aqueous solution of sodium carbonate. The obtained mixture was stirred for one hour and extracted with dichloromethane. The extract was washed with a saturated aqueous solution of sodium hydrogencarbonate, dried over magnesium sulfate and distilled under a reduced pressure to obtain 1.4 g of a crystal. 800 mg of the crystal was dissolved in a mixture comprising 21.4 ml of 0.1N aqueous sodium hydroxide and ethanol. The obtained solution was distilled under a reduced pressure to remove the solvent. The obtained residue was dissolved in ethanol and the solution was distilled under a reduced pressure to remove the solvent. The obtained residue was crystallized from ethanol/ether to obtain 800 mg of a crystal.

$^1$H-NMR (DMSO-d$_6$) δ; 1.94 (qui, J=6.2 Hz, 2H), 2.17 (s, 3H), 2.19 (s, 3H), 3.25 (s, 3H), 3.51 (t, J=6.6 Hz, 2H), 3.80 (t, J=6.6 Hz, 2H), 4.51 (ABq, J=13.2 Hz, Δv=17.0 Hz), 6.8~6.9 (m, 2H), 7.4~7.7 (m, 2H), 8.21 (s, 1H)

EXAMPLE 62

2-[4-[3-{(2-Methoxyethoxy)Methoxy}Propoxy]-3-Methylpyridine-2-Yl]Methylthio-1H-Benzimidazole

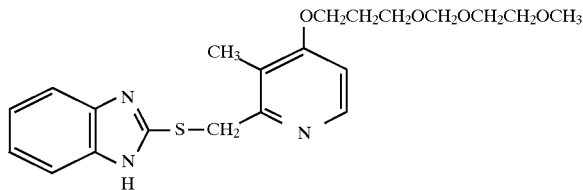

1.8 g of 2-hydroxymethyl-4-[3-{(2-methoxyethoxy)methoxy}propoxy]-3-methylpridine was dissolved in 40 ml of dichloromethane under dehumidifying to obtain a solution, followed by the addition of 2.47 g of triethylamine. 1.4 g of methanesulfonyl chloride was added to the obtained mixture in portions under cooling with ice. The obtained mixture was stirred for 30 minutes, made basic with a saturated aqueous solution of carbonic acid and extracted with chloroform. The extract was dried over magnesium sulfate and distilled under a reduced pressure. The residue was dissolved in 30 ml of ethanol, followed by the addition of 917 mg of 2-mercapto-1H-benzimidazole and 367 mg of sodium hydroxide. The obtained mixture was stirred at a room temperature for 30 minutes and distilled under a reduced pressure to remove the ethanol. The obtained residue was chromatographed over a silica gel column and eluted with ethyl acetate/n-hexane to obtain 2.1 g of the title thio ether compound.

$^1$H-NMR (CDCl$_3$) δ; 2.11 (qui, J=6.2 Hz, 2H), 2.25 (s, 3H), 3.35 (s, 3H), 3.58 (m, 4H), 3.75 (t, J=6.2 Hz, 2H), 4.13 (t, J=6.2 Hz, 2H), 4.38 (s, 2H), 4.71 (s, 2H), 6.75 (d, J=5.7 Hz, 1H), 7.1~7.3 (m, 2H), 7.4~7.6 (m, 2H), 8.32 (d J=5.7 Hz, 1H)

EXAMPLE 63

Sodium Salt of 2-[4-[3-{(2-Methoxyethoxy)Methoxy}Propoxy]-3-Methylpyridine-2-Yl]Methylsulfinyl-1H-Benzimidazole

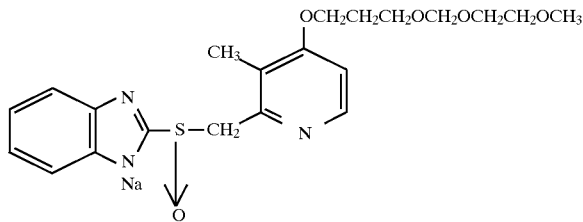

1.1 g of 2-[4-[3-{(2-methoxyethoxy)methoxy}propoxy]-3-methylpyridine-2-yl]methylthio-1H-benzimidazole was dissolved in 80 ml of dichloromethane under dehumidifying to obtain a solution. 544 mg of m-chloroperbenzoic acid was added to this solution in portions at –40° C. The obtained mixture was stirred for 30 minutes, followed by the addition of 379 mg of triethylamine. The obtained mixture was heated to –20° C., followed by the addition of 40 ml of a 2N aqueous solution of sodium carbonate. The obtained mixture was stirred fro 30 minutes and-extracted with chloroform. The extract was washed with a saturated aqueous solution of sodium hydrogencarbonate, dried over magnesium sulfate and distilled under a reduced pressure to remove the solvent.

The obtained residue was dissolved in a mixture comprising 24 ml of 0.1N aqueous sodium hydroxide and 40 ml of ethanol. The obtained solution was distilled under a reduced pressure to remove the solvent, followed by the addition of 40 ml of ethanol. The obtained mixture was again distilled under a reduced pressure to remove the ethanol. The residue was crystallized from ethanol/ether to obtain 0.98 g of the title compound.

$^1$H-NMR (DMSO-d$_6$) δ; 2.02 (qui, J=6.2 Hz, 2H), 2.17 (s, 3H), 3.23 (s, 3H), 3.49 (m, 4H), 3.65 (t, J=6.21 Hz, 2H), 4.12 (t, J=6.2 Hz, 2H), 4.56 (ABq, J=21.1 Hz, Δν=16.8 Hz, 2H), 4.62 (s, 2H), 6.84~6.99 (m, 3H), 7.4~7.5 (m, 2H), 8.28 (d, J=5.7 Hz, 1H)

PREPARATIVE EXAMPLE 27

4-(2-Fluoromethoxy)Ethoxy-2,3-Dimethylpyridine N-Oxide

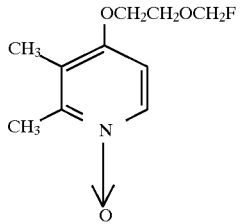

0.49 g of sodium hydride was gradually added to a solution of 1.0 g of 4-(2-hydroxyethoxy)-2,3-dimethylpyridine N-oxide in 40 ml of dimethylformamide in a nitrogen atmosphere at a room temperature. After the stopping of foaming, 1 ml of bromofluoromethane was added to the obtained mixture at –50° C. The resulting mixture was gradually heated and stirred at 15° to 20° C. for 3 hours. Ethanol was added to the resulting mixture to consume excess sodium hydride. 5 ml of 1N aqueous hydrochloric acid was added to the mixture and gaseous nitrogen was passed through the obtained mixture to expel excess bromofluoromethane. Water was added to the resulting mixture. The obtained mixture was extracted with chloroform and the extract was dried over magnesium sulfate and distilled under a reduced pressure to remove the solvent. The residue was chromatographed over a silica gel column and eluted with chloroform containing 1 to 5% of methanol to obtain 0.6 g of the title compound.

1H-NMR (CDCl$_3$) δ; 2.24 (s, 3H), 2.56 (s, 3H), 4.24 (m, 5H), 5.3 (d, J=55.8 Hz, 2H), 6.54 (d, J=6.2 Hz, 1H), 8.12 (d, J=6.2 Hz, 1H)

PREPARATIVE EXAMPLE 28

4-(2-Fluoromethoxy)Ethoxy-2-Hydroxymethyl-3-Methylpyridine

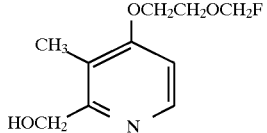

A mixture comprising crude 4-(2-fluoromethoxy)ethoxy-2,3-dimethylpyridine N-oxide prepared from 6.0 g of crude 4-(2-hydroxyethoxy)-2,3-dimethylpyridine N-oxide and 40 ml of acetic anhydride was stirred under heating at 90° to 100° C. for 40 minutes and distilled under a reduced pressure to remove the acetic anhydride. The residue was made weakly basic with a 2N aqueous solution of sodium carbonate and extracted with chloroform. The extract was dried over magnesium sulfate and distilled under a reduced pressure to remove the solvent. The obtained residue was dissolved in 30 ml of ethanol, followed by the addition of 0.38 g of sodium hydroxide. The obtained mixture was stirred at a room temperature for 30 minutes, made weakly basic with a saturated aqueous solution of ammonium chloride and extracted with chloroform. The extract was dried over magnesium sulfate and distilled under a reduced pressure to remove the solvent. The residue was chromatographed over a silica gel column and eluted with ethyl acetate/n-hexane to obtain 1.2 g of the title compound as a crystal.

$^1$H-NMR (CDCl$_3$) δ; 2.06 (s, 3H), 4.17 (m, 4H), 4.64 (s, 2H), 5.35 (d, J=56.3 Hz, 2H), 6.71 (d, J=5.7 Hz, 1H), 8.30 (d, J=5.7 Hz, 1H)

PREPARATIVE EXAMPLE 29

{4-(2-Fluoromethoxy)Ethoxy-3-Methylpyridine-2-Yl}-Methyl Methanesulfonate

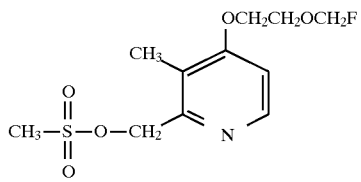

160 mg of methanesulfonyl chloride was dropwise added to a solution of 0.2 g of 4-(2-fluoromethoxy)ethoxy-2-hydroxymethyl-3-methylpyridine and 143 mg of triethylamine in 10 ml of chloroform under dehumidifying at −50° C. The obtained mixture was gradually heated to a room temperature, made basic with a saturated aqueous solution of sodium hydrogencarbonate and extracted with chloroform. The extract was dried over magnesium sulfate and distilled to remove the solvent. 0.38 g of the title compound was obtained as a crude oil.

$^1$H-NMR (CDCl$_3$) δ; 2.30 (s, 3H), 3.08 (s, 3H), 4.2 (m, 4H), 5.4 (d, J=55.8 Hz, 2H), 5.38 (s, 2H), 6.84 (d, J=6 Hz, 1H), 8.36 (d, J=6 Hz, 1H)

EXAMPLE 64

2-[{4-(2-Fluoromethoxy)Ethoxy-3-Methylpyridine-2-Yl}-Methylthio]-1H-Benzimidazole

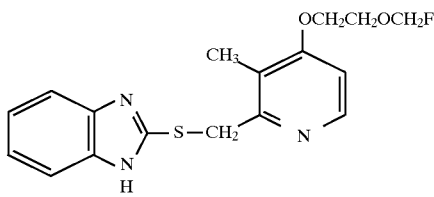

A mixture comprising crude {4-(2-fluoromethoxy)ethoxy-3-methylpyridine-2-yl}methyl methanesulfonate prepared from 0.6 g of 4-(2-fluoromethoxy)ethoxy-2-hydroxymethyl-3-methylpyridine, 0.42 g of 2-mercapto-1H-benzimidazole and 30 ml of ethanol was stirred at a room temperature for 30 minutes and distilled under a reduced pressure to remove the ethanol. The obtained residue was chromatographed over a silica gel column and eluted with methanol/ethyl acetate to obtain 0.3 g of an oily product.

$^1$H-NMR (CDCl$_3$) δ; 2.25 (s, 3H), 2.98 (s, 3H), 4.13 (m, 4H), 4.41 (s, 2H), 5.33 (d, J=56.3 Hz, 2H), 6.72 (d, J=5.7 Hz, 1H), 7.1~7.2 (m, 2H), 7.4~7.6 (m, 2H), 8.32 (d, J=5.7 Hz, 1H)

EXAMPLE 65

Sodium Salt of 2-[{4-(2-Fluoromethoxy)Ethoxy-3-Methylpyridine-2-Yl}Methylsulfinyl]-1H-Benzimidazole

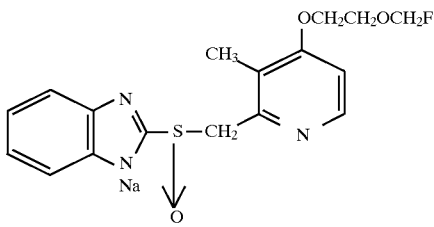

184 mg of m-chloroperbenzoic acid was added in portions to a solution of 0.3 g of 2-[{4-(2-fluoromethoxy)ethoxy-3-methylpyridine-2-yl}methylthio]-1H-benzimidazole in 30 ml of dichloromethane under stirring and dehumidifying at −40° C. The obtained mixture was stirred for 30 minutes, followed by the addition of 129 mg of triethylamine. The obtained mixture was brought to a room temperature, made weakly basic with a saturated aqueous solution of sodium hydrogencarbonate and extracted with chloroform. The extract was dried over magnesium sulfate and distilled under a reduced pressure to remove the solvent. The obtained residue was dissolved in 30 ml of anhydrous tetrahydrofuran in a nitrogen atmosphere to obtain a solution. 36.2 mg of 60% sodium hydride was added to this solution at −20° C. After the disappearance of foams, the obtained mixture was distilled under a reduced pressure to remove the tetrahydrofuran. The residue was crystallized from anhydrous ether to obtain 260 mg of the title compound as a crystal.

$^1$H-NMR (DMSO-d$_6$) δ; 2.18 (s, 3H), 4.14 (m, 4H), 4.56 (ABq, J=13.2 Hz, Δv=21.3 Hz, 2H), 5.37 (d, J=56.7 Hz, 2H), 6.8~7.0 (m, 3H), 7.4~7.5 (m, 2H), 8.29 (d, J=5.3 Hz, 1H)

EXAMPLE 66

2-[[4-{2-(1H-Benzimidazol-2-Ylthio)Ethoxy}-3-Methylpyridine-2-Yl]Methylthio]-1H-Benzimidazole

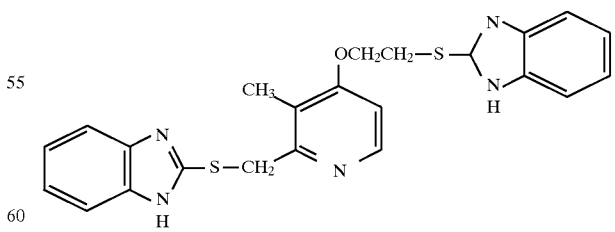

A mixture comprising 1.34 g (0.004 mol) of 2-[{4-(2-chloroethoxy)-3-methylpyridine-2-yl}methylthio]-1H-benzimidazol, 0.53 g (0.0035 mol) of 2-mercapto-1H-benzimidazole, 0.17 g (0.004 mol) of 95% sodium hydroxide and 30 ml of ethanol was stirred at 80° C. for 8 hours. After the completion of the reaction, the reaction mixture was filtered to remove inorganic matter. The filtrate was distilled to remove the solvent. The residue was purified by silica gel column chromatography (ethyl acetate/n-hexane) to obtain 1.08 g of the title compound as a white crystal.

$^1$H-NMR (DMSO-d$_6$) δ; 2.15 (s, 3H), 3.73 (t, J=7.1 Hz, 2H), 4.23 (t, J=7.1 Hz, 2H), 4.68 (s, 2H), 6.96~7.22 (m, 5H), 7.32~7.54 (m, 4H), 8.25 (d, J=5.3 Hz, 1H)

EXAMPLE 67

Disodium Salt of 2-[[4-{2-(1H-Benzimidazol-2-Ylsulfinyl)Ethoxy}-3-Methylpyridine-2-Yl]Methylsulfinyl]-1H-Benzimidazole

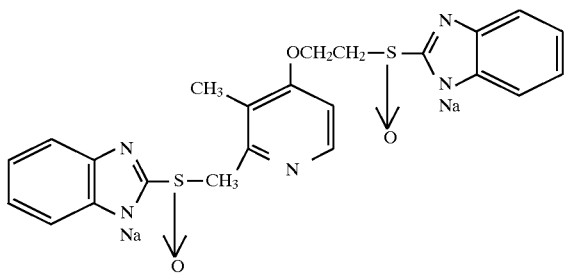

0.90 g (0.002 mol) of 2-[[4-(2-(1H-benzimidazol-2-ylthio)ethoxy}-3-methylpyridine-2-yl]methylthio]-1H benzimidazole was suspended in 40 ml of dichloromethane to obtain a suspension. Methanol was added to the suspension, until the suspension became transparent. 0.43 g (0.002 mol) of 80% m-chloroperbenzoic acid was added to the resulting mixture in a nitrogen atmosphere at −60° C. The obtained mixture was stirred for 0.5 hour. After the completion of the reaction, 0.5 g of triethylamine was added to the reaction mixture. The obtained mixture was heated to −10° C., followed by the addition of 30 ml of a saturated aqueous solution of sodium hydrogencarbonate. The obtained mixture was stirred at a room temperature for 0.5 hour and filtered. The filtrate was extracted with 100 ml of dichloromethane thrice. The extract was dried over magnesium sulfate and filtered. The filtrate was distilled to remove the solvent. 0.14 g of the obtained residue was dissolved in 0.1N aqueous sodium hydroxide, followed by the addition of ethanol. The obtained mixture was distilled to remove the solvent. The obtained residue was washed with ether to obtain 0.15 g of the title compound as a yellow crystal.

$^1$H-NMR (DMSO-d$_6$) δ; 2.18 (s, 3H), 3.20~3.75 (m, 2H), 4.19~4.74 (m, 4H), 6.68~7.08 (m, 5H), 7.16~7.53 (m, 4H), 8.20 (d, J=6.2 Hz, 1H)

EXAMPLE 68

2-[[4-{2-(Benzothianol-2-Ylthio)Ethoxy}-3-Methylpyridine-2-Yl]Methylthio]-1H-Benzimidazole

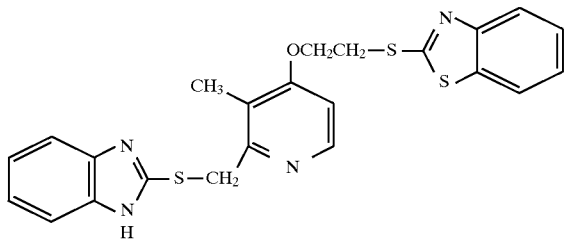

A mixture comprising 1.34 g (0.004 mol) of 2-[{4-(2-chloroethoxy)-3-methylpyridine-2-yl}methylthio]-1H-benzimidazole, 0.59 g (0.0035 mol) of 2-mercaptobenzothiazole, 0.17 g (0.004 mol) of 95% sodium hydroxide and 30 ml of ethanol was stirred at 80° C. for 16 hours. After the completion of the reaction, the reaction mixture was filtered to remove inorganic matter. The filtrate was distilled to remove the solvent and the residue was purified by silica gel column chromatography (ethyl acetate/n-hexane) to obtain 1.20 g of the title compound as a white crystal.

$^1$H-NMR (DMSO-d$_6$) δ; 2.08 (s, 3H), 3.79 (t, J=6.2 Hz, 2H), 4.40 (t, J=6.2 Hz, 2H), 4.60 (s, 2H), 6.88~7.21 (m, 3H), 7.22~7.50 (m, 4H), 7.68~8.02 (m, 2H), 8.16 (d, J=6.2 Hz, 1H)

EXAMPLE 69

Sodium Salt of 2-[[4-{2-(Benzothiazol-2-Ylsulfinyl)Ethoxy}-3-Methylpyridine-2-Yl]Methylsulfinyl]-1H-Benzimidazole

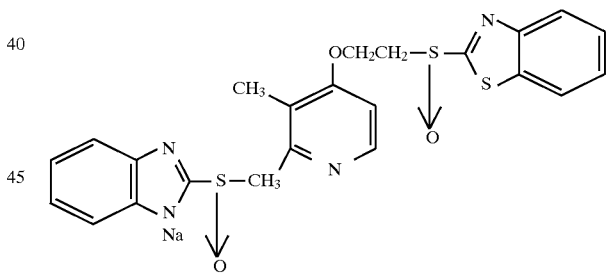

0.93 g (0.002 mol) of 2-[[4-{2-(benzothiazol-2-ylthio)ethoxy}-3-methylpyridine-2-yl]methylthio]-1H-benzimidazole was suspended in 40 ml of dichloromethane. Methanol was added to the obtained suspension until the suspension became transparent. 0.43 g of 80% m-chloroperbenzoic acid was added to the resulting mixture in a nitrogen atmosphere at −60° C. The obtained mixture was stirred for 0.5 hour. After the completion of the reaction, 0.6 g of triethylamine was added to the reaction mixture and the obtained mixture was heated to −10° C., followed by the addition of 30 ml of a saturated aqueous solution of sodium hydrogencarbonate. The obtained mixture was stirred at a room temperature for 0.5 hour and extracted with 100 ml of dichloromethane twice. The extract was dried over magnesium sulfate and filtered. The filtrate was distilled to remove the solvent. 0.8 g of the obtained residue was dissolved in 0.1N aqueous sodium hydroxide, followed by the addition of ethanol. The obtained mixture was distilled to remove the solvent. The obtained residue was washed with ether to obtain 0.69 g of the title compound.

$^1$H-NMR (DMSO-d$_6$) δ; 2.06 (s, 3H), 3.66~4.00 (m, 2H), 4.19~4.86 (m, 4H), 6.74~7.04 (m, 3H), 7.15~7.54 (m, 4H), 7.64~7.96 (m, 2H), 8.21 (d, J=6.2 Hz, 1H)

The following compounds of Examples 70 to 91 were prepared in a similar manner to those described above.

EXAMPLE 70

2-[{4-(2-Furanylmethylsulfinyl)Ethoxy-3-Methylpyridine-2-Yl}Methylsulfinyl]-1H-Benzimidazole

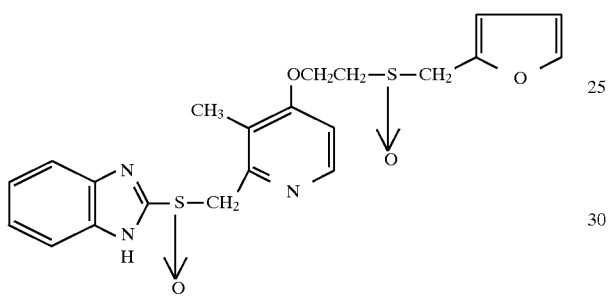

$^1$H-NMR (DMSO-d$_6$) δ; 2.36 (s, 3H), 3.0~3.5 (m, 2H), 4.0~4.6 (m 4H), 4.73 (s, 2H), 6.44 (s, 2H), 7.02 (d, J=5.4 Hz, 1H), 7.16~7.2 (m, 2H), 7.28~7.76 (m, 3H), 8.24 (d, J=5.4 Hz, 1H)

EXAMPLE 71

2-[{4-(2-(1,1-Dioxothiomorpholino))Ethoxy-3-Methylpyridine-2-Yl}Methylthio]-1H-Benzimidazole

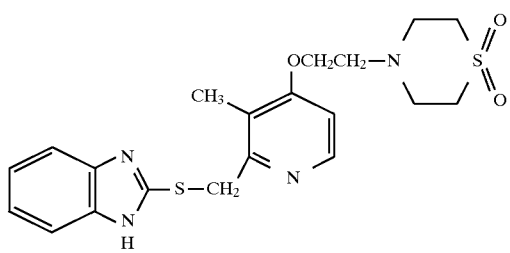

$^1$H-NMR (DMSO-d$_6$) δ; 2.21 (s, 3H), 2.99 (t, J=5.8 Hz, 2H), 3.07 (s, 8H), 4.16 (t, J=5.8 Hz, 2H), 4.68 (s, 2H), 6.95 (d, J=6.1 Hz, 1H), 6.95~7.2 (m, 2H), 7.3~7.5 (m, 2H), 8.23 (d, J=6.1 Hz, 1H)

EXAMPLE 72

2-[{3-Methyl-4-(2-Methylfulfonyl)Ethoxy}Pyridine-2-Yl]Methylthio-1H-Benzimidazole

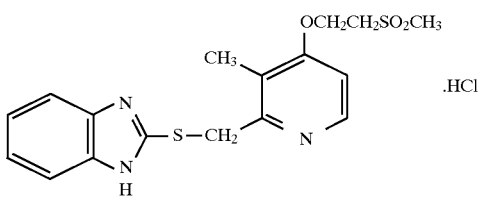

$^1$H-NMR (DMSO-d$_6$) δ; 2.28 (s, 3H), 3.08 (s, 3H), 3.72 (t, J=6.2 Hz, 2H), 3.66 (t, J=6.2 Hz, 2H), 3.94 (s, 2H), 6.8~7.6 (m, 7H), 8.6 (d, J=5.7 Hz, 1H)

EXAMPLE 73

2-[{4-(2-Ethoxycarbonyl)Methoxy)Ethoxy-3-Methylpyridine-2-Yl}Methylsulfinyl]-1H-Benzimidazole

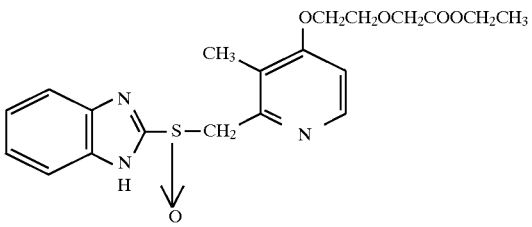

$^1$H-NMR (DMSO-d$_6$) δ; 1.2 ((t, J=7.2 Hz, 3H), 2.16 (s, 3H), 3.76~4.32 (m, 8H), 4.73 (s, 2H), 6.94 (d, J=5.4 Hz, 1H), 7.12~7.4 (m, 2H), 7.5~7.7 (m, 2H), 8.22 (d, J=5.4 Hz, 1H)

EXAMPLE 74

[{4-(2-Ethoxycarbonylsulfinyl)Ethoxy-3-Methylpyridine 2-Yl}Methylsulfinyl]-1H-Benzimidazole

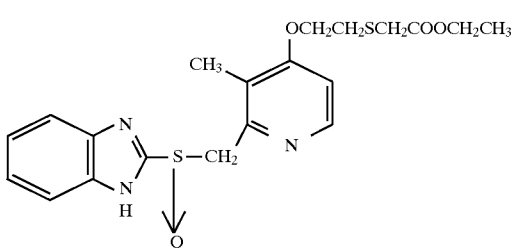

$^1$H-NMR (DMSO-d$_6$) δ; 1.22 (t, J=7.2 Hz, 3H), 2.16 (s, 3H), 3.16~3.56 (m, 2H), 3.64~4.6 (m, 6H), 4.76 (s, 2H), 7.04 (d, J=7 Hz, 1H), 7.16~7.24 (m, 2H), 7.32~7.80 (m, 2H), 8.24 (d, J=7 Hz, 1H)

EXAMPLE 75

2-[[3-Methyl-4-{(2-Phenylthio)Ethoxy}Pyridine-2-Yl]-Methylthio]-1H-Benzimidazole

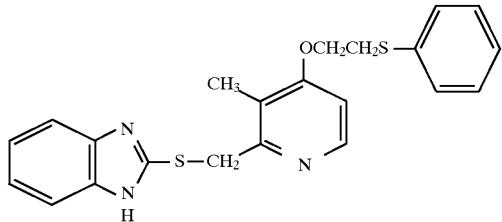

$^1$H-NMR (CDCl$_3$) δ; 2.08 (s, 3H), 3.24 (t, J=6.1 Hz, 2H), 4.06 (t, J=6.1 Hz, 2H), 4.38 (s, 2H), 6.52 (d, J=5.8 Hz, 1H), 7.04~7.64 (m, 10H), 8.23 (d, J=5.8 Hz, 1H)

EXAMPLE 76

2-[[3-Methyl-4-{(2-Pyridylthio)Ethoxy}Pyridine-2-Yl]-Methylthio]-1H-Benzimidazole

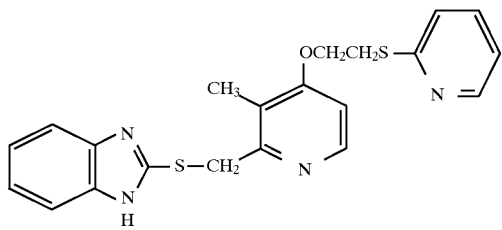

$^1$H-NMR (DMSO-d$_6$) δ; 2.14 (s, 3H), 3.6 (t, J=6.1 Hz, 2H), 4.32 (t, J=6.1 Hz, 2H), 4.7 (s, 2H), 7.0~7.8 (m, 10H), 8.2~8.6 (m, 2H)

EXAMPLE 77

2-[[3-Methyl-4-{(2-Methylsulfinyl)Ethoxy}Pyridine-2-Yl]Methylsulfinyl]-1H-Benzimidazole

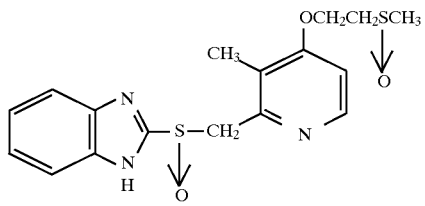

$^1$H-NMR (DMSO-d$_6$) δ; 2.16 (s, 3H), 2.64 (s, 3H), 3.16 (m, 2H), 4.44 (m, 2H), 4.78 (s, 2H), 7.0 (d, J=5.8 Hz, 1H), 7.4~7.5 (m, 2H), 7.5~7.7 (m, 2H), 8.2 (d, J=5.8 Hz, 1H)

EXAMPLE 78

2-[4-{(2-Benzylthio)Ethoxy}-3-Methylpyridine-2-Yl]-Methylthio]-1H-Benzimidazole

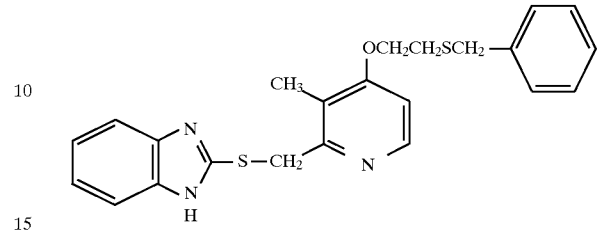

$^1$H-NMR (DMSO-d$_6$) δ; 2.24 (s, 3H), 2.84 (t, J=5.8 Hz, 2H), 4.18 (t, J=5.8 Hz, 2H), 4.68 (s, 2H), 6.86 (d, J=6.5 Hz, 1H), 7.0~7.54 (m, 9H), 8.23 (d, J=6.5 Hz, 1H)

EXAMPLE 79

2-[{4-(2-Methoxy)Propoxy-3-Methylpyridine-2-Yl}Methylsulfonyl]- 1H-Benzimidazole

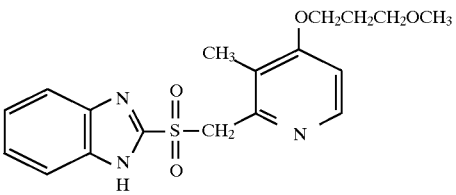

$^1$H-NMR (DMSO-d$_6$) δ; 2.0 (t, J=7.5 Hz, 2H), 2.2 (s, 3H), 3.28 (s, 3H), 3.5 (t, J=7.5 Hz, 2H), 4.09 (t, J=7.5 Hz, 2H), 5.06 (s, 2H), 6.92 (d, J=5.4 Hz, 1H), 7.35~7.52 (m, 2H), 7.64~7.8 (m, 2H), 8.03 (d, J=5.4 Hz, 1H)

EXAMPLE 80

5-Methoxy-2-{4-(3-Methoxypropoxy)-3-Methylpyridine-2-Yl}Methylthio-1H-Benzimidazole

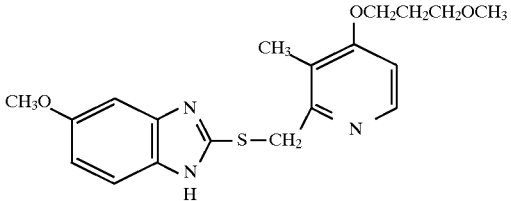

$^1$H-NMR (CDCl$_3$) δ; 1.92~2.18 (m, 2H), 2.22 (s, 3H), 3.31 (s, 3H), 3.52 (t, J=6.1 Hz, 2H), 3.80 (s, 3H), 4.09 (t, J=6.1 Hz, 2H), 4.30 (s, 2H), 6.64~6.81 (m, 2H), 6.97 (d, J=2.2 Hz, 1H), 7.33 (d, J=8.5 Hz), 8.25 (d, J=5.7 Hz, 1H)

EXAMPLE 81

5-Methyl-2-{4-(3-Methoxypropoxy)-3-Methylpyridine-2-Yl}Methylthio-1H-Benzimidazole

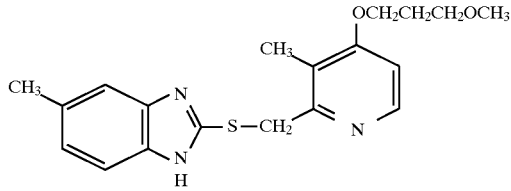

$^1$H-NMR (CDCl$_3$) δ; 1.94~2.19 (m, 2H), 2.22 (s, 3H), 2.42 (s, 3H), 3.31 (s, 3H), 3.52 (t, J=6.1 Hz, 2H), 4.08 (t, J=6.1 Hz, 2H), 4.31 (s, 2H), 6.67 (d, J=5.7 Hz, 1H), 6.80~7.00 (m, 1H), 7.15~7.40 (m, 2H), 8.23 (d, J=5.7 Hz, 1H)

EXAMPLE 82

5,6-Dimethyl-2-{4-(3-Methoxypropoxy)-3-Methylpyridine-2-Yl}Methylthio-1H-Benzimidazole

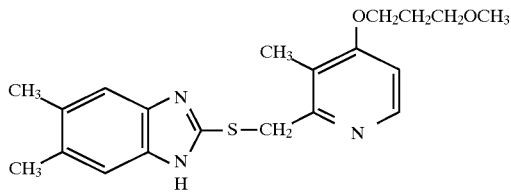

$^1$H-NMR (CDCl$_3$) δ; 1.95~2.17 (m, 2H), 2.24 (s, 3H), 2.34 (s, 6H), 3.35 (s, 3H), 3.55 (t, J=6.2 Hz, 2H), 4.12 (t, J=6.2 Hz, 2H), 4.35 (s, 2H), 6.74 (d, J=5.7 Hz), 7.29 (s, 2H), 8.32 (d, J=5.7 Hz)

EXAMPLE 83

5-Chloro-2-{4-(3-Methoxypropoxy)-3-Methylpyridine-2-Yl}Methylthio-1H-Benzimidazole

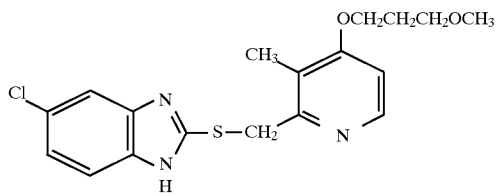

$^1$H-NMR (CDCl$_3$) δ; 1.93~2.18 (m, 2H), 2.25 (s, 3H), 3.35 (s, 3H), 3.56 (t, J=6.2 Hz, 2H), 4.13 (t, J=6.2 Hz, 2H), 4.36 (s, 2H), 6.76 (d, J=5.7 Hz, 1H), 7.10 (dd, J=8.8 Hz, 2.2 Hz, 1H), 7.42 (d, J=8.8 Hz, 1H), 7.50 (d, J=2.2 Hz, 1H), 8.31 (d, J=5.7 Hz, 1H)

EXAMPLE 84

2-{4-(3-Methoxypropoxy)-3-Methylpyridine-2-Yl}Methylthio-5-Trifluoromethyl-1H-Benzimidazole

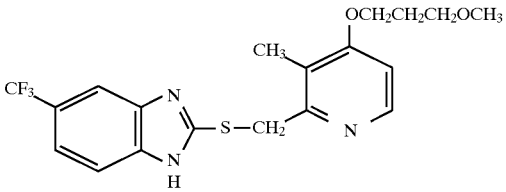

$^1$H-NMR (CDCl$_3$) δ; 1.92~2.19 (m, 2H), 2.27 (s, 3H), 3.36 (s, 3H), 3.56 (t, J=5.9 Hz, 2H), 4.15 (t, J=6.1 Hz, 2H), 4.38 (s, 2H), 6.79 (d, J=5.7 Hz, 1H), 7.23~7.60 (m, 2H), 7.71 (s, 1H), 8.35 (d, J=5.7 Hz, 1H)

EXAMPLE 85

Sodium Salt of 5-Methoxy-2-{4-(3-Methoxypropoxy)-3-Methylpyridine-2-Yl}Methylsulfinyl-1H-Benzimidazole

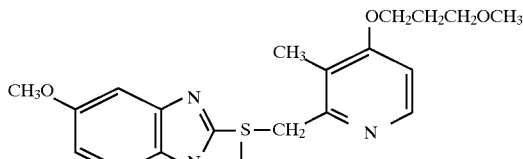

$^1$H-NMR (DMSO-d$_6$) δ; 1.84~2.06 (m, 2H), 2.14 (s, 3H), 3.25 (s, 3H), 3.49 (t, J=6.2 Hz, 2H), 3.72 (s, 3H), 4.09 (t, J=6.2 Hz, 2H), 4.53 (ABq, J=12.7 Hz, Δv=18.0 Hz, 2H), 6.54 (dd, J=8.8 Hz, 2.6 Hz, 1H), 6.91 (d, J=5.7 Hz, 1H), 7.00 (d, J=2.6 Hz, 1H), 7.34 (d, J=8.8 Hz, 1H), 8.27 (d, J=5.7 Hz, 1H)

EXAMPLE 86

Sodium Salt of 5-Methyl-2-{4-(3-Methoxypropoxy)-3-Methylpyridine-2-Yl}Methylsulfinyl-1H-Benzimidazole

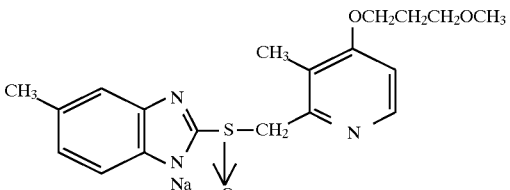

$^1$H-NMR (DMSO-d$_6$) δ; 1.84~2.05 (m, 2H), 2.14 (s, 3H), 2.37 (s, 3H), 3.25 (s, 3H), 3.48 (t, J=6.2 Hz, 2H), 4.09 (t, J=6.2 Hz, 2H), 4.53 (ABq, J=12.8 Hz, Δv=17.3 Hz, 2H), 6.71 (dd, J=7.9 Hz, 1.5 Hz, 1H), 6.91 (d, J=5.7 Hz, 1H), 7.26 (s, 1H), 7.35 (d, J=7.9 Hz, 1H), 8.27 (d, J=5.7 Hz, 1H)

EXAMPLE 87

Sodium Salt of 5,6-Dimethyl-2-{4-(3-Methoxyporpoxy)-3-Methylpyridine-2-Yl}Methylsulfinyl-1H-Benzimidazole

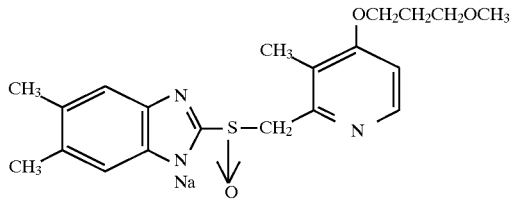

$^1$H-NMR (DMSO-d$_6$) δ; 1.82~2.08 (m, 2H), 2.13 (s, 3H), 2.27 (s, 6H), 3.24 (s, 3H), 3.47 (t, J=6.6 Hz, 2H), 4.08 (t, J=6.7 Hz, 2H), 4.54 (ABq, J=13.0 Hz, Δv=19.8 Hz, 2H), 6.90 (d, J=5.7 Hz, 1H), 7.25 (s, 2H), 8.26 (d, J=5.7 Hz, 1H)

EXAMPLE 88

Sodium Salt of 5-Chloro-2-{4-(3-Methoxypropoxy)-3-Methylpyridine-2-Yl}Methylsulfinyl-1H-Benzimidazole

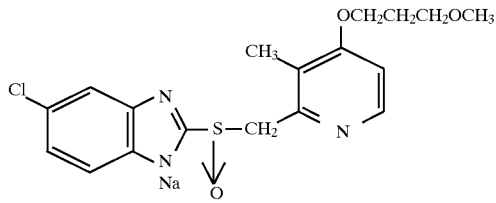

$^1$H-NMR (DMSO-d$_6$) δ; 1.80~2.06 (m, 2H), 2.13 (s, 3H), 3.25 (s, 3H), 3.48 (t, J=6.2 Hz, 2H), 4.09 (t, J=6.2 Hz, 2H), 4.54 (ABq, J=12.9 Hz, Δv=15.3 Hz, 2H), 6.65~6.92 (m, 2H), 7.25~7.50 (m, 2H), 8.27 (d, J=5.3 Hz)

EXAMPLE 89

Sodium Salt of 2-{4-(3-Methoxypropoxy)-3-Methylpyridine-2-Yl}Methylsulfinyl-5-Trifluoromethyl-1H-Benzimidazole

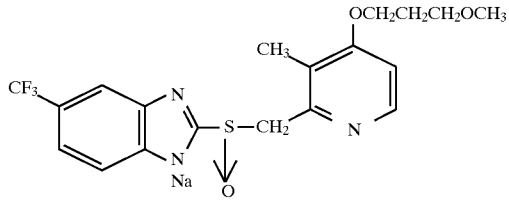

$^1$H-NMR (DMSO-d$_6$) δ; 1.84~2.06 (m, 2H), 2.14 (s, 3H), 3.25 (s, 3H), 3.48 (t, J=6.2 Hz, 2H), 4.09 (t, J=6.1 Hz, 2H), 4.56 (ABq, J=13.2 Hz, Δv=13.5 Hz, 2H), 6.92 (d, J=5.3 Hz, 1H), 7.01~7.22 (m, 1H), 7.45~7.82 (m, 2H), 8.21 (d, J=5.3 Hz, 1H)

EXAMPLE 90

2-{4-(3-Methoxypropoxy)-5-Methylpyridine-2-Yl}Methylthio-1H-Benzimidazole

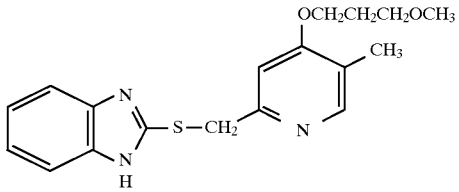

$^1$H-NMR (CDCl$_3$) δ; 1.90~2.24 (m, 2H), 2.16 (s, 3H), 3.31 (s, 3H), 3.51 (t, J=6.2 Hz, 2H), 4.08 (t, J=6.2 Hz, 2H), 4.22 (s, 2H), 6.74 (s, 1H), 6.99~7.22 (m, 2H), 7.32~7.58 (m, 2H), 8.16 (s, 1H)

EXAMPLE 91

Sodium Salt of 2-{4-(3-Methoxypropoxy)-5-Methylpyridine-2-Yl}Methylsulfinyl-1H-Benzimidazole

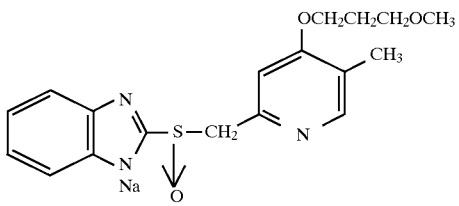

$^1$H-NMR (DMSO-d$_6$) δ; 1.56~1.87 (m, 2H), 2.00 (s, 3H), 3.16 (s, 3H), 3.20~3.72 (m, 4H), 6.16~6.60 (m, 2H), 6.49 (s, 1H), 6.68~6.92 (m, 2H), 7.28~7.50 (m, 2H), 8.13 (s, 1H)

EXAMPLE 92

2-{4-(3-Methoxypropoxy)-3-Methylpyridine-2-Yl}Methylthio-Benzothiazole

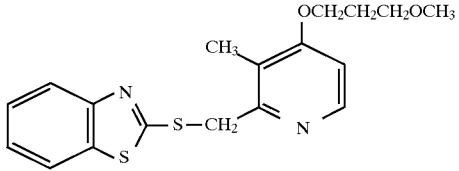

A mixture comprising 0.8 g of 2-chloromethyl-4-(3-methoxypropoxy)-3-methylpyridine hydrochloride, 0.5 g of 2-mercaptobenzothiazole, 0.36 g of sodium hydroxide and 30 ml of ethanol was stirred at a room temperature for 6 hours and distilled under a reduced pressure to remove the ethanol. The residue was purified by silica gel column chromatography to obtain 0.85 g of the title compound as a pale yellow crystal.

$^1$H-NMR (CDCl$_3$) δ; 1.9~2.2 (m, 2H), 2.30 (s, 3H), 3.35 (s, 3H), 3.56 (t, J=6.1 Hz, 2H), 4.10 (t, J=6.1 Hz, 2H), 4.81 (s, 2H), 6.70 (d, J=5.7 Hz, 1H), 7.1~7.5 (m, 2H), 7.5~7.9 (m, 2H), 8.29 (d, J=5.7 Hz, 1H)

EXAMPLE 93

2-{4-(3-Methoxypropoxy)-3-Methylpyridine-2-Yl}Methylsulfinylbenzothiazole

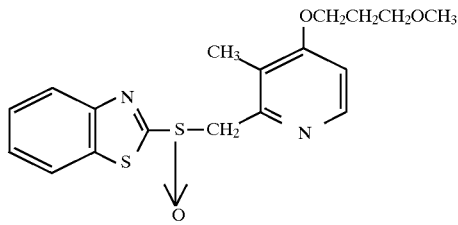

0.6 g of 2-{4-(3-methoxypropoxy)-3-methylpyridine-2-yl}methylthiobenzothiazole was dissolved in 20 ml of dichloromethane to obtain a solution. 0.36 g of 80% m-chloroperbenzoic acid was added to the solution at −45° C. After one hour, 0.34 g of triethylamine and 30 ml of a saturated aqueous solution of sodium hydrogencarbonate were added to the obtained mixture. The resulting mixture was stirred at a room temperature for 30 minutes. The dichloromethane layer was separated, washed with a saturated aqueous solution of sodium hydrogencarbonate twice, dried over magnesium sulfate and filtered. The filtrate was concentrated to obtain a residue. This residue was purified by silica gel column chromatography to obtain 0.17 g of the title compound as a white crystal.

$^1$H-NMR (CDCl$_3$) δ; 1.95~2.18 (m, 2H), 2.20 (s, 3H), 3.34 (s, 3H), 3.54 (t, J=6.1 Hz, 2H), 4.10 (t, J=6.1 Hz, 2H), 4.67 (s, 2H), 6.71 (d, J=5.7 Hz, 1H), 7.40~7.0 (m, 2H), 7.92~8.20 (m, 2H), 8.25 (d, J=5.7 Hz, 1H)

EXAMPLE 94

2-{4-(3-Methoxypropoxy)-3-Methylpyridine-2-Yl}Methylthio-1-Methylbenzimidazole

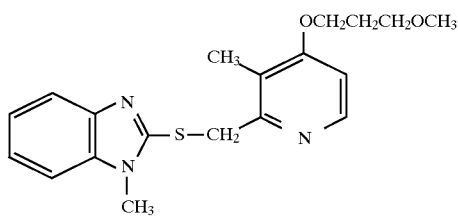

0.5 g of 2-{4-(3-hydroxypropoxy)-3-methylpyridine-2-yl}methylthio-1H-benzimidazole was dissolved in 30 ml of dimethylformamide to obtain a solution. 0.24 g of 60% sodium hydride was added to the solution at 0° C. The obtained mixture was stirred at 40° C. for one hour and cooled again to 0° C., followed by the addition of 0.5 g of methyl iodide. The obtained mixture was stirred at a room temperature for 3 hours. Then, a saturated aqueous solution of ammonium chloride was added to the resulting mixture to stop the reaction. The reaction mixture was distilled under a reduced pressure to remove the solvent and the residue was purified by silica gel column chromatography to obtain 0.3 g of the title compound as a pale yellow crystal.

$^1$H-NMR (CDCl$_3$) δ; 1.95~2.21 (m, 2H), 2.30 (s, 3H), 3.35 (s, 3H), 3.54 (t, J=6.2 Hz, 2H), 3.67 (s, 3H), 4.10 (t, J=6.2 Hz, 2H), 4.80 (s, 2H), 6.68 (d, J=5.7 Hz, 1H), 7.16~7.30 (m, 3H), 7.57~7.80 (m, 1H), 8.29 (d, J=5.7 Hz, 1H)

EXAMPLE 95

2-{4-(3-Methoxypropoxy)-3-Methylpyridine-2-Yl}Methylsulfinyl-1-Methylbenzimidazole

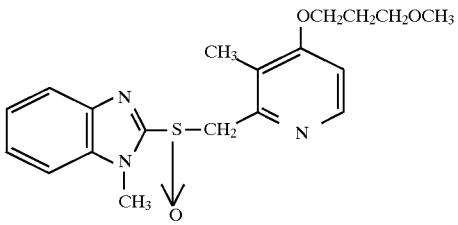

0.25 g of 2-{4-(3-methoxypropoxy)-3-methylpyridine-2-yl}methylthio-1-methylbenzimidazole was dissolved in 20 ml of dichloromethane to obtain a solution. 0.18 g of 80% m-chloroperbenzoic acid was added to the solution at −50° C. The obtained mixture was stirred for one hour, followed by the addition of 0.14 g of triethylamine and 20 ml of a saturated aqueous solution of sodium hydrogencarbonate. The obtained mixture was stirred at a room temperature for one hour. The dichloromethane layer was separated, washed with a saturated aqueous solution of sodium hydrogencarbonate twice, dried over magnesium sulfate and filtered. The filtrate was concentrated to obtain a residue. This residue was purified by silica gel column chromatography to obtain 0.12 g of the title compound as a pale yellow crystal.

$^1$H-NMR (CDCl$_3$) δ; 1.98~2.12 (m, 2H), 2.22 (s, 3H), 3.33 (s, 3H), 3.53 (t, J=6.2 Hz, 2H), 3.98 (s, 3H), 4.06 (t, J=6.2 Hz, 2H), 4.96 (s, 2H), 6.65 (d, J=5.7 Hz, 1H), 7.25~7.40 (m, 3H), 7.75~7.87 (m, 1H), 8.15 (d, J=5.7 Hz, 1H)

EXAMPLE 96

1-Ethoxycarbonyl-2-{4-(3-Methylpropoxy)-3-Methylpyridine-2-Yl}Methylthiobenzimidazole

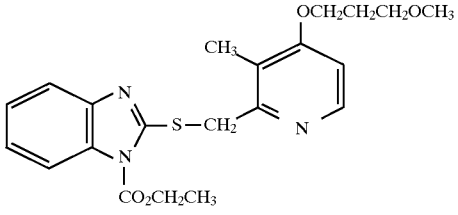

0.8 g of 2-{4-(3-methoxypropoxy)-3-methylpyridine-2-yl}methylthio-1H-benzimidazole was dissolved in 10 ml of dimethylformamide to obtain a solution. 0.23 g of 60% sodium hydride was added to this solution at 0° C. The obtained mixture was stirred for 15 minutes. 0.4 g of ethyl chlorocarbonate was dropwise added to the resulting mixture at 0° C. The obtained mixture was stirred at a room temperature for one hour. A saturated aqueous solution of ammonium chloride was added to the resulting mixture to stop the reaction. The reaction mixture was extracted with chloroform. The extract was dried over magnesium sulfate and filtered. The filtrate was concentrated to obtain a residue. This residue was purified by silica gel column chromatography to obtain 0.82 g of the title compound as a white crystal.

$^1$H-NMR (CDCl$_3$) δ; 1.50 (t, J=7.0 Hz, 3H), 1.95~2.20 (m, 2H), 2.32 (s, 3H), 3.36 (s, 3H), 3.56 (t, J=6.2 Hz, 2H), 4.10 (t, J=6.2 Hz, 2H), 4.54 (q, J=7.0 Hz, 2H), 4.77 (s, 2H), 6.69 (d, J=5.7 Hz, 1H), 7.1~7.4 (m, 2H), 7.4~7.7 (m, 1H), 7.7~7.95 (m, 1H), 8.30 (d, J=5.7 Hz, 1H)

EXAMPLE 97

1-Ethoxycarbonyl-2-{4-(3-Methoxypropoxy)-3-Methylpyridine-2-Yl}Methylsulfinylbenzimidazole

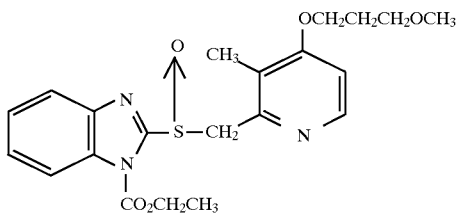

0.6 g of 1-ethoxycarbonyl-2-{4-(3-methoxypropoxy)-3-methylpyridine-2-yl}methylthiobenzimidazole was dissolved in 20 ml of dichloromethane to obtain a solution. 0.4 g of m-chloroperbenzoic acid was added to the solution at −45° C. After one hour, 0.3 g of triethylamine and 20 ml of a saturated aqueous solution of sodium hydrogencarbonate were added to the resulting mixture. The obtained mixture was stirred at a room temperature for 30 minutes. The dichloromethane layer was separated, washed with a saturated aqueous solution of sodium hydrogencarbonate twice, dried over magnesium sulfate and filtered. The filtrate was concentrated to obtain a residue. This residue was purified by silica gel column chromatography to obtain 0.21 g of the title compound as a yellow oil.

$^1$H-NMR (CDCl$_3$) δ; 1.54 (t, J=7.0 Hz, 3H), 1.99~2.20 (m, 2H), 2.30 (s, 3H), 3.35 (s, 3H), 3.55 (t, J=6.2 Hz, 2H), 4.06 (t, J=6.2 Hz, 2H), 4.61 (q, J=7.0 Hz, 2H), 4.74 (ABq, J=12.8 Hz, Δv=8.6 Hz, 2H), 6.60 (d, J=5.7 Hz, 1H), 7.3~7.5 (m, 2H), 7.7~8.0 (m, 2H), 8.03 (d, J=5.7 Hz, 1H)

What is claimed is:

1. A compound represented by the formula;

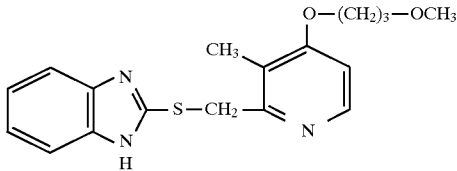

or a pharmaceutically acceptable salt thereof.

2. The compound of claim 1 as the sodium salt.

* * * * *

Disclaimer

5,840,910 — Shigeru Souda, Ushiku; Norihiro Ueda, Niihari-gun; Shuhei Miyazawa, Toride; Katsuya Tagami, Niihari-gun; Seiichiro Nomoto, Ushiku; Makoto Okita, Tsuchiura; Naoyuki Shimomura, Niihari-gun; Toshihiko Kaneko; Masatoshi Fujimoto, both of Tsukuba-gun, all of Japan; Manabu Murakami, Rockville, Md.; Kiyoshi Oketani, Tsukuba-gun; Hideaki Fujisaki, Niihari-gun; Hisashi Shibata, Tsuchiura; Tsuneo Wakabayashi, Mito, all of Japan. PYRIDINE DERIVATIVES HAVING ANTI-ULCERATIVE ACTIVITY. Patent dated November 24, 1998. Disclaimer filed October 18, 2006, by the assignee, Eisai Co., Ltd.

Hereby enters this disclaimer to claims 1 and 2, of said patent.

*(Official Gazette, July 31, 2007)*

(12) EX PARTE REEXAMINATION CERTIFICATE (6236th)
United States Patent
Souda et al.

(10) Number: US 5,840,910 C1
(45) Certificate Issued: *May 27, 2008

(54) PYRIDINE DERIVATIVES HAVING ANTI-ULCERATIVE ACTIVITY

(75) Inventors: Shigeru Souda, Ushiku (JP); Norihiro Ueda, Niihari-gun (JP); Shuhei Miyazawa, Toride (JP); Katsuya Tagami, Niihari-gun (JP); Seiichiro Nomoto, Ushiku (JP); Makoto Okita, Tsuchiura (JP); Naoyuki Shimomura, Niihari-gun (JP); Toshihiko Kaneko, Tsukuba-gun (JP); Masatoshi Fujimoto, Tsukuba-gun (JP); Manabu Murakami, Rockville, MD (US); Kiyoshi Oketani, Tsukuba-gun (JP); Hideaki Fujisaki, Niihari-gun (JP); Hisashi Shibata, Tsuchiura (JP); Tsuneo Wakabayashi, Mito (JP)

(73) Assignee: Eisai Co., Ltd., Bunkyo-ku, Tokyo (JP)

Reexamination Request:
No. 90/008,220, Sep. 18, 2006

Reexamination Certificate for:
Patent No.: 5,840,910
Issued: Nov. 24, 1998
Appl. No.: 08/354,726
Filed: Dec. 6, 1994

(*) Notice: This patent is subject to a terminal disclaimer.

Related U.S. Application Data

(63) Continuation of application No. 08/187,069, filed on Jan. 27, 1994, now abandoned, which is a division of application No. 07/699,442, filed on May 13, 1991, now abandoned, which is a division of application No. 07/462,328, filed on Dec. 28, 1989, now Pat. No. 5,045,552, which is a continuation of application No. 07/119,386, filed on Nov. 10, 1987, now abandoned.

(30) Foreign Application Priority Data

Nov. 13, 1986 (JP) ............................... 61-270536
Feb. 2, 1987 (JP) ............................... 62-21989
Mar. 31, 1987 (JP) ............................... 62-77784

(51) Int. Cl.
*C07D 405/14* (2006.01)
*C07D 405/00* (2006.01)
*C07D 413/12* (2006.01)
*C07D 413/00* (2006.01)
*C07D 417/00* (2006.01)
*C07D 417/12* (2006.01)
*C07D 401/12* (2006.01)
*C07D 401/14* (2006.01)
*C07D 401/00* (2006.01)
*C07D 417/14* (2006.01)

(52) U.S. Cl. ...................................... 546/273.7
(58) Field of Classification Search ........................ None
See application file for complete search history.

(56) References Cited

FOREIGN PATENT DOCUMENTS

| EP | 0 074 341 | 3/1983 |
| WO | WO 86/02646 | 5/1986 |

*Primary Examiner*—Evelyn Huang

(57) ABSTRACT

Pyridine derivatives useful for preventing or treating peptic ulcers, pharmaceutical preparations and methods of treating peptic ulcers are disclosed.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1 and 2 are now disclaimed.

* * * * *